(12) United States Patent
Peters

(10) Patent No.: US 12,064,420 B2
(45) Date of Patent: Aug. 20, 2024

(54) TIE-2 ACTIVATORS TARGETING THE SCHLEMM'S CANAL

(71) Applicant: EyePoint Pharmaceuticals, Inc., Watertown, MA (US)

(72) Inventor: Kevin Peters, Cincinnati, OH (US)

(73) Assignee: EyePoint Pharmaceuticals, Inc., Watertown, MA (US)

(*) Notice: Subject to any disclaimer, the term of this patent is extended or adjusted under 35 U.S.C. 154(b) by 223 days.

(21) Appl. No.: 17/569,838

(22) Filed: Jan. 6, 2022

(65) Prior Publication Data

US 2022/0211675 A1 Jul. 7, 2022

Related U.S. Application Data

(63) Continuation of application No. 16/860,347, filed on Apr. 28, 2020, now Pat. No. 11,253,502.

(60) Provisional application No. 62/840,068, filed on Apr. 29, 2019.

(51) Int. Cl.
*A61K 31/426* (2006.01)
*A61K 9/00* (2006.01)
*A61P 27/02* (2006.01)

(52) U.S. Cl.
CPC ............ *A61K 31/426* (2013.01); *A61P 27/02* (2018.01); *A61K 9/0048* (2013.01)

(58) Field of Classification Search
CPC ...... A61K 31/426; A61K 9/0048; A61P 27/02
See application file for complete search history.

(56) References Cited

U.S. PATENT DOCUMENTS

| | | | |
|---|---|---|---|
| 953,924 A | 4/1910 | Schweimler |
| 5,919,813 A | 7/1999 | De Juan, Jr. et al. |
| 5,980,929 A | 11/1999 | De Juan, Jr. |
| 6,455,035 B1 | 9/2002 | Suri et al. |
| 7,052,695 B2 | 5/2006 | Kalish |
| 7,226,755 B1 | 6/2007 | Peters et al. |
| 7,309,483 B2 | 12/2007 | Wiegand et al. |
| 7,354,579 B2 | 4/2008 | Holash et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,740,846 B2 | 6/2010 | Gerber et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,311 B2 | 9/2012 | Gray et al. |
| 8,329,916 B2 | 12/2012 | Amarasinghe et al. |
| 8,338,615 B2 | 12/2012 | Gray et al. |
| 8,524,234 B2 | 9/2013 | Rotello et al. |
| 8,524,235 B2 | 9/2013 | Rotello et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,968,766 B2 | 3/2015 | Hughes et al. |
| 8,999,325 B2 | 4/2015 | Peters et al. |
| 8,999,953 B2 | 4/2015 | Loftsson et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,284,285 B2 | 3/2016 | Gray et al. |
| 9,403,789 B2 | 8/2016 | Eissenstat et al. |
| 9,440,963 B2 | 9/2016 | Peters et al. |
| 9,539,245 B2 | 1/2017 | Peters |
| RE46,592 E | 10/2017 | Gray et al. |
| 9,795,594 B2 | 10/2017 | Gray et al. |
| 9,926,367 B2 | 3/2018 | Rotello et al. |
| 9,949,956 B2 | 4/2018 | Shalwitz et al. |
| 9,994,560 B2 | 6/2018 | Janusz et al. |
| 10,150,811 B2 | 12/2018 | Peters et al. |
| 10,220,048 B2 | 3/2019 | Peters et al. |
| 10,329,357 B2 | 6/2019 | Peters et al. |
| 10,463,650 B2 | 11/2019 | Gray et al. |
| 2003/0040463 A1 | 2/2003 | Wiegand et al. |
| 2004/0077065 A1 | 4/2004 | Evdokimov et al. |
| 2008/0268051 A1 | 10/2008 | Hughes et al. |
| 2010/0030487 A1 | 2/2010 | Evdokimov et al. |
| 2010/0226992 A1 | 9/2010 | Kabra |
| 2013/0023542 A1 | 1/2013 | Gray et al. |

(Continued)

FOREIGN PATENT DOCUMENTS

| EP | 1165115 B1 | 5/2003 |
|---|---|---|
| EP | 2142189 B1 | 2/2013 |

(Continued)

OTHER PUBLICATIONS

Amarasinghe, et al., Design and synthesis of potent, non-peptidic inhibitors of HPTPP, Bioorganic & Medicinal Chemistry Letters, 16 (2006) 4252-56.

Baumer, et al. Vascular endothelial cell-specific phosphotyrosine phosphatase (VE-PTP) activity is required for blood vessel development. Blood. Jun. 15, 2006;107(12):4754-62. Epub Mar. 2, 2006.

Bernier-Latmani et al., All TIEd up: mechanisms of Schlemm's canal maintenance, The Journal of Clinical Investigation, 2017, vol. 127 (10), pp. 3594-3597.

"High Eye Pressure and Glaucoma, Available at web.archive.org/web/20140822034439, http://www.glaucoma.org/gleams/high-eyepressure-andglaucoma. php, Accessed on Sep. 28, 2017".

International Search Report and Written Opinion issued in PCT/US2020/030224 on Aug. 28, 2020.

Jeansson, et al., Angiopoietin-1 is essential in mouse vasculature during development and In response to injury, The Journal of Clinical Investigation, Jun. 2011, 121(6):2278-89.

(Continued)

*Primary Examiner* — Erich A Leeser
(74) *Attorney, Agent, or Firm* — Sterne, Kessler, Goldstein & Fox P.L.L.C.

(57) ABSTRACT

Disclosed herein are compounds effective for activation of Tie-2 and inhibition of HPTP-beta. The compounds can provide effective therapy for eye conditions, for example, intraocular pressure, ocular hypertension, and glaucoma.

16 Claims, 22 Drawing Sheets

(56) References Cited

U.S. PATENT DOCUMENTS

| | | |
|---|---|---|
| 2013/0137741 A1 | 5/2013 | Kabra et al. |
| 2013/0190324 A1 | 7/2013 | Kompella et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0175676 A1 | 6/2015 | Fandl et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297740 A1 | 10/2015 | Rau et al. |
| 2016/0000871 A1 | 1/2016 | Quaggin |
| 2016/0015810 A1 | 1/2016 | Deschatelets et al. |
| 2016/0030393 A1 | 2/2016 | Breslin et al. |
| 2016/0045566 A1 | 2/2016 | Purcell et al. |
| 2016/0058828 A1 | 3/2016 | Dumont et al. |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van Slyke et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0251421 A1 | 9/2016 | Brown et al. |
| 2017/0079959 A1 | 3/2017 | Peters |
| 2017/0145416 A1 | 5/2017 | Epstein et al. |
| 2017/0260265 A1 | 9/2017 | Duerr et al. |
| 2017/0314063 A1 | 11/2017 | Quaggin |
| 2017/0349649 A1 | 12/2017 | Rotello et al. |
| 2019/0023773 A1 | 1/2019 | Rotello et al. |
| 2019/0256889 A1 | 8/2019 | Quaggin |
| 2019/0262321 A1 | 8/2019 | Peters et al. |

FOREIGN PATENT DOCUMENTS

| | | | |
|---|---|---|---|
| EP | 3168234 A1 | 5/2017 | |
| WO | WO-9818914 A1 | 5/1998 | |
| WO | WO-0057901 A1 | 10/2000 | |
| WO | WO-0065085 A1 | 11/2000 | |
| WO | WO-03084565 A2 | 10/2003 | |
| WO | WO-2007033216 A2 | 3/2007 | |
| WO | WO-2007116360 A2 | 10/2007 | |
| WO | WO 2008/002569 * | 1/2008 | ........... C07D 277/28 |
| WO | WO-2008002569 A2 | 1/2008 | |
| WO | WO-2008002570 B1 | 4/2008 | |
| WO | WO-2008002571 B1 | 4/2008 | |
| WO | WO-2010081172 A1 | 7/2010 | |
| WO | WO-2010097800 A1 | 9/2010 | |
| WO | WO-2011005330 A1 | 1/2011 | |
| WO | WO-2012047966 A2 | 4/2012 | |
| WO | WO-2013056233 A1 | 4/2013 | |
| WO | WO-2013056240 A1 | 4/2013 | |
| WO | WO-2014145068 A1 | 9/2014 | |
| WO | WO-2015138882 A1 | 9/2015 | |
| WO | WO-2015152416 A1 | 10/2015 | |
| WO | WO-2016022813 A1 | 2/2016 | |
| WO | WO-2016049183 A1 | 3/2016 | |
| WO | WO-2017053566 A1 | 3/2017 | |
| WO | WO-2018124582 A1 | 7/2018 | |
| WO | WO-2021142056 A1 | 7/2021 | |

OTHER PUBLICATIONS

Kernt, et al., Intravitreal bevacizumab (Avastin) treatment is safe in terms of intraocular and blood pressure, Acta Ophthalmologica 85(1):1-4.

Kim et al., Impaired angiopoietin/Tie2 signaling compromises Schlemm's canal integrity and induces glaucoma, The Journal of Clinical Investigation, 2017, vol. 127 (10, pp. 387-3896.

Kurna, Sevda Aydin et al., The Effects of Topical Antiglaucoma Drugs and Monotherapy on the Ocular Surface: A Prospective Study, Journal of Ophthalmology, vol. 2014, Jan. 1, 2014, pp. 1-8, XP055654445, US ISSN:2090-004XX, DOI:10.1155/2014/460483.

Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.

Nawroth, et al. VE-PTP and VE-cadherin ectodomains interact to facilitate regulation of phosphorylation and cell contacts. EMBO J. Sep. 16, 2002;21(18):4885-95.

Shen, et al. Targeting VE-PTP activates TIE2 and stabilizes the ocular vasculature. J Clin Invest. Oct. 2014;124(10):4564-76.

Thomson, Benjamin R. et al., Defects in Angiopoietin-Tie2 signaling lead to dose-dependent glaucoma in mice Program No. 6084, ARVO 2016 Annual Meeting Abstracts, May 5, 2016, pp. 1-4, XP055569557, Retrieved from the Internet.

Thomson et al., A lymphatic defect causes ocular hypertension and glaucoma in mice, The Journal of clinical Investigation, 2014, vol. 124 (10), pp. 4320-4324.

"Types of Glaucoma, Available at web.archive.org/web/20140822230205, www.glaucoma.org/glaucoma/types-of-glaucoma.php, Accessed on Sep. 28, 2017".

Vestweber, et al., Molecular Mechanisms That Control Endothelial Cell Contacts, J. Pathol 2000, 190:281-91.

Xp-0027789738, Database WPI Week 201571 Thomson Scientific, London, GB, AN 2015-61106C & WO 2015/152415A1 (Shiseido Co. Ltd.) Oct. 8, 2015.

Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.

* cited by examiner

TIE-2 ACTIVATORS TARGETING THE SCHLEMM'S CANAL

CROSS REFERENCE

This application is a continuation of U.S. application Ser. No. 16/860,347, filed Apr. 28, 2020, which claims the benefit of U.S. Provisional Application No. 62/840,068, filed Apr. 29, 2019, each of which is incorporated by reference herein in its entirety.

BACKGROUND

Open angle glaucoma (OAG) is a leading cause of blindness worldwide. A major risk factor for OAG is elevated IOP (IOP). The Angiopoietin/Tie2 pathway is involved in the development and maintenance of Schlemm's canal (SC), a central component of the conventional outflow (CO) pathway. This pathway regulates in part the pressure in the eye.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method for modulating fluid outflow in an eye of a subject in need thereof, the method comprising administering to the subject a therapeutically-effective amount of a Tie-2 activator, wherein administration of the Tie-2 activator in the subject modulates the fluid outflow by at least about 20% as compared to absence of administration.

In some embodiments, the invention provides a method for increasing area of Schlemm's canal in a subject in need thereof, the method comprising administering to the subject a therapeutically-effective amount of a Tie-2 activator, wherein administration of the Tie-2 activator in the subject increases area of Schlemm's canal by at least about 10% as compared to absence of administration.

DETAILED DESCRIPTION

Figure 1A:
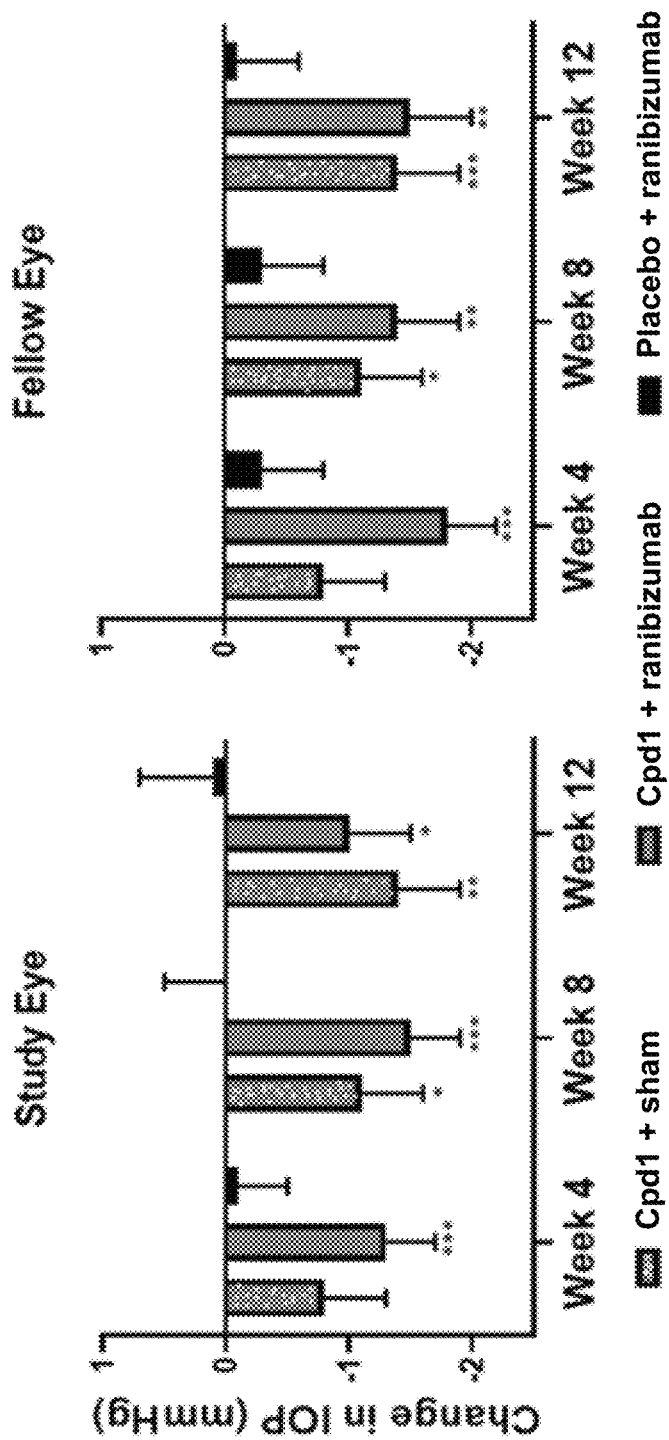
FIG. 1A illustrates the effect of subcutaneous Compound 1 alone or as an adjunct to intravitreal ranibizumab on intraocular pressure (IOP) in ocular normotensive patients with diabetic eye disease.

In humans, VE-PTP (HPTP-β), a negative regulator of Tie-2 activation, is expressed in the SC endothelium, but not in the trabecular meshwork. Topical ocular administration of a Tie-2 activator can increase Tie-2 activation in the SC endothelium, reduce TOP, and increase outflow facility. These effects indicate that VE-PTP can participate in Tie-2-mediated regulation of conventional outflow homeostasis at the level of the SC to lower intraocular pressure by selectively targeting the barrier function of the SC.

Schlemm's Canal.

The Schlemm's Canal (SC) expresses lymphatic endothelial markers such as Prox1, VEGFR3, and the integrin chain α9. SC endothelium also expresses blood vascular endothelial markers including Tie-2, VEGFR2, PECAM1/CD31, and endomucin. BMPR2 and VEGFR-3 can physically associate to form a complex in which VEGFR-3 is required for BMR-mediated receptor stimulation and downstream signaling, such as SMAD phosphorylation and Inhibitor of DNA Binding (ID) gene transcription. Inactivation of the tyrosine kinase encoded by VEGFR-3 can be linked to congenital hereditary lymphedema. VEGFR-3 can be essential for development of Schlemm's canal and can be a critical regulator of lymphangiogenesis in the Schlemm's canal.

OAG is characterized by death of retinal ganglion cells, degeneration of the optic nerve, and progressive vision loss. Elevated intraocular pressure (IOP) is a primary and a major modifiable risk factor for OAG. Effective reduction in TOP can slow and reduce the likelihood of vision loss.
Conventional Outflow (CO) Pathway.

The CO pathway, comprising the trabecular meshwork (TM) and SC, regulates TOP within a narrow range in healthy eyes and is the site of increased resistance to aqueous outflow in OAG. Therapies to reduce TOP can work by either decreasing the formation of aqueous humor, or by increasing outflow through the secondary, uveoscleral outflow pathway. Development of agents that target the pathology in the CO pathway can help to improve treatment efficacy (REFS), either alone or in combination with agents that treat glaucoma.

The angiopoietin (Angpt)—tyrosine kinase with immunoglobulin-like and EGF-like domains 2 (Tie-2) pathway is important in the development and maintenance of the CO pathway. Tie-2 is expressed and activated in SC endothelial cells, both during development, and after a mature SC lumen has formed. Disruption of the Tie-2 pathway in mice, by conditional knockout of Tie-2, or Tie-2 ligands (Angpt1 and Angpt2), early in postnatal development can result in failure of SC formation. The failure of SC formation can be associated with increased TOP and optic nerve pathology resembling human congenital glaucoma. Similarly, Tie-2 pathway disruption in 8-week old mice can result in degeneration of SC, TOP elevation, and optic nerve pathology resembling OAG. Both Tie-2 and Angpt1 loss of function variants can be associated with a risk of congenital glaucoma, and single-nucleotide polymorphisms in the Angpt1 promoter region can be associated with OAG risk.

Compounds that activate Tie-2 can treat disorders and injuries associated with vascular instability, which include, for example, nephropathy, acute kidney injury, cancer, systemic vascular leak syndromes including acute lung injury (ALI) and acute respiratory distress syndrome (ARDS), hypertension including hypertensive crisis/urgency, pulmonary artery hypertension, hepatorenal syndrome, cerebrovascular leakage, and brain edema.

Compounds that activate Tie-2 can treat disorders of the vascular networks of the eye that include, for example, retinopathies, ocular edema, and ocular neovascularization. Non-limiting examples of diseases or conditions that involve retinopathy, ocular edema, or neovascularization can include, for example, diabetic macular edema, age-related macular degeneration (wet form), choroidal neovascularization, diabetic retinopathy, retinal vein occlusion (central or branch), ocular trauma, surgery induced edema, surgery induced neovascularization, cystoid macular edema, ocular ischemia, and uveitis. These diseases or conditions are characterized by changes in the ocular vasculature whether progressive or non-progressive, whether a result of an acute disease or condition, or a chronic disease or condition.

Compounds that activate Tie-2 can also treat disorders related to the impairment of aqueous humor outflow from the anterior chamber of the eye, which can include, for example, glaucoma, primary glaucoma, pseudoexfoliative glaucoma, pigmentary glaucoma, primary juvenile glaucoma, open angle glaucoma, wide-angle glaucoma, close-angle glaucoma, congenital glaucoma, acquired glaucoma, secondary glaucoma, inflammatory glaucoma, phacogenic glaucoma, or neovascular glaucoma. In some cases, a Tie-2 activator of the disclosure can stabilize vasculature associated with the trabecular meshwork, reducing intraocular pressure and treating ocular hypertension.
Modulators of Tie-2.

Compounds disclosed herein can be effective as Tie-2 modulators. A compound disclosed herein can activate Tie-2. The compounds can affect that activity, for example, by binding or inhibiting HPTB-β. In some embodiments, a compound of the disclosure can bind or inhibit HPTPβ in a Schlemm's canal of a subject. Such compounds can bind, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, a compound disclosed herein is a compound of formula:

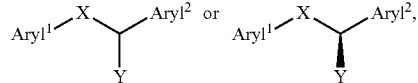

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

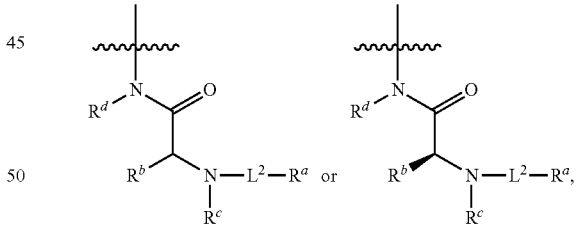

wherein
L$^2$ is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of R$^a$, R$^b$, R$^c$, and R$^d$ forms a ring that is substituted or unsubstituted. R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted. R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L², Rᵃ, Rᶜ, and Rᵈ forms a ring that is substituted or unsubstituted. Rᶜ is H or alkyl which is substituted or unsubstituted, or together with any of L², Rᵃ, Rᵇ, and Rᵈ forms a ring that is substituted or unsubstituted. Rᵈ is H or alkyl which is substituted or unsubstituted, or together with any of L², Rᵃ, Rᵇ, and Rᶜ forms a ring that is substituted or unsubstituted, and Rᵍ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, aryl¹ is substituted or unsubstituted phenyl, aryl² is substituted or unsubstituted heteroaryl, and X is alkylene. In some embodiments, aryl¹ is substituted phenyl, aryl² is substituted heteroaryl, and X is methylene.

In some embodiments, a compound is of the formula:

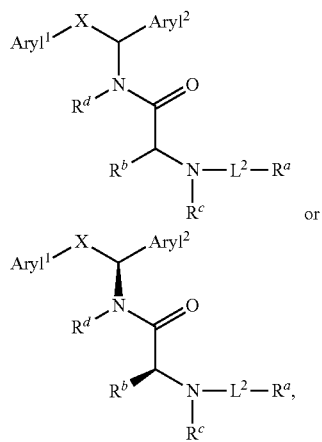

wherein
wherein aryl¹ is para-substituted phenyl, aryl² is substituted heteroaryl, X is methylene. L² is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond. Rᵃ is H, alkyl, alkenyl, alkynyl, aryl, arylalkyl, heterocyclyl, heterocyclylalkyl, heteroaryl, or heteroarylalkyl, any of which is substituted or unsubstituted. Rᵇ is H, alkyl, alkenyl, alkynyl, aryl, arylalkyl, heterocyclyl, heterocyclylalkyl, heteroaryl, or heteroarylalkyl, any of which is substituted or unsubstituted. Rᶜ is H or alkyl which is substituted or unsubstituted, and Rᵈ is H or alkyl which is substituted or unsubstituted.

In some embodiments, aryl¹ is para-substituted phenyl, aryl¹ is a substituted thiazole moiety. X is methylene, L² together with the nitrogen atom to which L is bound forms a carbamate linkage, Rᵃ is alkyl, which is substituted or unsubstituted, Rᵇ is arylalkyl, which is substituted or unsubstituted, Rᶜ is H, and Rᵈ is H.

In some embodiments, Aryl² is:

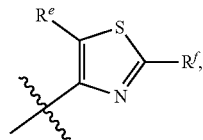

wherein Rᵉ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted, and Rᶠ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted.

In some embodiments, Rᵉ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted, and Rᶠ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, Rᵉ is H, OH, F, Cl, Br, I, alkyl, or an alkoxy group, any of which is substituted or unsubstituted and Rᶠ is alkyl, aryl, heterocyclyl, or heteroaryl, any of which is substituted or unsubstituted. In some embodiments, aryl¹ is 4-phenylsulfamic acid, Rᵃ is alkyl, which is substituted or unsubstituted, Rᵇ is arylalkyl, which is substituted or unsubstituted, Rᵉ is H; and Rᶠ is heteroaryl. In some embodiments, aryl¹ is 4-phenylsulfamic acid, Rᵃ is alkyl, which is substituted or unsubstituted, Rᵇ is arylalkyl, which is substituted or unsubstituted, Rᵉ is H; and Rᶠ is alkyl In some embodiments, Aryl² is:

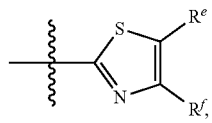

wherein Rᵉ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted, Rᶠ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted. In some embodiments, Rᵉ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted and Rᶠ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, Rᵉ is H, OH, F, Cl, Br, I, alkyl, or an alkoxy group, any of which is substituted or unsubstituted and Rᶠ is alkyl, aryl, heterocyclyl, or heteroaryl, any of which is substituted or unsubstituted. In some embodiments, aryl¹ is 4-phenylsulfamic acid, $R^a$ is alkyl, which is substituted or unsubstituted, $R^b$ is arylalkyl, which is substituted or unsubstituted, $R^e$ is H; and $R^f$ is heteroaryl.

In some embodiments, a substituted phenyl group is:

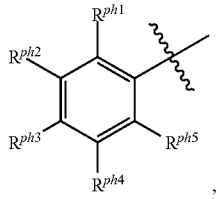

wherein:
each of $R^{ph1}$, $R^{ph2}$, $R^{ph3}$, $R^{ph4}$, and $R^{ph5}$ is independently H, OH, F, Cl, Br, I, CN, sulfamic acid, tosylate, mesylate, triflate, besylate, alkyl, alkenyl, alkynyl, an alkoxy group, a sulfhydryl group, a nitro group, a nitroso group, an azido group, a sulfoxide group, a sulfone group, a sulfonamide group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl.

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, and ester groups.

The following are non-limiting examples of units which can substitute for hydrogen atoms:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings;
v) substituted or unsubstituted $C_1$-$C_9$ heteroaryl rings;
vi) —$(CR^{102a}R^{102b})_aOR^{101}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{102a}R^{102b})_aC(O)R^{101}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{102a}R^{102b})_aC(O)OR^{101}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
ix) —$(CR^{102a}R^{102b})_aC(O)N(R^{101})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{102a}R^{102b})_aN(R^{101})_2$, for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{102a}R^{102b})_aCN$;
xiii) —$(CR^{102a}R^{102b})_aNO_2$;
xiv) —$CH_jX_k$; wherein X is halogen, the index j is an integer from 0 to 2, j+k=3; for example, —$CH_2F$, —$CHF_2$, —$CF_3$, —$CCl_3$, or —$CBr_3$;
xv) —$(CR^{102a}R^{102b})_aSR^{101}$; —SH, —$CH_2SH$, —$SCH_3$, —$CH_2SCH_3$, —$SC_6H_5$, and —$CH_2SC_6H_5$;
xvi) —$(CR^{102a}R^{102b})_aSO_2R^{101}$; for example, —$SO_2H$, —$CH_2SO_2H$, —, —$SO_2CH_3$, —$CH_2SO_2CH_3$, —$SO_2C_6H_5$, and —$CH_2SO_2C_6H_5$; and
xvii) —$(CR^{102a}R^{102b})_aSO_3R^{101}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{101}$ is independently hydrogen, substituted or unsubstituted $C_1$-$C_6$ linear, branched, or cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or branched alkyl; the index "a" is from 0 to 4.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of substituted and unsubstituted acyclic hydrocarbyl include:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), and 3-carboxypropyl ($C_3$).

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), and 7-hydroxy-7-methyloct-3,5-dien-2-yl ($C_9$).

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), and 5-hydroxy-5-ethylhept-3-ynyl ($C_9$).

Non-limiting examples of substituted and unsubstituted cyclic hydrocarbyl include: rings comprising from 3 to 20 carbon atoms, wherein the atoms which comprise said rings are limited to carbon atoms, and further each ring can be independently substituted with one or more moieties capable of replacing one or more hydrogen atoms. The following are non-limiting examples of substituted and unsubstituted carbocyclic rings:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Also included are $C_1$-$C_6$ tethered cyclic hydrocarbyl units (whether carbocyclic units, $C_6$ or $C_{10}$ aryl units, heterocyclic units, or heteroaryl units) can be connected to another moiety, unit, or core of the molecule by way of a $C_1$-$C_6$ alkylene unit. Non-limiting examples of tethered cyclic hydrocarbyl units include benzyl $C_1$-($C_6$) having the formula:

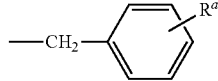

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxyphenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkyleneheteroaryl units, for example a 2-picolyl $C_1$-($C_6$) unit having the formula:

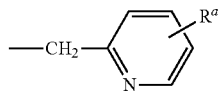

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

A halo group can be any halogen atom, for example, fluorine, chlorine, bromine, or iodine.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

Non-limiting examples of aryl groups can include: i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N)-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$); and ii) $C_6$ or $C_{10}$ aryl rings fused with 1 or 2 saturated rings to afford $C_8$-$C_{20}$ ring systems, non-limiting examples of which include, bicyclo[4.2.0]octa-1,3,5-trienyl ($C_8$), and indanyl ($C_9$).

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$); and ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

Non-limiting examples of heteroaryl include: i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$); and ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

Non-limiting examples of heteroaryl include 1,2,3,4-tetrahydroquinoline having the formula:

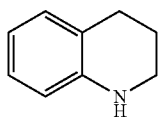

6,7-Dihydro-5H-cyclopentapyrimidine having the formula:

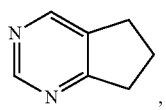

and 1,2,3,4-tetrahydro-[1,8]naphthpyridine having the formula:

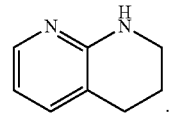

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Compounds Disclosed Herein.

In some embodiments, a compound of the disclosure has Formula (I):

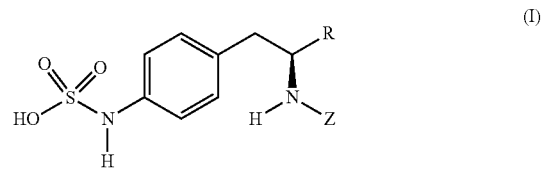

(I)

wherein the carbon atom having the amino unit has the stereochemistry indicated in the following formula:

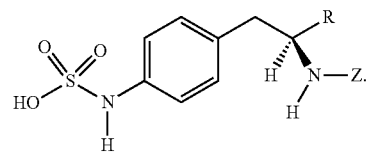

The units which comprise R and Z can comprise units having any configuration, and, as such, a compound of the disclosure can be a single enantiomer, a diastereomer, or pairs or combinations thereof. In addition, the compounds can be isolated as salts or hydrates. In the case of salts, the compounds can comprise more than one cation or anion. In the case of hydrates, any number of water molecules, or fractional part thereof (for example, less than 1 water molecule present for each molecule of analogue) can be present.

R Units

R is a substituted or unsubstituted thiazolyl unit having the formula:

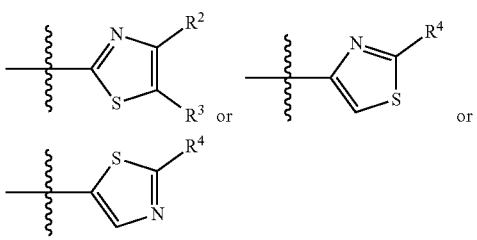

R², R³, and R⁴ are substituent groups that can be independently chosen from a wide variety of non-carbon atom containing units (for example, hydrogen, hydroxyl, amino, halogen, and nitro) or organic substituent units, such as substituted and unsubstituted acyclic hydrocarbyl and cyclic hydrocarbyl units as described herein. The carbon comprising units can comprise, for example, from 1 to 12 carbon atoms, or 1 to 10 carbon atoms, or 1 to 6 carbon atoms.

An example of compounds of Formula (I) include compounds wherein R units are thiazol-2-yl units having the formula:

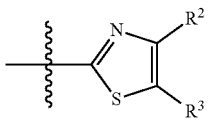

wherein $R^2$ and $R^3$ are each independently chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_2$-$C_6$ linear, $C_3$-$C_6$ branched, or $C_3$-$C_6$ cyclic alkenyl;
iv) substituted or unsubstituted $C_2$-$C_6$ linear or $C_3$-$C_6$ branched alkynyl;
v) substituted or unsubstituted $C_6$ or $C_{10}$ aryl;
vi) substituted or unsubstituted $C_1$-$C_9$ heteroaryl;
vii) substituted or unsubstituted $C_1$-$C_9$ heterocyclic; or
viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen from:
i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_1$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;
vi) —$(CR^{21a}R^{21b})_pR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_pC(O)R^{20}$, for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_pC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
ix) —$(CR^{21a}R^{21b})_pC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_pN(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_pCN$;
xiii) —$(CR^{21a}R^{21b})_pNO_2$;
xiv) —$(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3^-$;
xv) —$(CR^{21a}R^{21b})_pSR^{20}$, SH, —$CH_2SH$, —$SCH_3$, —$CH_2SCH_3$, —$SC_6H_5$, and —$CH_2SC_6H_5$;
xvi) —$(CR^{21a}R^{21b})_pSO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{21a}R^{21b})_pSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;
wherein each $R^{20}$ is independently hydrogen, substituted or unsubstituted $C_1$-$C_4$ linear, $C_3$-$C_4$ branched, or $C_3$-$C_4$ cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or $C_3$-$C_4$ branched alkyl; the index p is from 0 to 4.

An example of compounds of Formula (I) includes R units having the formula:

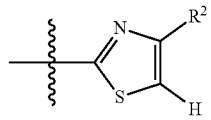

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), cyclopropyl ($C_3$), n-hexyl ($C_6$), 4-methylpentyl ($C_6$), and cyclohexyl ($C_6$).

An example of compounds of Formula (I) include R units having the formula:

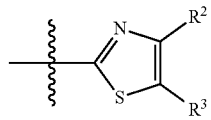

wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl (CO or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

An example of compounds of Formula (I) includes R units wherein $R^3$ is hydrogen and $R^2$ is a substituted alkyl unit, said substitutions chosen from:
i) halogen: —F, —Cl, —Br, and —I;
ii) —N($R^{11}$)$_2$; and
iii) —O$R^{11}$;
wherein each $R^{11}$ is independently hydrogen or $C_1$-$C_4$ linear or $C_3$-$C_4$ branched alkyl. Non-limiting examples of units that can be a substitute for a $R^2$ or $R^3$ hydrogen atom on R units include —$CH_2F$, —$CHF_2$, —$CF_3$, —$CH_2CF_3$, —$CH_2CH_2CF_3$, —$CH_2C_1$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and $CH_2NH(CH_2CH_3)$.

Further non-limiting examples of units that can be a substitute for a $R^2$ or $R^3$ hydrogen atom on R units include 2,2-difluorocyclopropyl, 2-methoxycyclohexyl, and 4-chlorocyclohexyl.

An example of compounds of Formula (I), R units include units wherein $R^3$ is hydrogen and $R^2$ is phenyl or substituted phenyl, wherein non-limiting examples of $R^2$ units include phenyl, 3,4-dimethylphenyl, 4-tert-butylphenyl, 4-cyclopropylphenyl, 4-diethylaminophenyl, 4-(trifluoromethyl)phenyl, 4-methoxyphenyl, 4-(difluoromethoxy)-phenyl, 4-(trifluoromethoxy)phenyl, 3-chloropheny, 4-chlorophenyl, and 3,4-dichloro-phenyl, which when incorporated into the definition of R affords the following R units 4-phenylthiazol-2-yl, 3,4-dimethylphenylthiazol-2-yl, 4-tert-butylphenylthiazol-2-yl, 4-cyclopropylphenylthiazol-2-yl, 4-diethylaminophenylthiazol-2-yl, 4-(trifluoromethyl)-phenylthiazol-2-yl, 4-methoxyphenylthiazol-2-yl, 4-(difluoromethoxy)phenylthiazol-2-yl, 4-(trifluoromethoxy)phenylthiazol-2-yl, 3-chlorophenylthiazol-2-yl, 4-chlorophenylthiazol-2-yl, and 3,4-dichlorophenylthiazol-2-yl.

An example of compounds of Formula (I) includes R units wherein $R^2$ is chosen from hydrogen, methyl, ethyl, n-propyl, and iso-propyl and $R^3$ is phenyl or substituted phenyl. A non-limiting example of a R unit according to the fifth aspect of the first category of R units includes 4-methyl-5-phenylthiazol-2-yl and 4-ethyl-5-phenylthiazol-2-yl.

An example of compounds of Formula (I) includes R units wherein $R^3$ is hydrogen and $R^2$ is a substituted or unsubstituted heteroaryl unit chosen from 1,2,3,4-tetrazol-1-yl,1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Further non-limiting example of compounds of Formula (I) includes R units wherein $R^2$ is substituted or unsubstituted thiophen-2-yl, for example thiophen-2-yl, 5-chlorothiophen-2-yl, and 5-methylthiophen-2-yl.

An example of compounds of Formula (I) includes R units wherein $R^2$ is substituted or unsubstituted thiophen-3-yl, for example thiophen-3-yl, 5-chlorothiophen-3-yl, and 5-methylthiophen-3-yl.

An example of compounds of Formula (I) includes R units wherein $R^2$ and $R^3$ are taken together to form a saturated or unsaturated ring having from 5 to 7 atoms. Non-limiting examples of the sixth aspect of the first category of R units include 5,6-dihydro-4H-cyclopenta[d]thiazol-2-yl and 4,5,6,7-tetrahydrobenzo[d]thiazol-2-yl.

Further examples of compounds of Formula (I) include R units that are thiazol-4-yl or thiazol-5-yl units having the formula:

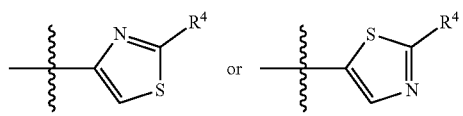

wherein $R^4$ is a unit chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_2$-$C_6$ linear, $C_3$-$C_6$ branched, or $C_3$-$C_6$ cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl; or
vii) substituted or unsubstituted $C_1$-$C_9$ heterocyclic.

The following are non-limiting examples of units that can substitute for one or more hydrogen atoms on the $R^4$ units. The following substituents, as well as others not herein described, are each independently chosen:
i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_1$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings;
v) substituted or unsubstituted $C_1$-$C_9$ heteroaryl rings;
vi) —$(CR^{21a}R^{21b})_pR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_pC(O)R^{20}$, for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_pC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
ix) —$(CR^{21a}R^{21b})_pC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_pN(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;

xii) —$(CR^{21a}R^{21b})_p$CN;

xiii) —$(CR^{21a}R^{21b})_p$NO$_2$;

xiv) —$(CH_jX_{k'})_hCH_jX_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3^-$;

xv) —$(CR^{21a}R^{21b})_p$SR$^{20}$, SH, —CH$_2$SH, —SCH$_3$, —CH$_2$SCH$_3$, —SC$_6$H$_5$, and —CH$_2$SC$_6$H$_5$;

xvi) —$(CR^{21a}R^{21b})_p$SO$_2$R$^{20}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xvii) —$(CR^{21a}R^{21b})_p$SO$_3$R$^{20}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{20}$ is independently hydrogen, substituted or unsubstituted C$_1$-C$_4$ linear, C$_3$-C$_4$ branched, or C$_3$-C$_4$ cyclic alkyl, phenyl, benzyl, heterocyclic, or heteroaryl; or two R$^{20}$ units can be taken together to form a ring comprising 3-7 atoms; R$^{21a}$ and R$^{21b}$ are each independently hydrogen or C$_1$-C$_4$ linear or C$_3$-C$_4$ branched alkyl; the index p is from 0 to 4.

An example of compounds of Formula (I) includes R units wherein R$^4$ is hydrogen.

An example of compounds of Formula (I) includes R units wherein R$^4$ is a unit chosen from methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$). Non-limiting examples of this aspect of R includes 2-methylthiazol-4-yl, 2-ethylthiazol-4-yl, 2-(n-propyl)thiazol-4-yl, and 2-(iso-propyl)thiazol-4-yl.

An example of compounds of Formula (I) includes R units wherein R$^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

An example of compounds of Formula (I) includes R units wherein R$^4$ is substituted or unsubstituted heteroaryl, non-limiting examples of which include thiophen-2-yl, thiophen-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Another example of 5-member ring R units includes substituted or unsubstituted imidazolyl units having the formula:

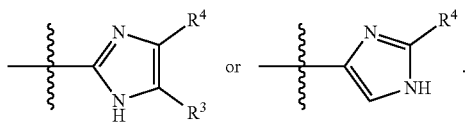

One example of imidazolyl R units includes imidazol-2-yl units having the formula:

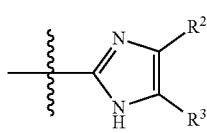

wherein R$^2$ and R$^3$ are each independently chosen from:

i) hydrogen;

ii) substituted or unsubstituted C$_1$-C$_6$ linear, C$_3$-C$_6$ branched, or C$_3$-C$_6$ cyclic alkyl;

iii) substituted or unsubstituted C$_2$-C$_6$ linear, C$_3$-C$_6$ branched, or C$_3$-C$_6$ cyclic alkenyl;

iv) substituted or unsubstituted C$_2$-C$_6$ linear or branched alkynyl;

v) substituted or unsubstituted C$_6$ or C$_{10}$ aryl;

vi) substituted or unsubstituted C$_1$-C$_9$ heteroaryl;

vii) substituted or unsubstituted C$_1$-C$_9$ heterocyclic; or viii) R$^2$ and R$^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the R$^2$ and R$^3$ units. The following substituents, as well as others not herein described, are each independently chosen:

i) C$_1$-C$_{12}$ linear, C$_3$-C$_{12}$ branched, or C$_3$-C$_{12}$ cyclic alkyl, alkenyl, and alkynyl; methyl (C$_1$), ethyl (C$_2$), ethenyl (C$_2$), ethynyl (C$_2$), n-propyl (C$_3$), iso-propyl (C$_3$), cyclopropyl (C$_3$), 3-propenyl (C$_3$), 1-propenyl (also 2-methylethenyl) (C$_3$), isopropenyl (also 2-methylethen-2-yl) (C$_3$), prop-2-ynyl (also propargyl) (C$_3$), propyn-1-yl (C$_3$), n-butyl (C$_4$), sec-butyl (C$_4$), iso-butyl (C$_4$), tert-butyl (C$_4$), cyclobutyl (C$_4$), buten-4-yl (C$_4$), cyclopentyl (C$_1$), cyclohexyl (C$_6$);

ii) substituted or unsubstituted C$_6$ or C$_{10}$ aryl; for example, phenyl, naphthyl (also referred to herein as naphthylen-1-yl (C$_{10}$) or naphthylen-2-yl (C$_{10}$));

iii) substituted or unsubstituted C$_6$ or C$_{10}$ alkylenearyl; for example, benzyl, 2-phenylethyl, naphthylen-2-ylmethyl;

iv) substituted or unsubstituted C$_1$-C$_9$ heterocyclic rings; as described herein;

v) substituted or unsubstituted C$_1$-C$_9$ heteroaryl rings; as described herein;

vi) —$(CR^{21a}R^{21b})_zR^{20}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

vii) —$(CR^{21a}R^{21b})_zC(O)R^{20}$, for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;

viii) —$(CR^{21a}R^{21b})_zC(O)OR^{20}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;

ix) —$(CR^{21a}R^{21b})_zC(O)N(R^{20})_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;

x) —$(CR^{21a}R^{21b})_zN(R^{20})_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;

xi) halogen; —F, —Cl, —Br, and —I;

xii) —$(CR^{21a}R^{21b})_z$CN;

xiii) —$(CR^{21a}R^{21b})_z$NO$_2$;

xiv) —$(CH_jX_{k'})_hCH_jX_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3^-$;

xv) —$(CR^{21a}R^{21b})_z$SR$^{20}$, SH, —CH$_2$SH, —SCH$_3$, —CH$_2$SCH$_3$, —SC$_6$H$_5$, and —CH$_2$SC$_6$H$_5$;

xvi) —(CR$^{21a}$R$^{21b}$)$_p$SO$_2$R$^{20}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xvii) —(CR$^{21a}$R$^{21b}$)$_p$SO$_3$R$^{20}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{20}$ is independently hydrogen, substituted or unsubstituted C$_1$-C$_4$ linear, C$_3$-C$_4$ branched, or C$_3$-C$_4$ cyclic alkyl, phenyl, benzyl, heterocyclic, or heteroaryl; or two R$^{20}$ units can be taken together to form a ring comprising 3-7 atoms; R$^{21a}$ and R$^{21b}$ are each independently hydrogen or C$_1$-C$_4$ linear or C$_3$-C$_4$ branched alkyl; the index p is from 0 to 4.

One example of R units includes compounds wherein R units have the formula:

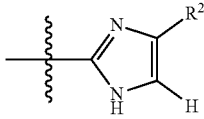

wherein R$^3$ is hydrogen and R$^2$ is a unit chosen from methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$).

Another example of R units includes compounds wherein R$^2$ is a unit chosen from methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$); and R$^3$ is a unit chosen from methyl (CO or ethyl (C$_2$). Non-limiting examples of this aspect of R includes 4,5-dimethylimidazol-2-yl, 4-ethyl-5-methylimidazol-2-yl, 4-methyl-5-ethylimidazol-2-yl, and 4,5-diethylimidazol-2-yl.

An example of R units includes compounds wherein R$^3$ is hydrogen and R$^2$ is a substituted alkyl unit chosen, said substitutions chosen from:
i) halogen: —F, —Cl, —Br, and —I;
ii) —N(R$^{11}$)$_2$; and
iii) —OR$^{11}$;
wherein each R$^{11}$ is independently hydrogen or C$_1$-C$_4$ linear or C$_3$-C$_4$ branched alkyl. 1. Non-limiting examples of units comprising this embodiment of R includes: —CH$_2$F, —CHF$_2$, —CF$_3$, —CH$_2$CF$_3$, —CH$_2$C$_1$, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

An example of R units includes units wherein R$^3$ is hydrogen and R$^2$ is phenyl.

An example of R units includes units wherein R$^3$ is hydrogen and R$^2$ is a heteroaryl unit chosen from 1,2,3,4-tetrazol-1-yl,1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Z Units

Z is a unit having the formula:

R$^1$ is chosen from:
i) hydrogen;
ii) hydroxyl;
iii) amino;
iv) substituted or unsubstituted C$_1$-C$_6$ linear, C$_3$-C$_6$ branched or C$_3$-C$_6$ cyclic alkyl;
v) substituted or unsubstituted C$_1$-C$_6$ linear, C$_3$-C$_6$ branched o C$_3$-C$_6$r cyclic alkoxy;
vi) substituted or unsubstituted C$_6$ or C$_{10}$ aryl;
vii) substituted or unsubstituted C$_1$-C$_9$ heterocyclic rings; or
viii) substituted or unsubstituted C$_1$-C$_9$ heteroaryl rings.

The following are non-limiting examples of units that can substitute for one or more hydrogen atoms on the R$^1$ units. The following substituents, as well as others not herein described, are each independently chosen:

i) C$_1$-C$_{12}$ linear, C$_3$-C$_{12}$ branched, or C$_3$-C$_{12}$ cyclic alkyl, alkenyl, and alkynyl; methyl (C$_1$), ethyl (C$_2$), ethenyl (C$_2$), ethynyl (C$_2$), n-propyl (C$_3$), iso-propyl (C$_3$), cyclopropyl (C$_3$), 3-propenyl (C$_3$), 1-propenyl (also 2-methylethenyl) (C$_3$), isopropenyl (also 2-methylethen-2-yl) (C$_3$), prop-2-ynyl (also propargyl) (C$_3$), propyn-1-yl (C$_3$), n-butyl (C$_4$), sec-butyl (C$_4$), iso-butyl (C$_4$), tert-butyl (C$_4$), cyclobutyl (C$_4$), buten-4-yl (C$_4$), cyclopentyl (C$_1$), cyclohexyl (C$_6$);
ii) substituted or unsubstituted C$_6$ or C$_{10}$ aryl; for example, phenyl, naphthyl (also referred to herein as naphthylen-1-yl (C$_{10}$) or naphthylen-2-yl (C$_{10}$));
iii) substituted or unsubstituted C$_6$ or C$_{10}$ alkylenearyl; for example, benzyl, 2-phenylethyl, naphthylen-2-ylmethyl;
iv) substituted or unsubstituted C$_1$-C$_9$ heterocyclic rings; as described herein;
v) substituted or unsubstituted C$_1$-C$_9$ heteroaryl rings; as described herein;
vi) —(CR$^{31a}$R$^{31b}$)$_q$OR$^{30}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
vii) —(CR$^{31a}$R$^{31b}$)$_q$C(O)R$^{30}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;
viii) —(CR$^{31a}$R$^{31b}$)$_q$C(O)R$^{30}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
ix) —(CR$^{31a}$R$^{31b}$)$_q$C(O)N(R$^{30}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;
x) —(CR$^{31a}$R$^{31b}$)$_q$N(R$^{30}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
xi) halogen; —F, —Cl, —Br, and —I;
xii) —(CR$^{31a}$R$^{31b}$)$_q$CN;
xiii) —(CR$^{31a}$R$^{31b}$)$_q$NO$_2$;
xiv) —(CH$_j$X$_k$)$_h$CH$_{j'}$X$_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3$;
xv) —(CR$^{31a}$R$^{31b}$)$_q$SR$^{30}$, SH, —CH$_2$SH, —SCH$_3$, —CH$_2$SCH$_3$, —SC$_6$H$_5$, and —CH$_2$SC$_6$H$_5$;
xvi) —(CR$^{31a}$R$^{31b}$)$_q$SO$_2$R$^{30}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xvii) —(CR$^{31a}$R$^{31b}$)$_q$SO$^{30}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{30}$ is independently hydrogen, substituted or unsubstituted C$_1$-C$_6$ linear, C$_3$-C$_6$ branched, or C$_3$-C$_6$ cyclic alkyl, phenyl, benzyl, heterocyclic, or heteroaryl; or two $R^{30}$ units can be taken together to form a ring comprising 3-7 atoms; $R^{31a}$ and $R^{31b}$ are each independently hydrogen or $C_1$-$C_4$ linear or $C_3$-$C_4$ branched alkyl; the index q is from 0 to 4.

One example of $R^1$ units includes substituted or unsubstituted phenyl ($C_6$ aryl) units, wherein each substitution is independently chosen from: halogen, $C_1$-$C_4$ linear, branched alkyl, or cyclic alkyl, —$OR^{11}$, —CN, —$N(R^{11})_2$, —$CO_2R^{11}$, —$C(O)N(R^{11})_2$, —$NR^{11}C(O)R^{11}$, —$NO_2$, and —$SO_2R^{11}$; each $R^{11}$ is independently hydrogen; substituted or unsubstituted $C_1$-$C_4$ linear, $C_3$-$C_4$ branched, $C_3$-$C_4$ cyclic alkyl, alkenyl, or alkynyl; substituted or unsubstituted phenyl or benzyl; or two $R^{11}$ units can be taken together to form a ring comprising from 3-7 atoms.

An example of $R^1$ units includes substituted $C_6$ aryl units chosen from phenyl, 2-fluorophenyl, 3-fluorophenyl, 4-fluorophenyl, 2,3-difluorophenyl, 3,4-difluorophenyl, difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

An example of $R^1$ units includes substituted or unsubstituted $C_6$ aryl units chosen from 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

An example of $R^1$ units includes substituted $C_6$ aryl units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

An example of $R^1$ units includes substituted $C_6$ aryl units chosen from 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

$R^1$ can comprise heteroaryl units. Non-limiting examples of $C_1$-$C_9$ heteroaryl units include:

i)

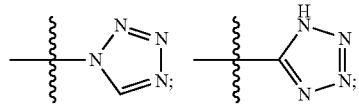

ii)

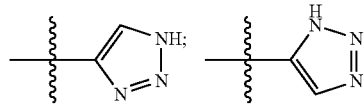

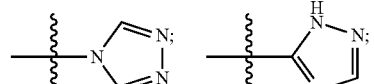

iii)

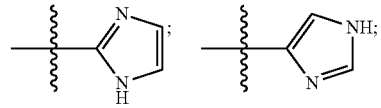

iv)

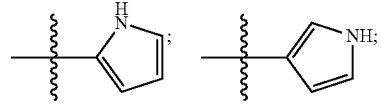

v)

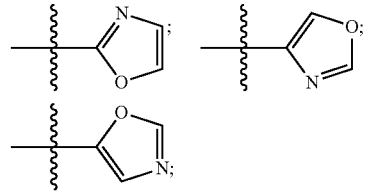

vi)

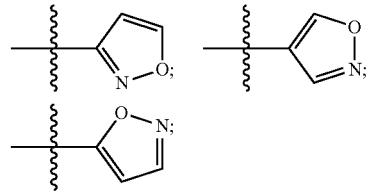

vii)

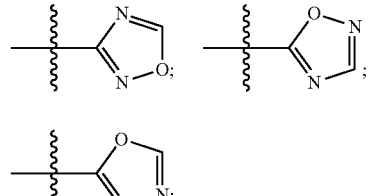

viii)

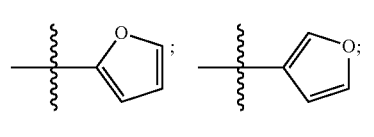

ix)

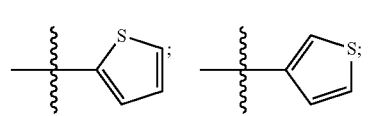

x)

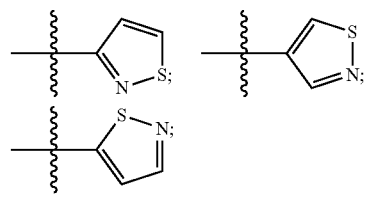

xi)

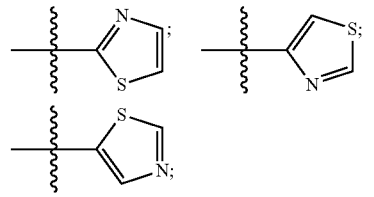

xii)

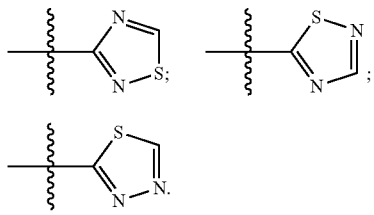

R[1] heteroaryl units can be substituted or unsubstituted. Non-limiting examples of units that can substitute for hydrogen include units chosen from:
  i) $C_1$-$C_6$ linear, $C_3$-$C_6$ branched, and $C_3$-$C_6$ cyclic alkyl;
  ii) substituted or unsubstituted phenyl and benzyl;
  iii) substituted of unsubstituted $C_1$-$C_9$ heteroaryl;
  iv) —C(O)R[9]; and
  v) —NHC(O)R[9];
wherein R[9] is $C_1$-$C_6$ linear and branched alkyl; $C_1$-$C_6$ linear and $C_3$-$C_6$ branched alkoxy; or —NHCH$_2$C(O)R[10]; R[10] is chosen from hydrogen, methyl, ethyl, and tert-butyl.

An example of R[1] relates to units substituted by an alkyl unit chosen from methyl, ethyl, n-propyl, iso-propyl, n-butyl, iso-butyl, sec-butyl, and tert-butyl.

An example of R[1] includes units that are substituted by substituted or unsubstituted phenyl and benzyl, wherein the phenyl and benzyl substitutions are chosen from one or more:
  i) halogen;
  ii) $C_1$-$C_3$ alkyl;
  iii) $C_1$-$C_3$ alkoxy;
  iv) —CO$_2$R[11]; and
  v) —NHCOR[16];
wherein R[11] and R[16] are each independently hydrogen, methyl, or ethyl.

An example of R[1] relates to phenyl and benzyl units substituted by a carboxy unit having the formula —C(O)R[9]; R[9] is chosen from methyl, methoxy, ethyl, and ethoxy.

An example of R[1] includes phenyl and benzyl units substituted by an amide unit having the formula —NHC(O)R[9]; R[9] is chosen from methyl, methoxy, ethyl, ethoxy, tert-butyl, and tert-butoxy.

An example of R[1] includes phenyl and benzyl units substituted by one or more fluoro or chloro units.

L Units

L is a linking unit which is present when the index n is equal to 1, but is absent when the index n is equal to 0. L units have the formula:

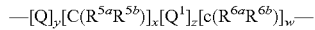

wherein Q and Q[1] are each independently:
  i) —C(O)—;
  ii) —NH—;
  iii) —C(O)NH—;
  iv) —NHC(O)—;
  v) —NHC(O)NH—;
  vi) —NHC(O)O—;
  vii) —C(O)O—;
  viii) —C(O)NHC(O)—;
  ix) —O—;
  x) —S—;
  xi) —SO$_2$—;
  xii) —C(=NH)—;
  xiii) —C(=NH)NH—;
  xiv) —NHC(=NH)—; or
  xv) —NHC(=NH)NH—.

When the index y is equal to 1, Q is present. When the index y is equal to 0, Q is absent. When the index z is equal to 1, Q[1] is present. When the index z is equal to 0, Q[1] is absent.

R[5a] and R[5b] are each independently:
  i) hydrogen;
  ii) hydroxy;
  iii) halogen;
  iv) substituted or unsubstituted $C_1$-$C_6$ linear or $C_3$-$C_6$ branched alkyl; or
  v) a unit having the formula:

—[C(R[7a]R[7b])]$_t$R[8]

wherein R[7a] and R[7b] are each independently:
  i) hydrogen; or
  ii) substituted or unsubstituted $C_1$-$C_6$ linear, $C_3$-$C_6$ branched, or $C_3$-$C_6$ cyclic alkyl.

R[g] is:
  i) hydrogen;
  ii) substituted or unsubstituted $C_1$-$C_6$ linear, $C_3$-$C_6$ branched, or $C_3$-$C_6$ cyclic alkyl;
  iii) substituted or unsubstituted $C_6$ or $C_{10}$ aryl;
  iv) substituted or unsubstituted $C_1$-$C_9$ heteroaryl; or
  v) substituted or unsubstituted $C_1$-$C_9$ heterocyclic.

R[6a] and R[6b] are each independently:
  i) hydrogen; or
  ii) $C_1$-$C_4$ linear or $C_3$-$C_4$ branched alkyl.

The indices t, w and x are each independently from 0 to 4.

The following are non-limiting examples of units that can substitute for one or more hydrogen atoms on R[5a], R[5b], R[7a], R[7b], and R[8] units. The following substituents, as well as others not herein described, are each independently chosen:
  i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
  ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
  iii) substituted or unsubstituted $C_6$ or $C_{10}$ alkylenearyl; for example, benzyl, 2-phenylethyl, naphthylen-2-ylmethyl;
  iv) substituted or unsubstituted $C_1$-$C_9$ heterocyclic rings; as described herein below;
  v) substituted or unsubstituted $C_1$-$C_9$ heteroaryl rings; as described herein below;
  vi) —(CR[41a]R[41b])$_r$OR[40]; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
  vii) —(CR[41a]R[41b])$_r$C(O)R[30]; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;
  viii) —(CR[41a]R[41b])$_r$C(O)R[30]; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
  ix) —(CR[41a]R[41b])$_r$C(O)N(R[40])$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;

x) —(CR$^{41a}$R$^{41b}$)$_r$N(R$^{30}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
xi) halogen; —F, —Cl, —Br, and —I;
xii) —(CR$^{41a}$R$^{41b}$)$_r$CN;
xiii) —(CR$^{41a}$R$^{41b}$)$_r$NO$_2$;
xiv) —(CH$_j$X$_{k'}$)$_h$CH$_{j'}$X$_k$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3$;
xv) —(CR$^{41a}$R$^{41b}$)$_r$SR$^{40}$, SH, —CH$_2$SH, —SCH$_3$, —CH$_2$SCH$_3$, —SC$_6$H$_5$, and —CH$_2$SC$_6$H$_5$;
xvi) —(CR$^{41a}$R$^{41b}$)$_r$SO$_2$R$^{30}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xvii) —(CR$^{41a}$R$^{41b}$)$_r$SO$_3$R$^{40}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{40}$ is independently hydrogen, substituted or unsubstituted C$_1$-C$_6$ linear, C$_3$-C$_6$ branched, or C$_3$-C$_6$ cyclic alkyl, phenyl, benzyl, heterocyclic, or heteroaryl; or two R$^{40}$ units can be taken together to form a ring comprising 3-7 atoms; R$^{41a}$ and R$^{41b}$ are each independently hydrogen or C$_1$-C$_4$ linear or C$_3$-C$_4$ branched alkyl; the index r is from 0 to 4.

One aspect of L units relates to units having the formula:

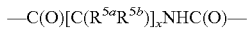

wherein R$^{5a}$ is hydrogen, substituted or unsubstituted C$_1$-C$_4$ alkyl, substituted or unsubstituted phenyl, and substituted or unsubstituted heteroaryl; and the index x is 1 or 2. Some embodiments relate to linking units having the formula:
i) —C(O)[C(R$^{5a}$H)]NHC(O)O—;
ii) —C(O)[C(R$^{5a}$H)][CH$_2$]NHC(O)O—;
ii) —C(O)[CH$_2$][C(R$^{5a}$H)]NHC(O)O—;
iv) —C(O)[C(R$^{5a}$H)]NHC(O)—;
v) —C(O)[C(R$^{5a}$H)][CH$_2$]NHC(O)—; or
vi) —C(O)[CH$_2$][C(R$^{5a}$H)]NHC(O)—;
wherein R$^{5a}$ is:
i) hydrogen;
ii) methyl;
iii) ethyl;
iv) isopropyl;
v) phenyl;
vi) benzyl;
vii) 4-hydroxybenzyl;
viii) hydroxymethyl; or
ix) 1-hydroxyethyl.

When the index x is equal to 1, this embodiment provides the following non-limiting examples of L units:

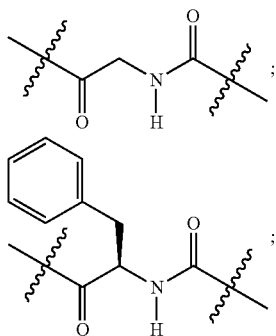

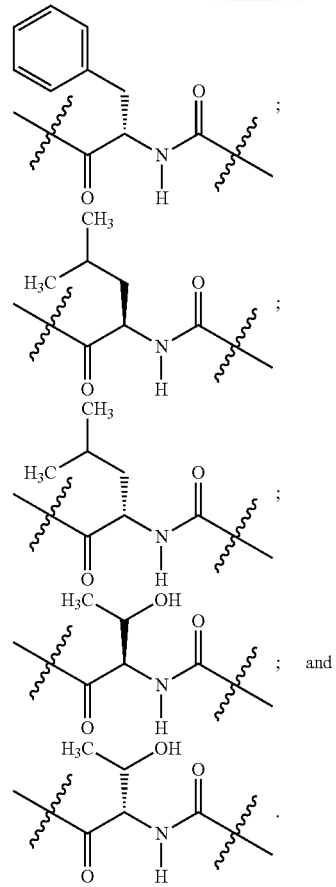

When the index x is equal to 2, this embodiment provides the following non-limiting examples of L units:

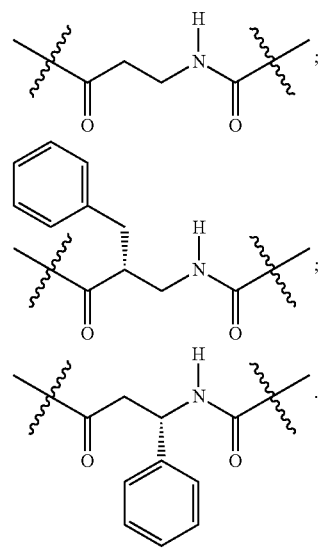

Another embodiment of L units includes units wherein Q is —C(O)—, the indices x and z are equal to 0, w is equal to 1 or 2, a first R$^{6a}$ unit chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl; a second $R^{6'}$ unit is hydrogen and $R^{6b}$ units are hydrogen. For example a linking unit having the formula:

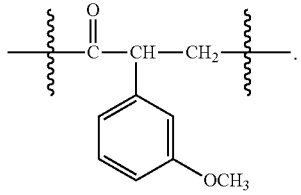 [SMILES: *CC(C(*)=O)c1cccc(OC)c1]

An example of this embodiment of L includes a first $R^{6'}$ unit as depicted herein above that is a substituted or unsubstituted heteroaryl unit as described herein above.

An example of this embodiment of L includes units having the formula:

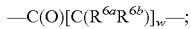

wherein $R^{6a}$ and $R^{6b}$ are hydrogen and the index w is equal to 1 or 2; said units chosen from:
 i) —C(O)CH$_2$—; and
 ii) —C(O)CH$_2$CH$_2$—.

Another embodiment of L units includes units having the formula:

—C(O)[C(R$^{5a}$R$^{5b}$)]$_x$C(O)—;

wherein $R^{5a}$ and $R^{5b}$ are hydrogen and the index x is equal to 1 or 2; said units chosen from:
 i) —C(O)CH$_2$C(O)—; and
 ii) —C(O)CH$_2$CH$_2$C(O)—.

Another embodiment of L units includes units having the formula:

wherein $R^{5a}$ and $R^{5b}$ are hydrogen and the index w is equal to 0, 1 or 2; said units chosen from:
 ii) —C(O)NH—;
 ii) —C(O)NHCH$_2$—; and
 iii) —C(O)NHCH$_2$CH$_2$—.

An example of L units includes units having the formula:

—SO$_2$[C(R$^{6a}$R$^{6b}$)]$_w$—;

wherein $R^{8a}$ and $R^{8b}$ are hydrogen or methyl and the index w is equal to 0, 1 or 2; said units chosen from:
 i) —SO$_2$—;
 ii) —SO$_2$CH$_2$—; and
 iii) —SO$_2$CH$_2$CH$_2$—.

Pharmaceutically-Acceptable Salts.

The present disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt. In some embodiments, a pharmaceutically-acceptable salt is a lithium salt. In some embodiments, a pharmaceutically-acceptable salt is a sodium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a an imidazole salt, or a pyrazine salt.

Acid addition salts can arise from the addition of an acid to a compound of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Disclosed herein are categories of compounds useful for the methods described herein, and pharmaceutically acceptable salt forms thereof. For example, a compound having the formula:

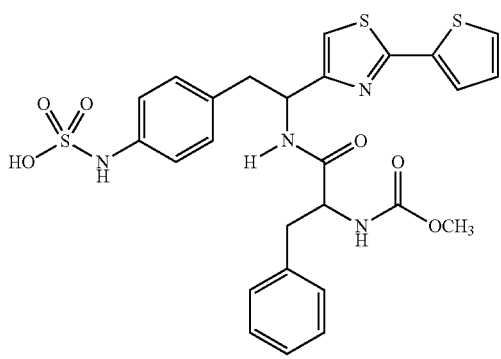 [SMILES: COC(=O)NC(Cc1ccccc1)C(=O)NC(Cc1ccc(NS(=O)(=O)O)cc1)c1csc(-c2cccs2)n1]
can form salts, for example, a salt of the sulfamic acid:
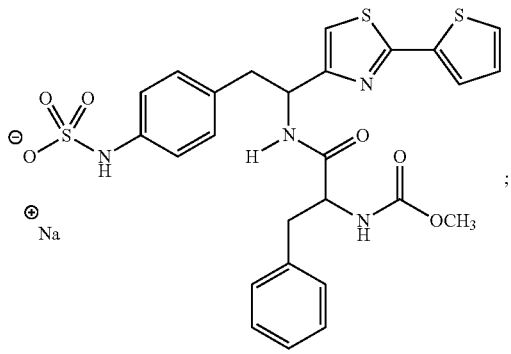
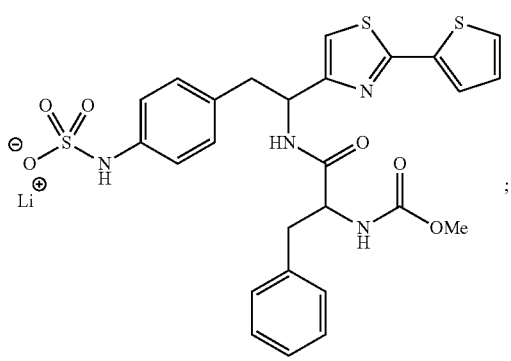
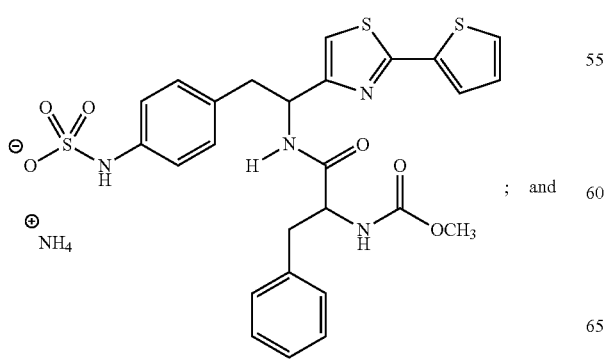
; and
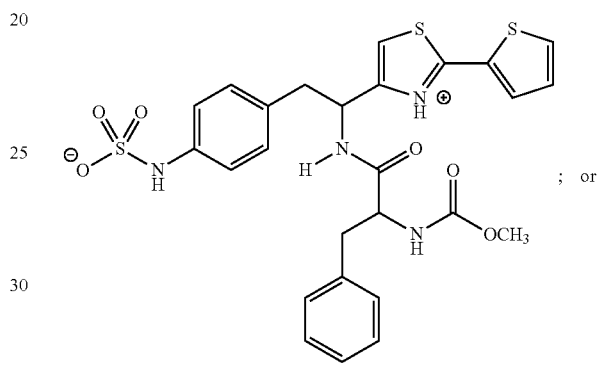
The compounds can also exist in a zwitterionic form, for example:
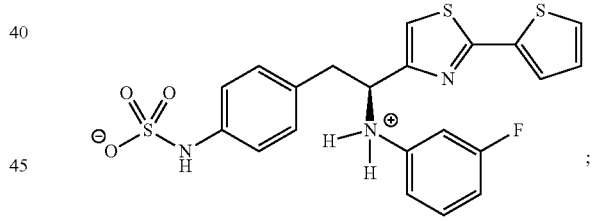
or as a salt of a strong acid, for example:
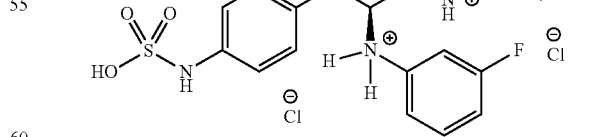
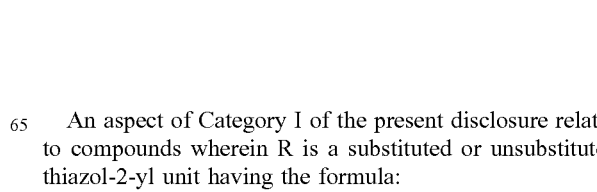
An aspect of Category I of the present disclosure relates to compounds wherein R is a substituted or unsubstituted thiazol-2-yl unit having the formula:

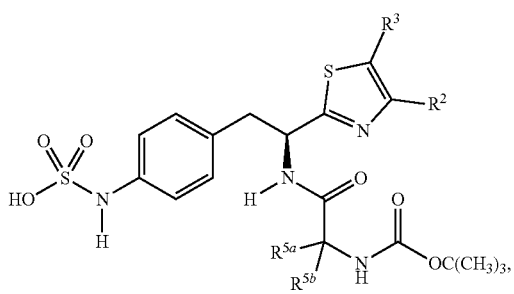

one embodiment of which relates to inhibitors having the formula:

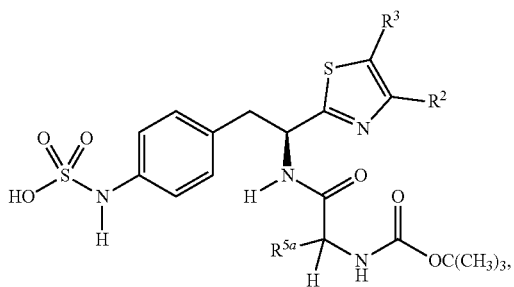

wherein R units are thiazol-2-yl units, that when substituted, are substituted with $R^2$ and $R^3$ units. R and $R^{5a}$ its are further described in Table 1.

TABLE 1

| No. | R | $R^{5a}$ |
|---|---|---|
| A1 | thiazol-2-yl | (S)-benzyl |
| A2 | 4-methylthiazol-2-yl | (S)-benzyl |
| A3 | 4-ethylthiazol-2-yl | (S)-benzyl |
| A4 | 4-propylthiazol-2-yl | (S)-benzyl |
| A5 | 4-iso-propylthiazol-2-yl | (S)-benzyl |
| A6 | 4-cyclopropylthiazol-2-yl | (S)-benzyl |
| A7 | 4-butylthiazol-2-yl | (S)-benzyl |
| A8 | 4-tert-butylthiazol-2-yl | (S)-benzyl |
| A9 | 4-cyclohexylthiazol-2-yl | (S)-benzyl |
| A10 | 4-(2,2,2-trifluoroethyl)thiazol-2-yl | (S)-benzyl |
| A11 | 4-(3,3,3-trifluoropropyl)thiazol-2-yl | (S)-benzyl |
| A12 | 4-(2,2-difluorocyclopropyl)thiazol-2-yl | (S)-benzyl |
| A13 | 4-(methoxymethyl)thiazol-2-yl | (S)-benzyl |
| A14 | 4-(carboxylic acid ethyl ester)thiazol-2-yl | (S)-benzyl |
| A15 | 4,5-dimethylthiazol-2-yl | (S)-benzyl |
| A16 | 4-methyl-5-ethylthiazol-2-yl | (S)-benzyl |
| A17 | 4-phenylthiazol-2-yl | (S)-benzyl |
| A18 | 4-(4-chlorophenyl)thiazol-2-yl | (S)-benzyl |
| A19 | 4-(3,4-dimethylphenyl)thiazol-2-yl | (S)-benzyl |
| A20 | 4-methyl-5-phenylthiazol-2-yl | (S)-benzyl |
| A21 | 4-(thiophen-2-yl)thiazol-2-yl | (S)-benzyl |
| A22 | 4-(thiophen-3-yl)thiazol-2-yl | (S)-benzyl |
| A23 | 4-(5-chlorothiophen-2-yl)thiazol-2-yl | (S)-benzyl |
| A24 | 5,6-dihydro-4H-cyclopenta[d]thiazol-2-yl | (S)-benzyl |
| A25 | 4,5,6,7-tetrahydrobenzo[d]thiazol-2-yl | (S)-benzyl |

In some embodiments, a compound of the disclosure is selected from one of TABLE 1, or a pharmaceutically acceptable salt thereof.

Pharmaceutical Compositions.

A pharmaceutical composition of the disclosure can provide a therapeutically-effective amount of an inhibitor of HPTPβ. A pharmaceutical composition of the disclosure can provide a therapeutically-effective amount of a Tie-2 modulator.

A pharmaceutical composition of the disclosure can be a combination of any pharmaceutical compounds described herein with other chemical components, such as carriers, stabilizers, diluents, dispersing agents, suspending agents, thickening agents, solubilizing agents, or excipients. The pharmaceutical composition facilitates administration of the compound to an organism. Pharmaceutical compositions can be administered in therapeutically-effective amounts as pharmaceutical compositions by various forms and routes including, for example, intravenous, intravitreal, subcutaneous, intramuscular, oral, rectal, aerosol, parenteral, ophthalmic, pulmonary, transdermal, vaginal, otic, nasal, intraocular, and topical administration. In some embodiments, a pharmaceutical composition of the disclosure can be administered topical to the eye of a subject. In some embodiments, a subject can self-administer a pharmaceutical composition of the disclosure.

In some embodiments, a compound disclosed herein is present in a pharmaceutical composition in an amount of from about 0.1 mg/mL to about 300 mg/mL, from about 30 mg/mL to about 300 mg/mL, from about 0.1 mg/mL to about 1 mg/mL, from about 0.1 mg/mL to about 5 mg/mL, from about 1 mg/mL to about 50 mg/mL, from about 5 mg/mL to about 10 mg/mL, from about 10 mg/mL to about 15 mg/mL, from about 10 mg/mL to about 120 mg/L, from about 15 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, from about 95 mg/mL to about 100 mg/mL, from about 100 mg/mL to about 110 mg/mL, from about 110 mg/mL to about 120 mg/mL, from about 120 mg/mL to about 130 mg/mL, from about 130 mg/mL to about 140 mg/mL, from about 140 mg/mL to about 150 mg/mL, from about 150 mg/mL to about 160 mg/mL, from about 160 mg/mL to about 170 mg/mL, from about 170 mg/mL to about 180 mg/mL, from about 180 mg/mL to about 190 mg/mL, from about 190 mg/mL to about 200 mg/mL, from about 200 mg/mL to about 220 mg/mL, from about 220 mg/mL to about 240 mg/mL, from about 240 mg/mL to about 260 mg/mL, from about 260 mg/mL to about 280 mg/mL, or from about 280 mg/mL to about 300 mg/mL.

In some embodiments, a compound disclosed herein is present in a pharmaceutical composition in an amount of from about 0.1 mg/mL to about 100 mg/mL, from about 0.1 mg/mL to about 1 mg/mL, from about 0.1 mg/mL to about 5 mg/mL, from about 5 mg/mL to about 10 mg/mL, from about 10 mg/mL to about 15 mg/mL, from about 15 mg/mL to about 20 mg/mL, from about 20 mg/mL to about 25 mg/mL, from about 25 mg/mL to about 30 mg/mL, from about 30 mg/mL to about 35 mg/mL, from about 30 mg/mL to about 50 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, or from about 95 mg/mL to about 100 mg/mL. In some embodiments, a Tie-2 activator or a pharmaceutically-acceptable salt thereof is present in a pharmaceutical composition at a concentration of at least about 30 mg/mL.

In some embodiments, a compound disclosed herein is present in a pharmaceutical composition in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

In some embodiments, a a compound disclosed herein is present in a pharmaceutical composition or a unit dosage form in an amount of about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 30 mg to about 50 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

In some embodiments, a Tie-2 modulator or pharmaceutically-acceptable salt thereof is present in a pharmaceutical composition or a unit dosage form in an amount of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

Any compound herein can be purified. A compound herein, such as a Tie-2 modulator, can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

A pharmaceutical composition disclosed herein can be stable for about 1 day, about 2 days, about 3 days, about 4 days, about 5 days, about 6 days, about 7 days, about 8 days, about 9 days, about 10 days, about 15 days, about 20 days, about 25 days, about 30 days, about 35 days, about 40 days, about 45 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

A pharmaceutical composition disclosed herein can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically-acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, granulating, dragee-making, levigating, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions, and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the present disclosure include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

The disclosure can be administered in a unit dosage form, such as, for example, as an eye drop. The average volume of each drop administered to a subject can be about 0.1 µl, about 0.2 µl, about 0.3 µl, about 0.4 µl, about 0.5 µl, about 0.6 µl, about 0.7 µl, about 0.8 µl, about 0.9 µl, about 1 µl, about 2 µl, about 3 µl, about 4 µl, about 5 µl, about 5 µl, about 10 µl, about 15 µl, about 20 µl, about 30 µl, about 40 µl, about 50 µl, about 60 µl, about 70 µl, about 80 µl, about or about 100 µl. The unit dosage form (e.g. eye drops) can contain about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of a compound of the disclosure by mass. The unit dosage form, such as, for example, an eye drop, can contain about from about 0.01% to about 20% of a compound of the disclosure by mass, such as from about 0.01% to about 15%, from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.5% to about 5%, from about 1% to about 15%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 5%, from about 3% to about 5%, or from about 2% to about 6% of a compound of the disclosure by mass.

The unit dosage form, such as, for example, an eye drop, can contain about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL, about 100 mg/mL, about 120 mg/mL, about 140 mg/mL, about 160 mg/mL, about 180 mg/mL, or about 200 mg/mL of a compound of the disclosure.

The individual dose administered to a subject, in, for example, an eye drop, can be about 0.5 µg, about 1 µg, about 2 µg, about 3 µg, about 4 µg, about 5 µg, about 6 µg, about 7 µg, about 8 µg, about 9 µg, about 10 µg, about 20 µg, about 30 µg, about 40 µg, about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1 mg, about 1.1 mg, about 1.2 mg, 1.3 mg, about 1.4 mg, about 1.5 mg, about 1.6 mg, about 1.7 mg, about 1.8 mg, about 1.9 mg, or about 2 mg of a compound of the disclosure. In some embodiments, more than one drop can be administered to an eye either at one time or at multiple times throughout the day.

Non-limiting examples of excipients suitable for use in a formulation described herein include cyclodextrin, α-cyclodextrin, O-cyclodextrin, 2-hydroxypropyl-β-cyclodextrin (HP-β-CD), random methyl-β-cyclodextrin (RM-β-CD), sulfobutyl ether β-cyclodextrin (SBE-β-CD), γ-cyclodextrin, hydroxypropyl-γ-cyclodextrin (HP-γ-CD), hydroxyethyl-β-cyclodextrin (HE-β-CD), heptakis (2,6-di-O-methyl)-β-cyclodextrin (DMβCD), saline, sodium bisulfate, metabisulfate, ascorbic acid, acetylcysteine, benzalkonium chloride, boric acid, hyaluronic acid, hypromellose, propylene glycol, potassium sorbate, sodium chloride, sodium acetate, disodium edetate, sodium dihydrogen phosphate monohydrate, disodium phosphate, sodium hydroxide, hydrochloric acid, glycerol, mannitol, trometamol, tyloxapol, surfactants, and any combination thereof.

The individual dose administered to a subject can be about 0.5 mg, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, or about 500 mg of a compound of the present disclosure. The individual dose administered to a subject can be from about 0.1 mg to about 25 mg, about 0.1 mg to about 50 mg, about 0.1 mg to about 75 mg, or about 0.1 mg to about 100 mg. The individual dose administered to a subject can be from about 0.5 mg to about 10 mg, about 0.5 mg to about 20 mg, or about 0.5 mg to about 30 mg. In some embodiments, the individual dose administered to a subject can be about 10 mg of a compound of the present disclosure. In some embodiments, the individual dose administered to a subject can be about 15 mg of a compound of the present disclosure. In some embodiments, the individual dose administered to a subject can be about 20 mg of a compound of the present disclosure. In some embodiments, the individual dose administered to a subject can be about 30 mg of a compound of the present disclosure. In some embodiments, the individual dose of a compound of the present disclosure administered to a subject can be about 15 mg twice per day or about 30 mg per day.

Non-limiting examples of pharmaceutically-acceptable excipients suitable for use in the present disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, anti-microbial agents, plant cellulosic material and spheronization agents, and any combination thereof.

A composition of the present disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 2% weight by volume pharmaceutically-acceptable preservatives. In some embodiments, the preservative is an alcohol, such as, for example, ethanol, 2-phenylethanol or benzyl alcohol.

In some embodiments, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of an HPTPβ inhibitor, or a pharmaceutically-acceptable salt thereof, in combination with a pharmaceutically-acceptable carrier. The carrier can be selected to minimize any degradation of the active ingredient and to minimize any adverse side effects in the subject.

The disclosed methods include administration of a Tie-2 activator, or a pharmaceutically-acceptable salt thereof, in combination with a pharmaceutically-acceptable carrier. The carrier can be selected to minimize any degradation of the active ingredient and to minimize any adverse side effects in the subject.

The compound or a pharmaceutically-acceptable salt thereof herein can be conveniently formulated into pharmaceutical compositions composed of one or more pharmaceutically-acceptable carriers. See e.g., *Remington's Pharmaceutical Sciences*, latest edition, by E. W. Martin Mack Pub. Co., Easton, PA, which discloses typical carriers, including fluid carriers, and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as sterile water, saline, and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable liquid carriers include water, saline solution, Ringer's solution, glycerol, ethanol, and dextrose solution. The pH of the solution can be from about 5 to about 8, and can be from about 7 to about 7.5. Further carriers include sustained release preparations such as semipermeable matrices of solid hydrophobic polymers containing the compound or a pharmaceutically-acceptable salt thereof, where the matrices are in the form of shaped articles, such as films, liposomes, microparticles, and microcapsules.

The disclosed methods relate to administering the compound or a pharmaceutically-acceptable salt thereof as part of a pharmaceutical composition. The disclosed methods relate to administering the HPTPβ inhibitor or a pharmaceutically-acceptable salt thereof as part of a pharmaceutical composition. In various embodiments, compositions of the present disclosure can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, or anesthetics.

An excipient can fill a role as simple and direct as being an inert filler, or an excipient as used herein can be part of a pH stabilizing system or coating to ensure delivery of the ingredients safely to the stomach.

The Tie-2 modulator or a pharmaceutically-acceptable salt thereof can also be present in liquids, emulsions, or suspensions for delivery of active therapeutic agents in aerosol form to cavities of the body such as the nose, throat, or bronchial passages. The ratio of Tie-2 modulator or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, for example, in unit dosage form suitable for single administration of a precise dosage. The compositions can contain, as noted above, an effective amount of the Tie-2 activator or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate. In one embodiment, a composition comprising the Tie-2 activator or a pharmaceutically-acceptable salt thereof in an amount of approximately 4 mg per 0.1 mL liquid is prepared. The liquid phase comprises sterile water and an appropriate amount of a saccharide or polysaccharide.

Pharmaceutical compositions containing the compounds described herein can be administered for prophylactic or therapeutic treatments. Compositions can contain any number of active agents. In therapeutic applications, the compositions can be administered to a subject already suffering from a disease or condition, in an amount sufficient to cure or at least partially arrest the symptoms of the disease or condition, or to cure, heal, improve, reduce, lessen, ameliorate, or reduce a likelihood the disease or condition. Compounds can also be administered to lessen or reduce a likelihood of developing, contracting, or worsening a condition. Amounts effective for this use can vary based on the severity and course of the disease or condition, previous therapy, the subject's health status, weight, response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills or injections. The compounds can be packed together or separately, in a single package or in a plurality of packages. One or all of the therapeutic agents can be given in multiple doses. If not simultaneous, then the timing between the multiple doses can vary.

Compounds and compositions described herein can be packaged as a kit. In some embodiments, the present disclosure provides a kit comprising a compound disclosed herein, or a pharmaceutically-acceptable salt thereof, and written instructions on use of the kit in the treatment of a condition described herein. In some embodiments, the present disclosure provides a kit comprising a compound disclosed herein, or a pharmaceutically-acceptable salt thereof, an antibody, and written instructions on use of the kit in the treatment of a condition described herein.

The compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to lessen or reduce a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Solubilizing Agents.

A Tie-2 modulator described herein can be present in a composition with one or more solubilizing and preservative agents. The concentration of a solubilizing agent or additive in a pharmaceutical composition of the disclosure can be from about 0.1 mg/mL to about 300 mg/mL, from about 0.1 mg/mL to about 1 mg/mL, from about 0.1 mg/mL to about 5 mg/mL, from about 1 mg/mL to about 50 mg/mL, from about 5 mg/mL to about 10 mg/mL, from about 10 mg/mL to about 15 mg/mL, from about 15 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, from about 95 mg/mL to about 100 mg/mL, from about 100 mg/mL to about 110 mg/mL, from about 110 mg/mL to about 120 mg/mL, from about 120 mg/mL to about 130 mg/mL, from about 130 mg/mL to about 140 mg/mL, from about 140 mg/mL to about 150 mg/mL, from about 150 mg/mL to about 160 mg/mL, from about 160 mg/mL to about 170 mg/mL, from about 170 mg/mL to about 180 mg/mL, from about 180 mg/mL to about 190 mg/mL, from about 190 mg/mL to about 200 mg/mL, from about 200 mg/mL to about 220 mg/mL, from about 220 mg/mL to about 240 mg/mL, from about 240 mg/mL to about 260 mg/mL, from about 260 mg/mL to about 280 mg/mL, or from about 280 mg/mL to about 300 mg/mL.

In some embodiments, a Tie-2 modulator of the disclosure has a solubility in a pharmaceutical composition of at least about 10 mg/mL, such as from about 10 mg/mL to about 120 mg/mL, from about 30 mg/mL to about 35 mg/mL, from about 30 mg/mL to about 200 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, from about 95 mg/mL to about 100 mg/mL, from about 100 mg/mL to about 110 mg/mL, from about 110 mg/mL to about 120 mg/mL, from about 120 mg/mL to about 130 mg/mL, from about 130 mg/mL to about 140 mg/mL, from about 140 mg/mL to about 150 mg/mL, from about 150 mg/mL to about 160 mg/mL, from about 160 mg/mL to about 170 mg/mL, from about 170 mg/mL to about 180 mg/mL, from about 180 mg/mL to about 190 mg/mL, from about 190 mg/mL to about 200 mg/mL, from about 200 mg/mL to about 220 mg/mL, from about 220 mg/mL to about 240 mg/mL, from about 240 mg/mL to about 260 mg/mL, from about 260 mg/mL to about 280 mg/mL, or from about 280 mg/mL to about 300 mg/mL.

In some embodiments, a Tie-2 modulator of the disclosure has a solubility in a pharmaceutical composition of at least about 30 mg/mL, such as, for example, at least about 40 mg/mL, at least about 50 mg/mL, at least about 60 mg/mL, at least about 70 mg/mL, at least about 80 mg/mL, at least about 90 mg/mL, or at least about 100 mg/mL.

The solubility of a compound of the disclosure may be increased by addition of an additive or agent to a composition containing the compound. A solubilizing agent can increase the solubility of a compound of the disclosure by about 1%, about 2%, about 3%, about 4%, 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

In some embodiments, a composition disclosed herein can comprise a ratio of about 20 parts of a compound herein or a pharmaceutically-acceptable salt thereof to about 1 part solubilizing agent (about 20:about 1), to about 1 part of the compound herein or a pharmaceutically-acceptable salt thereof to about 20 parts solubilizing system (about 1:about 20). For example, a formulation containing about 100 mg of a compound herein or a pharmaceutically-acceptable salt thereof can contain from about 5 mg to about 2000 mg of a solubilizing agent. In another embodiment, the ratio can be based on number, or moles, or compound compared to number, or moles, of the solubilizing system.

The following are non-limiting examples of ratios of a compound herein and a solubilizing agent. The following examples alternatively describe the weight ratio of a solubilizing agent, such as a cyclodextrin, and a compound herein. The ratio can be:about 20:about 1; about 19.9:about 1; about 19.8:about 1; about 19.7:about 1; about 19.6:about 1; about 19.5:about 1; about 19.4:about 1; about 19.3:about 1; about 19.2:about 1; about 19.1:about 1; about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7: about 1; about 17.6:about 1; about 17.5:about 1; about 17.4:about 1; about 17.3:about 1; about 17.2:about 1; about 17.1:about 1; about 17:about 1; about 16.9:about 1; about 16.8: about 1; about 16.7:about 1; about 16.6:about 1; about 16.5:about 1; about 16.4:about 1; about 16.3:about 1; about 16.2:about 1; about 16.1:about 1; about 16:about 1; about 15.9: about 1; about 15.8:about 1; about 15.7:about 1; about 15.6:about 1; about 15.5:about 1; about 15.4:about 1; about 15.3:about 1; about 15.2:about 1; about 15.1:about 1; about 15: about 1; about 14.9:about 1; about 14.8:about 1; about 14.7:about 1; about 14.6:about 1; about 14.5:about 1; about 14.4:about 1; about 14.3:about 1; about 14.2:about 1; about 14.1: about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8:about 1; about 12.7: about 1; about 12.6:about 1; about 12.5:about 1; about 12.4:about 1; about 12.3:about 1; about 12.2 about 1; about 12.1:about 1; about 12:about 1; about 11.9:about 1; about 11.8 about 1; about 11.7:about 1; about 11.6:about 1; about 11.5:about 1; about 11.4:about 1; about 11.3:about 1; about 11.2:about 1; about 11.1:about 1; about 11:about 1; about 10.9: about 1; about 10.8:about 1; about 10.7 about 1; about 10.6 about 1; about 10.5 about 1; about 10.4:about 1; about 10.3:about 1; about 10.2:about 1; about 10.1:about 1; about 10: about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1: about 1; about 7:about 1; about 6.9:about 1; about 6.8:about 1; about 6.7:about 1; about 6.6: about 1; about 6.5:about 1; about 6.4:about 1; about 6.3: about 1; about 6.2:about 1; about 6.1:about 1; about 6:about 1; about 5.9:about 1; about 5.8:about 1; about 5.7:about 1; about 5.6:about 1; about 5.5:about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2: about 1; about 3.1:about 1; about 3:about 1; about 2.9:about 1; about 2.8:about 1; about 2.7: about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

Cyclodextrins.

Non-limiting examples of cyclodextrins include 3-cyclodextrin, methyl 3-cyclodextrin, 2-hydroxypropyl-β-cyclodextrin (HPβCD), sulfobutyl ether-β-cyclodextrin sodium salt, hydroxyethyl-β-cyclodextrin (HE-β-CD), heptakis (2,6-di-O-methyl)-β-cyclodextrin (DMβCD), 2-hydroxypropyl-β-cyclodextrin, α-cyclodextrin, γ-cyclodextrin, 2-hydroxypropyl-γ-cyclodextrin (HPγCD), and sulfobutylether-β-cyclodextrin (SBECD) sodium salt. A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in the formation of a complex stabilized by non-covalent hydrophobic interactions. The complex can be soluble in water, and carry the captured hydrophobic molecule into the bulk solvent.

Compositions of the disclosure can comprise randomly methylated 3-cyclodextrins (RAMEB or RMCD). The compositions of the disclosure can comprise RAMEB comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 methyl groups.

The disclosed solubilizing systems comprise 2-hydroxypropyl-beta-cyclodextrin (HPβCD). 2-Hydroxypropyl-3-cyclodextrin [CAS No. 128446-35-5] is commercially available as Cavitron™. 2-Hydroxypropyl-β-cyclodextrin, also described known as hydroxypropyl-β-cyclodextrin, 2-hydroxypropyl-beta-cyclodextrin, hydroxypropyl-beta-cyclodextrin or HPβCD, can be represented by either of the following formulae:

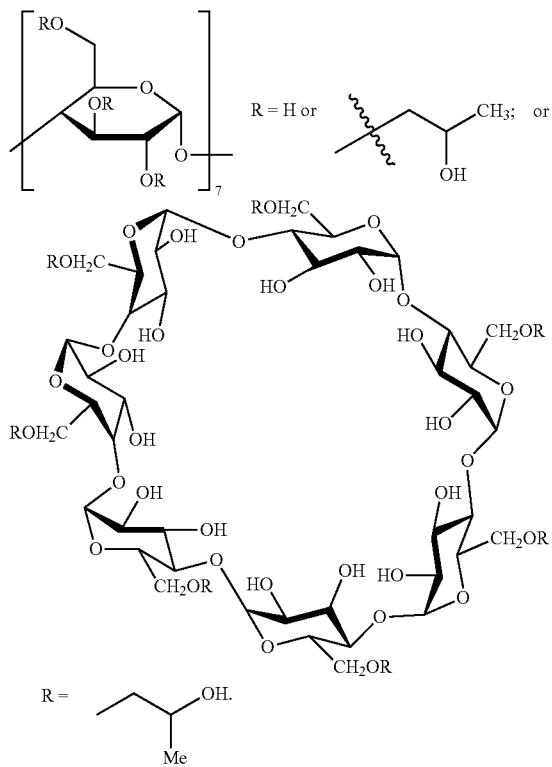

The average molecular weight of Cavitron™, is approximately 1396 Da, wherein the average degree of substitution is from about 0.5 to about 1.3 units of 2-hydroxypropyl per ring glucose unit.

Polyvinylpyrrolidones.

Another non-limiting example of a solubilizing agent is polyvinylpyrrolidone (PVP), having the formula:

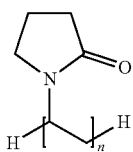

wherein the index n is from about 40 to about 200. PVP's can have an average molecular weight from about 5500 to about 28,000 g/mol. One non-limiting example is PVP-10, having an average molecular weight of approximately 10,000 g/mol. Other non-limiting examples include povidone K12, povidone K25, povidone K27, povidone K29/32, povidone K30, and povidone K90. In some embodiments, the solubilizing agent can be a copolymer, such as a block copolymer comprising povidone and vinyl acetate monomers. One non-limiting example is copovidone K25-31, a copolymer of 1-vinyl-2-pyrrolidone and vinyl acetate in the mass proportion of 3:2 with an average molecular weight of 40000.

Polyakyleneoxides and Ethers Thereof.

Another non-limiting example of solubilizing agents includes polyalkyleneoxides, and polymers of alcohols or polyols. Polymers can be mixed, or contain a single monomeric repeat subunit.

Polyethylene Glycols.

A polyalkyleneoxide of the disclosure can be a polyethylene glycol of the following formula:

HO[CH$_2$CH$_2$O]$_x$H where x represents the average number of ethylene oxide units in the polymer.

For example, polyethylene glycols can have an average molecular weight of from about 200 to about 20,000, for example, PEG 200, PEG 400, PEG 600, PEG 1000, PEG 1450, PEG 1500, PEG 4000, PEG 4600, and PEG 8000. In a same embodiment, a composition comprises one or more polyethylene glycols chosen from PEG 400, PEG 1000, PEG 1450, PEG 4600 and PEG 8000.

Sorbitan Derivatives.

In some embodiments, the solubilizing agent can be a sorbitan derivative, such as a sorbitan ester or polysorbate. A sorbitan ester can be, for example, sorbitan monostearate, sorbitan tristearate, sorbitan monolaurate, sorbitan monooleate, and sorbitan monopalmitate. In some embodiments, the solubilizing agent is a polysorbate, which can include polyethoxylated derivates of sorbitan that are esterified with fatty acids, such as polysorbate 20, polysorbate 40, polysorbate 60, polysorbate 65, and polysorbate 80, as well as PEG-20 sorbitan isostearate and PEG-40 sorbitan diisostearate. In an exemplary embodiment, the solubilizing agent comprises Polysorbate 80 (Tween™ 80), which is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecanoate poly(oxy-1,2-ethandiyl) derivatives.

Polypropylene glycols.

Other polyalkyleneoxides are polypropylene glycols having the formula:

HO[CH(CH$_3$)CH$_2$O]$_x$H wherein the index x represents the average number of propyleneoxy units in the polymer. The index x can be represented by a whole number or a fraction. For example, a polypropylene glycol having an average molecular weight of 8,000 g/mole (PPG 8000) can be represented by the formulae:

HO[CH(CH$_3$)CH$_2$O]$_{138}$H or HO[CH(CH$_3$)CH$_2$O]$_{137.6}$H or the polypropylene glycol can be represented by the common, short hand notation: PPG 8000.

Another example of polypropylene glycols can have an average molecular weight from about 1200 g/mol to about 20,000 g/mol, i.e., a polypropylene glycol having an average molecular weight of about 8,000 g/mol, for example, PPG 8000.

Solubilizing agents also include poloxamers having the formula:

HO(CH$_2$CH$_2$)$_{y1}$(CH$_2$CH$_2$CH$_2$O)$_{y2}$(CH$_2$CH$_2$O)$_{y3}$OH which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. Such solubilizing agents can include, for example, poloxamer 124, poloxamer 182, poloxamer 188, poloxamer 331, or poloxamer 407, including those listed in the Inactive Ingredient Guide prepared by the U.S. Food and Drug Administration.

Alcohols.

A non-limiting example of a solubilizing agent includes an organic solvent. Non-limiting examples of organic solvents include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, benzyl alcohol, and 2-phenylethanol.

Treatment of Subjects with a Tie-2 Activator.

The present disclosure provides methods for treating a subject afflicted with vascular disorders with an activator of Tie-2 or an inhibitor of HPTPβ. The subject can be a human. Treatment can include treating a human in a clinical trial. A treatment can comprise administering to a subject a pharmaceutical composition comprising one or more of the activators of Tie-2 described throughout the disclosure. A treatment can comprise administrating to a subject a therapy that promotes the phosphorylation of a Tie-2 molecule.

The present disclosure provides methods for treating a subject afflicted with vascular disorders with a therapeutically-effective amount of an activator of Tie-2 or an inhibitor of HPTPβ. The subject can be a human. Treatment can include treating a human in a clinical trial. A treatment can comprise administering to a subject a pharmaceutical composition comprising one or more of the activators of Tie-2 described throughout the disclosure. A treatment can comprise administering to a subject a therapy that promotes the phosphorylation of a Tie-2 molecule. A therapeutically-effective amount can be, for example, from about 0.1 mg to about 100 mg or from about 0.5 mg to about 30 mg.

Non-limiting examples of possible subjects for administration include the following. Subjects can be humans, non-human primates such as chimpanzees, and other apes and monkey species; farm animals such as cattle, horses, sheep, goats, and swine; domestic animals such as rabbits, dogs, and cats; and laboratory animals including rats, mice, and guinea pigs. A subject can be of any age. Subjects can be, for example, elderly adults, adults, adolescents, pre-adolescents, children, toddlers, and infants.

A subject described herein can express Ang1. A subject described herein can express Ang2. A subject described herein can express both Ang1 and Ang2.

Some conditions can lead to an increase in the levels of Ang-2, altering the ratio of Ang-1/Ang-2 in circulation. In some embodiments, a therapy can improve the outcome of a disease state by altering the ratio of Ang-1/Ang-2 in circulation. A therapy can provide an Ang-1/Ang-2 ratio or an Ang-2/Ang-1 ratio of about 1:about 1, about 2:about 1, about 3:about 1, about 4: about 1, about 5:about 1, about 6:about 1, about 7:about 1, about 8:about 1, about 9:about 1, or about 10:about 1.

Subjects suffering from diabetic eye disease, such as non-proliferative diabetic retinopathy (NPDR), can be evaluated for treatment with a compound of the disclosure on the basis of the Diabetic Retinopathy Severity Scale (DRSS), as described in *Ophthalmology*. 1991; 98(5 Suppl):786-806, which is incorporated by reference herein in its entirety. In some embodiments, a subject has a DRSS score from about 40 to about 56, from about 41 to about 55, from about 42 to about 54, from about 43 to about 53.

In some embodiments, a subject does not suffer from central involved diabetic macular edema.

A subject can be evaluated for treatment with a compound of the disclosure on the basis of intraocular pressure. In some embodiments, an eye of a subject has an intraocular pressure that is no more than about 40 mmHg, no more than about 39 mmHg, no more than about 38 mmHg, no more than about 37 mmHg, no more than about 36 mmHg, no more than about 35 mmHg, no more than about 34 mmHg, no more than about 33 mmHg, no more than about 32 mmHg, no more than about 31 mmHg, no more than about 30 mmHg, no more than about 29 mmHg, no more than about 28 mmHg, no more than about 27 mmHg, no more than about 26 mmHg, or no more than about 25 mmHg.

Intraocular Pressure and Outflow Facility.

Administration of a Tie-2 activator disclosed herein to a subject can reduce the intraocular pressure in the subject by, for example, about 0.1 mmHg, about 0.2 mmHg, about 0.3 mmHg, about 0.4 mmHg, about 0.5 mmHg, about 0.6 mmHg, about 0.7 mmHg, about 0.8 mmHg, about 0.9 mmHg, about 1 mmHg, about 1.1 mmHg, about 1.2 mmHg, about 1.3 mmHg, about 1.4 mmHg, about 1.5 mmHg, about 1.6 mmHg, about 1.7 mmHg, about 1.8 mmHg, about 1.9 mmHg, about 2 mmHg, about 2.1 mmHg, about 2.2 mmHg, about 2.3 mmHg, about 2.4 mmHg, about 2.5 mmHg, about 2.6 mmHg, about 2.7 mmHg, about 2.8 mmHg, about 2.9 mmHg, about 3 mmHg, about 3.1 mmHg, about 3.2 mmHg, about 3.3 mmHg, about 3.4 mmHg, about 3.5 mmHg, about 3.6 mmHg, about 3.7 mmHg, about 3.8 mmHg, about 3.9 mmHg, about 4 mmHg, about 4.1 mmHg, about 4.2 mmHg, about 4.3 mmHg, about 4.4 mmHg, about 4.5 mmHg, about 4.6 mmHg, about 4.7 mmHg, about 4.8 mmHg, about 4.9 mmHg, about 5 mmHg, about 5.1 mmHg, about 5.2 mmHg, about 5.3 mmHg, about 5.4 mmHg, about 5.5 mmHg, about 5.6 mmHg, about 5.7 mmHg, about 5.8 mmHg, about 5.9 mmHg, about 6 mmHg, about 6.1 mmHg, about 6.2 mmHg, about 6.3 mmHg, about 6.4 mmHg, about 6.5 mmHg, about 6.6 mmHg, about 6.7 mmHg, about 6.8 mmHg, about 6.9 mmHg, about 7 mmHg, about 7.1 mmHg, about 7.2 mmHg, about 7.3 mmHg, about 7.4 mmHg, about 7.5 mmHg, about 7.6 mmHg, about 7.7 mmHg, about 7.8 mmHg, about 7.9 mmHg, about 8 mmHg, about 8.1 mmHg, about 8.2 mmHg, about 8.3 mmHg, about 8.4 mmHg, about 8.5 mmHg, about 8.6 mmHg, about 8.7 mmHg, about 8.8 mmHg, about 8.9 mmHg, about 9 mmHg, about 9.1 mmHg, about 9.2 mmHg, about 9.3 mmHg, about 9.4 mmHg, about 9.5 mmHg, about 9.6 mmHg, about 9.7 mmHg, about 9.8 mmHg, about 9.9 mmHg, about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, or about 20 mmHg.

Administration of a Tie-2 activator disclosed herein to a subject can reduce the intraocular pressure in the subject by, for example, about 0.1 mmHg to about 20 mmHg, by about 0.1 mmHg to about 15 mmHg, by about 0.1 mmHg to about 10 mmHg, by about 0.1 mmHg to about 9 mmHg, by about 0.1 mmHg to about 8 mmHg, by about 0.1 mmHg to about 7 mmHg, by about 0.1 mmHg to about 6 mmHg, by about 0.1 mmHg to about 5 mmHg, by about 0.1 mmHg to about 4 mmHg, by about 0.1 mmHg to about 3 mmHg, by about 0.1 mmHg to about 2 mmHg, by about 0.1 mmHg to about 1 mmHg, by about 0.5 mmHg to about 20 mmHg, by about 0.5 mmHg to about 15 mmHg, by about 0.5 mmHg to about 10 mmHg, by about 0.5 mmHg to about 9 mmHg, by about 0.5 mmHg to about 8 mmHg, by about 0.5 mmHg to about 7 mmHg, by about 0.5 mmHg to about 6 mmHg, by about 0.5 mmHg to about 5 mmHg, by about 0.5 mmHg to about 4 mmHg, by about 0.5 mmHg to about 3 mmHg, by about 0.5 mmHg to about 2 mmHg, by about 0.5 mmHg to about 1 mmHg, by about 1 mmHg to about 20 mmHg, by about 1 mmHg to about 15 mmHg, by about 1 mmHg to about 10 mmHg, by about 1 mmHg to about 9 mmHg, by about 1 mmHg to about 8 mmHg, by about 1 mmHg to about 7 mmHg, by about 1 mmHg to about 6 mmHg, by about 1 mmHg to about 5 mmHg, by about 1 mmHg to about 4 mmHg, by about 1 mmHg to about 3 mmHg, or by about 1 mmHg to about 2 mmHg.

Intraocular pressure in a subject can be measured by, for example, applanation tonometry, dynamic contour tonometry, impression tonometry, pneumatonometry, rebound tonometry, electronic indentation tonometry, or transpalpebral tonometry.

In some embodiments, the present disclosure provides a method for modulating fluid outflow facility in an eye of a subject in need thereof by administering a therapeutically-effective amount of a Tie-2 activator, wherein administration of the Tie-2 activator in the subject modulates the fluid outflow facility by at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, or at least about 50%, as compared to the absence of administration. In some embodiments, the administering increases the fluid outflow. In some embodiments, the fluid outflow is modulated by the administration is outflow of aqueous humor.

In some embodiments, the present disclosure provides a method for modulating fluid outflow facility in an eye of a subject in need thereof by administering to the subject a therapeutically-effective amount of a Tie-2 activator, wherein administration of the Tie-2 activator in the subject modulates the fluid outflow facility by from about 5% to about 50%, from about 5% to about 40%, from about 10% to about 40%, from about 15% to about 40%, from about 20% to about 40%, from about 21% to about 40%, from about 22% to about 40%, from about 23% to about 40%, from about 24% to about 40%, from about 25% to about 40%, from about 26% to about 40%, from about 27% to about 40%, from about 28% to about 40%, from about 29% to about 40%, from about 30% to about 40%, from about 30% to about 45%, or from about 30% to about 50%, as compared to the absence of administration.

In some embodiments, administration of a compound disclosed herein to a subject increases the fluid outflow facility by about 2 nL/min/mmHg to about 6 nL/min/mmHg, from about 2.5 nL/min/mmHg to about 6 nL/min/mmHg, from about 3 nL/min/mmHg to about 6 nL/min/mmHg, from about 3.5 nL/min/mmHg to about 6 nL/min/mmHg, from about 4 nL/min/mmHg to about 6 nL/min/mmHg, from about 4.5 nL/min/mmHg to about 6 nL/min/mmHg, from about 5 nL/min/mmHg to about 6 nL/min/mmHg, from about 2 nL/min/mmHg to about 5 nL/min/mmHg, from about 2.5 nL/min/mmHg to about 5 nL/min/mmHg, from about 3 nL/min/mmHg to about 5 nL/min/mmHg, from about 3.5 nL/min/mmHg to about 5 nL/min/mmHg, from about 4 nL/min/mmHg to about 5 nL/min/mmHg, from about 4.5 nL/min/mmHg to about 5 nL/min/mmHg, from about 2.5 nL/min/mmHg to about 3.5 nL/min/mmHg, from about 3 nL/min/mmHg to about 4 nL/min/mmHg, from about 4.5 nL/min/mmHg to about 5.5 nL/min/mmHg, or from about 5 nL/min/mmHg to about 6 nL/min/mmHg.

In some embodiments, the present disclosure provides a method of reducing intraocular pressure in ocular normotensive patients with diabetic eye disease. Ocular normotensive can refer to an ocular pressure that is no more than about 24 mmHg. Ocular normotensive can refer to an ocular pressure that is from about 5 mmHg to about 24 mmHg, from about 6 mmHg to about 24 mmHg, from about 7 mmHg to about 24 mmHg, from about 8 mmHg to about 24 mmHg, from about 9 mmHg to about 24 mmHg, from about 10 mmHg to about 24 mmHg, from about 5 mmHg to about 23 mmHg, from about 5 mmHg to about 22 mmHg, from about 5 mmHg to about 21 mmHg, from about 5 mmHg to about 20 mmHg, from about 6 mmHg to about 23 mmHg, from about 6 mmHg to about 22 mmHg, from about 6 mmHg to about 21 mmHg, from about 6 mmHg to about 20 mmHg, from about 8 mmHg to about 22 mmHg, from about 8 mmHg to about 20 mmHg, from about 10 mmHg to about 24 mmHg, from about 10 mmHg to about 22 mmHg, from about 10 mmHg to about 20 mmHg, from about 11 mmHg to about 19 mmHg, or from about 12 mmHg to about 18 mmHg. In some embodiments, a subject disclosed herein is ocular normotensive with an intraocular pressure of no more than about 16 mmHg.

Visual Acuity.

A compound disclosed herein can reduce the likelihood of vision loss in a subject disclosed herein.

A subject described herein can be evaluated on the basis of visual acuity. Visual acuity can be described by a Snellan fraction. The visual acuity of a subject disclosed herein can be about 20/200, about 20/100, about 20/70, about 20/50, about 20/40, or about 20/20.

A compound of the disclosure can increase visual acuity in an eye of a subject. Improvement in visual acuity can be determined by the number of letters, arranged in lines, that a subject can read on an Early Treatment Diabetic Retinopathy Study (ETDRS) eye chart. Each line on an ETDRS eye chart has five letters, and a count of the number of letters that can read by a subject can provide a visual acuity determination.

In some embodiments, administration of a compound disclosed herein can increase visual acuity in a subject by, for example, at least about 3 ETDRS letters, at least about 4 ETDRS letters, at least about 5 ETDRS letters, at least about 6 ETDRS letters, at least about 7 ETDRS letters, at least about 8 ETDRS letters, at least about 9 ETDRS letters, at least about 10 ETDRS letters, at least about 11 ETDRS letters, at least about 12 ETDRS letters, at least about 13 ETDRS letters, at least about 14 ETDRS letters, at least about 15 ETDRS letters, at least about 16 ETDRS letters, at least about 17 ETDRS letters, at least about 18 ETDRS letters, at least about 19 ETDRS letters, at least about 20 ETDRS letters, at least about 25 ETDRS letters, at least about 30 ETDRS letters, at least about 35 ETDRS letters, or at least about 40 ETDRS letters.

In some embodiments, the administration increases best corrected visual acuity in an eye of the subject by at least 2 Early Treatment Diabetic Retinopathy Study (ETDRS) letters, such as, for example, at least about 3 ETDRS letters, at least about 4 ETDRS letters, at least about 5 ETDRS letters, at least about 6 ETDRS letters, at least about 7 ETDRS letters, at least about 8 ETDRS letters, at least about 9 ETDRS letters, at least about 10 ETDRS letters, at least about 11 ETDRS letters, at least about 12 ETDRS letters, at least about 13 ETDRS letters, at least about 14 ETDRS letters, at least about 15 ETDRS letters, at least about 16

ETDRS letters, at least about 17 ETDRS letters, at least about 18 ETDRS letters, at least about 19 ETDRS letters, at least about 20 ETDRS letters, at least about 25 ETDRS letters, at least about 30 ETDRS letters, at least about 35 ETDRS letters, or at least about 40 ETDRS letters, wherein the eye of the subject has a visual acuity that is greater than 20/100 before the administering.

Schlemm's Canal Area.

A compound of the disclosure can increase an area of a Schlemm's canal of a subject. In some embodiments, treatment of a subject with a compound of the disclosure can increase an area of a Schlemm's canal of a subject by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30%.

In some embodiments, treatment of a subject with a compound of the disclosure can increase an area of a Schlemm's canal of a subject by from about 1% to about 30%, such as from about 2% to about 30%, from about 3% to about 30%, from about 4% to about 30%, from about 5% to about 30%, from about 6% to about 30%, from about 7% to about 30%, from about 8% to about 30%, from about 9% to about 30%, from about 10% to about 30%, from about 11% to about 30%, from about 12% to about 30%, from about 13% to about 30%, from about 14% to about 30%, from about 15% to about 25%, from about 5% to about 20%, from about 5% to about 19%, from about 5% to about 18%, from about 5% to about 17%, from about 5% to about 16%, from about 5% to about 15%, from about 6% to about 15%, from about 7% to about 15%, from about 8% to about 15%, from about 9% to about 15% percent, or from about 10% to about 15%.

EXAMPLES

Non-limiting examples of compounds disclosed herein are listed in TABLE 2.

TABLE 2

| No. | Compound | HPTP-β IC$_{50}$ μM |
|---|---|---|
| AA1 | 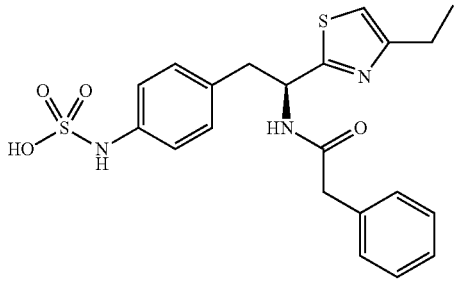 [SMILES: CCc1csc([C@H](Cc2ccc(NS(=O)(=O)O)cc2)NC(=O)Cc2ccccc2)n1]<br>(S)-{4-[2-(4-Ethylthiazol-2-yl)-2-(phenylacetylamino)ethyl]-phenyl}sulfamic acid | 0.000157 |
| AA2 | 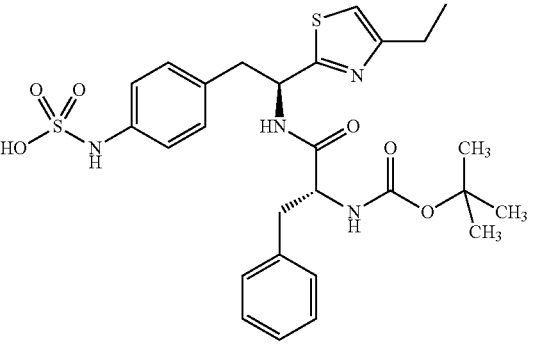 [SMILES: CCc1csc([C@H](Cc2ccc(NS(=O)(=O)O)cc2)NC(=O)[C@@H](Cc2ccccc2)NC(=O)OC(C)(C)C)n1]<br>4-{(S)-2-[(R)-2-(tert-butoxycarbonylamino)-3-phenylpropanamido]-2-(4-ethylthiazol-2-yl)ethyl}phenylsulfamic acid | 0.004 |

TABLE 2-continued

| No. | Compound | HPTP-β IC$_{50}$ μM |
|---|---|---|
| AA3 | 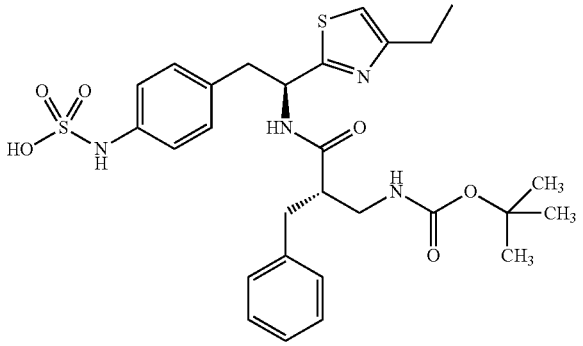 [SMILES: CCc1csc([C@H](Cc2ccc(NS(=O)(=O)O)cc2)NC(=O)[C@H](CNC(=O)OC(C)(C)C)Cc2ccccc2)n1] {1[1-(5-Ethylthiazol-2-yl)-(S)-2-(4-sulfoaminophenyl) ethyl-carbamoyl]-(S)-2-phenylethyl}methyl carbamic acid tert-butyl ester | 0.031 |
| AA4 | 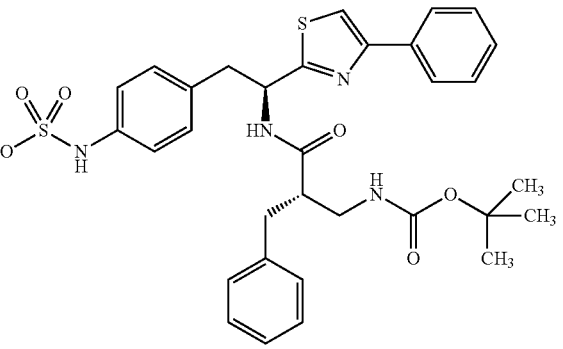 {1-[1-(5-phenylthiazol-2-yl)-(S)-2-(4-sulfoaminophenyl)ethylcarbamoyl]-(S)-2-phenylethyl}methyl carbamic acid tert-butyl ester | $<5 \times 10^{-8}$ |
| AA5 | 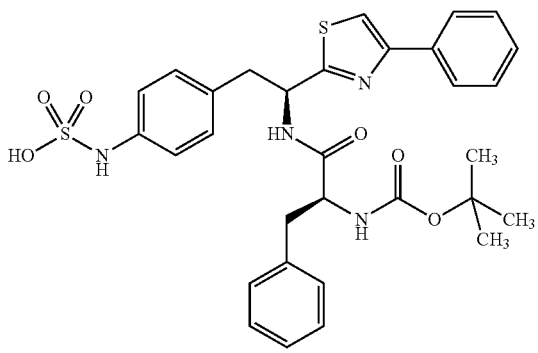 [SMILES: CC(C)(C)OC(=O)N[C@@H](Cc1ccccc1)C(=O)N[C@@H](Cc1ccc(NS(=O)(=O)O)cc1)c1nc(-c2ccccc2)cs1] 4-{(S)-2-(S)-2-(tert-Butoxycarbonylamino)-3-phenylpropanamido-2-(2-phenylthiazol-4-yl)}phenylsulfamic acid | $<5 \times 10^{-8}$ |

TABLE 2-continued
| No. | Compound | HPTP-β IC$_{50}$ μM |
|---|---|---|
| AA6 | 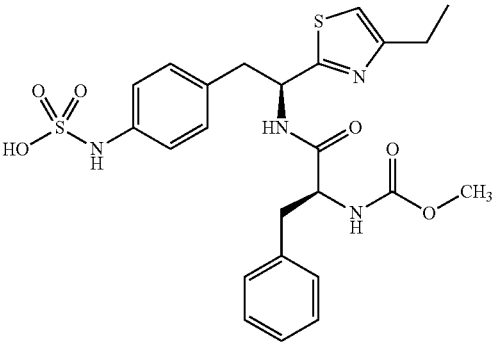 [SMILES: CCc1csc([C@H](Cc2ccc(NS(=O)(=O)O)cc2)NC(=O)[C@H](Cc2ccccc2)NC(=O)OC)n1] 4-{(S)-2-(4-Ethylthiazol-2-yl)-2-[(S)-2-(methoxycarbonylamino)-3-phenylpropanamido]ethyl}phenylsulfamic acid | 0.000162 |
| AA7 | 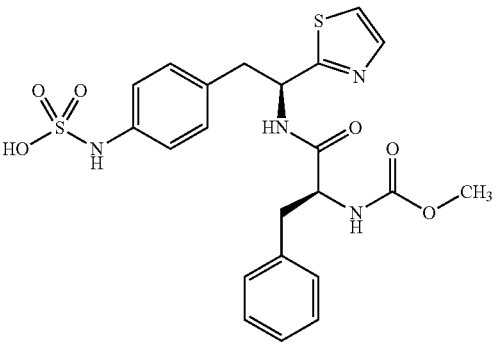 [SMILES: COC(=O)N[C@@H](Cc1ccccc1)C(=O)N[C@@H](Cc1ccc(NS(=O)(=O)O)cc1)c1nccs1] 4-{(S)-2-[(S)-2-(Methoxycarbonylamino)-3-phenylpropanamido]-2-(thiazol-2-yl)ethyl}phenylsulfamic acid | 0.006 |
| AA8 | 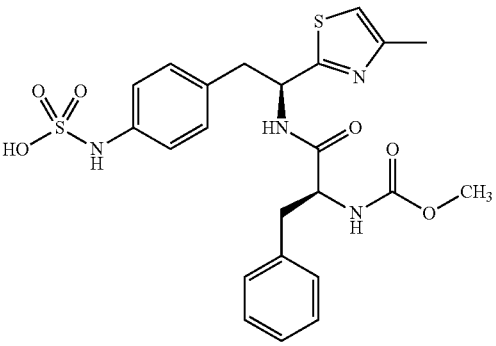 [SMILES: COC(=O)N[C@@H](Cc1ccccc1)C(=O)N[C@@H](Cc1ccc(NS(=O)(=O)O)cc1)c1nc(C)cs1] 4-{(S)-2-[(S)-2-(Methoxycarbonylamino)-3-phenylpropanamido]-2-(4-methylthiazol-2-yl)ethyl}phenylsulfamic acid | 0.001 |

TABLE 2-continued
| No. | Compound | HPTP-β IC$_{50}$ μM |
|---|---|---|
| AA9 | 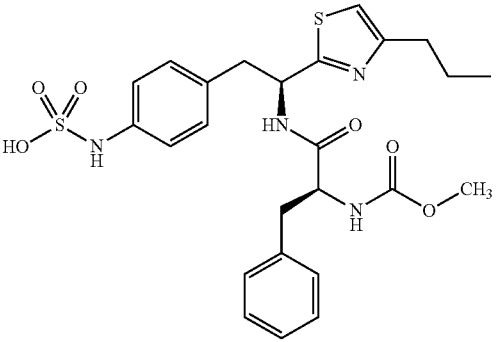 [SMILES: CCCc1csc([C@H](Cc2ccc(NS(=O)(=O)O)cc2)NC(=O)[C@H](Cc2ccccc2)NC(=O)OC)n1] 4-{(S)-2-[(S)-2-(Methoxycarbonylamino)-3-phenylpropanamido]-2-(4-propylthiazol-2-yl)ethyl}phenylsulfamic acid | 0.0001 |
| AA10 | 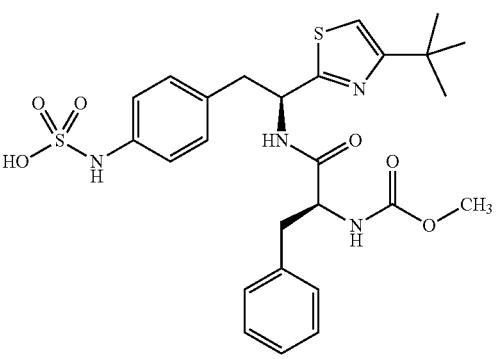 [SMILES: COC(=O)N[C@@H](Cc1ccccc1)C(=O)N[C@@H](Cc1ccc(NS(=O)(=O)O)cc1)c1nc(C(C)(C)C)cs1] 4-{(S)-2-(4-tert-Butylthiazol-2-yl)-2-[(S)-2-(methoxycarbonylamino)-3-phenylpropanamido]ethyl}phenylsulfamic acid | 0.0002 |
| AA11 | 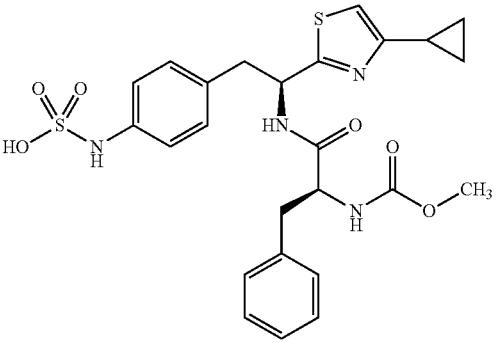 [SMILES: COC(=O)N[C@@H](Cc1ccccc1)C(=O)N[C@@H](Cc1ccc(NS(=O)(=O)O)cc1)c1nc(C2CC2)cs1] 4-{(S)-2-(4-Cyclopropylthiazol-2-yl)-2-[(S)-2-(methoxy-carbonylamino)-3-phenylpropanamido]ethyl}phenylsulfamic acid | 0.00001 |

TABLE 2-continued
| No. | Compound | HPTP-β IC$_{50}$ μM |
|---|---|---|
| AA12 | 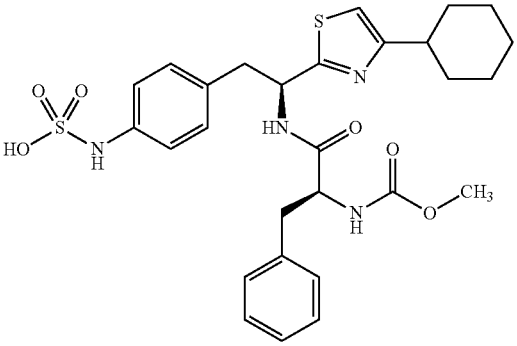 [SMILES: COC(=O)N[C@@H](Cc1ccccc1)C(=O)N[C@@H](Cc1ccc(NS(=O)(=O)O)cc1)c1nc(C2CCCCC2)cs1] 4-{(S)-2-(4-Cyclohexylthiazol-2-yl)-2-[(S)-2-(methoxycarbonylamino)-3-phenyl-propanamido]ethyl}phenylsulfamic acid | <5 × 10$^{-8}$ |
| AA13 | 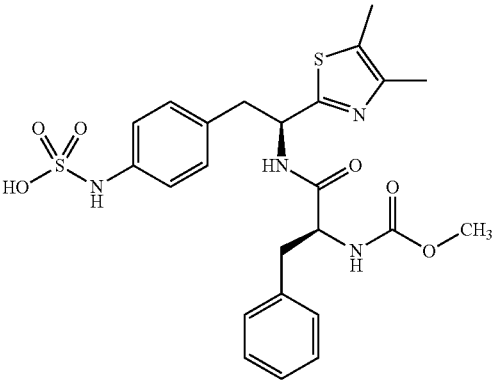 [SMILES: COC(=O)N[C@@H](Cc1ccccc1)C(=O)N[C@@H](Cc1ccc(NS(=O)(=O)O)cc1)c1nc(C)c(C)s1] 4-{(S)-2-(4,5-Dimethylthiazol-2-yl)-2-[(S)-2-(methoxycarbonylamino)-3-phenyl-propanamido]ethyl}phenylsulfamic acid | 0.001 |
| AA14 | 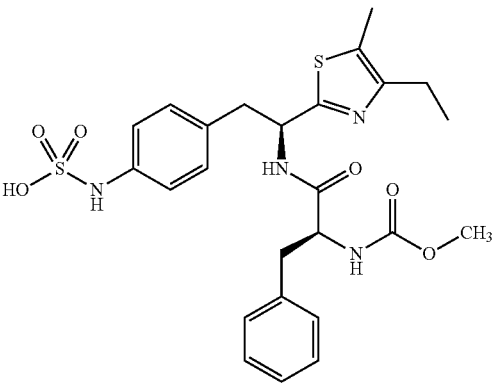 [SMILES: CCc1nc([C@H](Cc2ccc(NS(=O)(=O)O)cc2)NC(=O)[C@H](Cc2ccccc2)NC(=O)OC)sc1C] 4-{(S)-2-(4-Ethyl-5-methylthiazol-2-yl)-2-[(S)-2-(methoxy-carbonylamino)-3-phenyl-propanamido]ethyl}phenylsulfamic acid | 0.0001 |

TABLE 2-continued

| No. | Compound | HPTP-β IC$_{50}$ μM |
|---|---|---|
| AA15 | 4-{(S)-2-[(S)-2-(Methoxycarbonylamino)-3-phenylpropanamido]-2-[4-(2,2,2-trifluoroethyl)thiazol-2-yl]ethyl}phenylsulfamic acid | 0.0003 |
| AA16 | 4-{(S)-2-[(S)-2-(Methoxycarbonylamino)-3-phenylpropanamido]-2-[4-(3,3,3-trifluoropropyl)thiazol-2-yl]ethyl}phenylsulfamic acid | 0.00008 |
| AA17 | 4-{(S)-2-[(S)-2-(Methoxycarbonylamino)-3-phenylpropanamido]-2-[4-(methoxymethyl)thiazol-2-yl]ethyl}phenylsulfamic acid | 0.001 |

TABLE 2-continued
| No. | Compound | HPTP-β IC$_{50}$ μM |
|---|---|---|
| AA18 | 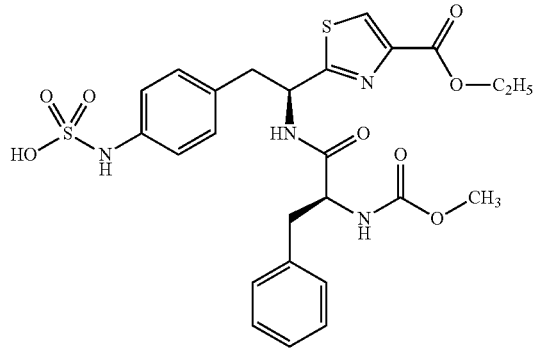 [SMILES: CCOC(=O)c1csc([C@H](Cc2ccc(NS(=O)(=O)O)cc2)NC(=O)[C@H](Cc2ccccc2)NC(=O)OC)n1] 4-{(S)-2-(4-(Ethoxycarbonyl)thiazol-2-yl)-2-[(S)-2-(methoxy-carbonylamino)-3-phenylpropanamido]ethyl}phenylsulfamic acid | 0.0002 |
| AA19 | 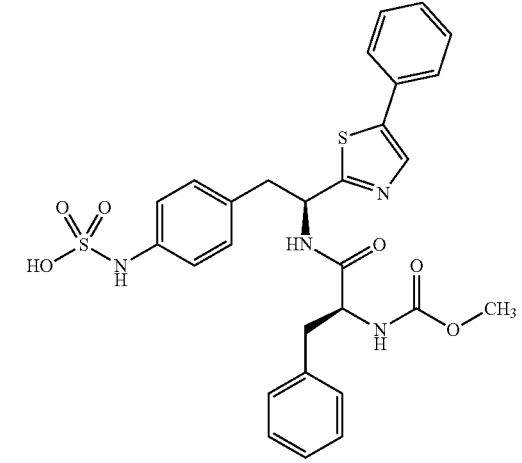 [SMILES: COC(=O)N[C@@H](Cc1ccccc1)C(=O)N[C@@H](Cc1ccc(NS(=O)(=O)O)cc1)c1ncc(-c2ccccc2)s1] 4-{(S)-2-[(S)-2-(Methoxycarbonylamino)-3-phenylpropanamido]-2-(5-phenylthiazol-2-yl)ethyl}phenylsulfamic acid | 0.0003 |
| AA20 | 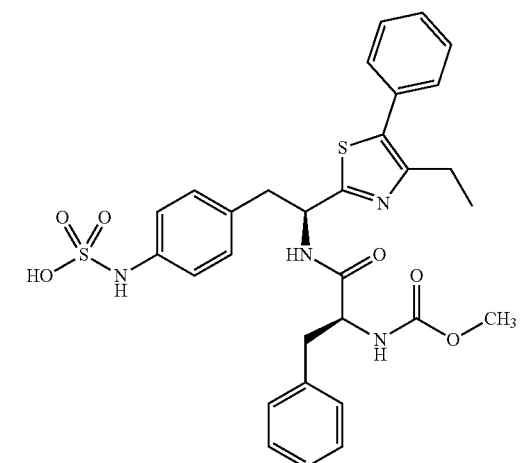 4-{(S)-2-(4-Ethyl-5-phenylthiazol-2-yl)-2-[(S)-2-(methoxy-carbonylamino)-3-phenyl-propanamido]ethyl}phenylsulfamic acid | <5 × 10$^{-8}$ |

TABLE 2-continued
| No. | Compound | HPTP-β IC$_{50}$ μM |
|---|---|---|
| AA21 | 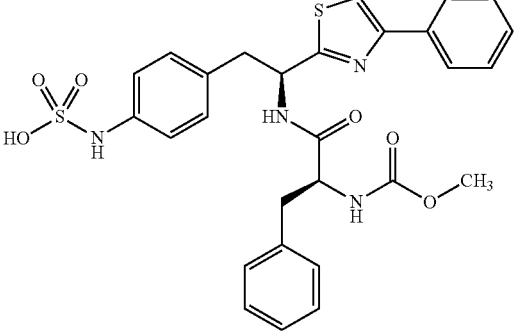 4-{(S)-2-[(S)-2-(Methoxycarbonylamino)-3-phenylpropanamido]-2-(4-phenylthiazol-2-yl)ethyl}phenylsulfamic acid | <2 × 10$^{-6}$ |
| AA22 | 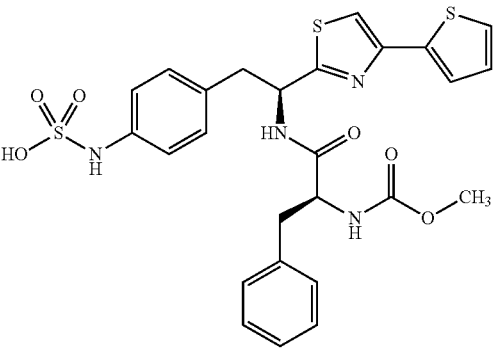 [SMILES: COC(=O)N[C@@H](Cc1ccccc1)C(=O)N[C@@H](Cc1ccc(NS(=O)(=O)O)cc1)c1nc(-c2cccs2)cs1] 4-{(S)-2-[(S)-2-(Methoxycarbonylamino)-3-phenylpropanamido]-2-[4-(thiophen-2-yl)thiazol-2-yl]ethyl}phenylsulfamic acid | <5 × 10$^{-8}$ |
| AA23 | 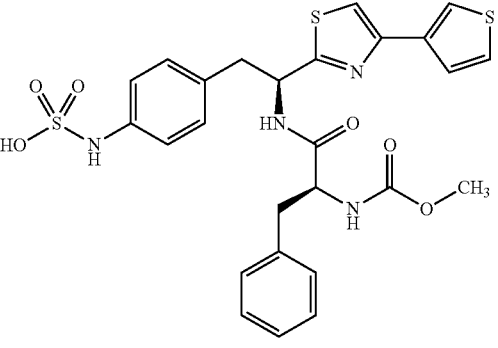 [SMILES: COC(=O)N[C@@H](Cc1ccccc1)C(=O)N[C@@H](Cc1ccc(NS(=O)(=O)O)cc1)c1nc(-c2ccsc2)cs1] 4-{(S)-2-[(S)-2-(Methoxycarbonylamino)-3-phenylpropanamido]-2-[4-(thiophen-3-yl)thiazol-2-yl]ethyl}phenylsulfamic acid | 0.00009 |

TABLE 2-continued

| No. | Compound | HPTP-β IC$_{50}$ μM |
|---|---|---|
| AA24 | 4-{(S)-2-(5,6-Dihydro-4H-cyclopenta[d]thiazol-2-yl)-2-[(S)-2-(methoxycarbonylamino)-3-phenylpropanamido]ethyl}phenylsulfamic acid | 0.001 |
| AA25 | 4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid | 0.0004 |
| AA26 | 4-{(S)-2-[4-(5-Chlorothiophen-2-yl)thiazol-2-yl]-2-[(S)-2-(methoxycarbonylamino)-3-phenylpropanamido]ethyl}phenyl-sulfamic acid | <5 × 10$^{-8}$ |

TABLE 2-continued
| No. | Compound | HPTP-β IC$_{50}$ μM |
|---|---|---|
| AA27 | 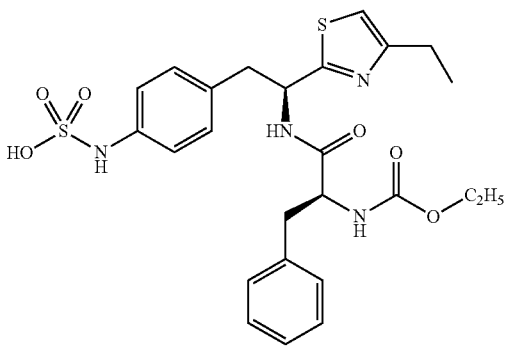 [SMILES: CCOC(=O)N[C@@H](Cc1ccccc1)C(=O)N[C@@H](Cc1ccc(NS(=O)(=O)O)cc1)c1nc(CC)cs1] 4-{(S)-2-[(S)-2-(Ethoxycarbonylamino)-3-phenylpropanamido]-2-(4-ethylthiazol-2-yl)ethyl}phenylsulfamic acid | 0.00014 |
| AA28 | 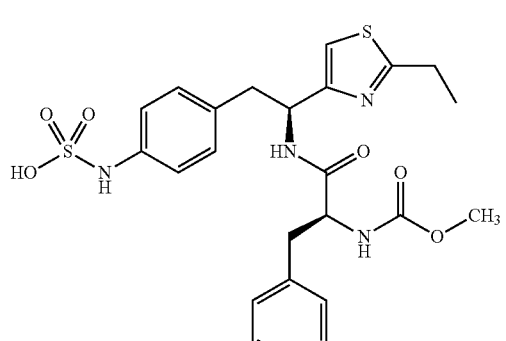 4-{(S)-2-[(S)-2-(Methoxycarbonylamino)-3-phenylpropanamido]-2-(2-ethylthiazol-4-yl)ethyl}phenylsulfamic acid | 0.0001 |
| AA29 | 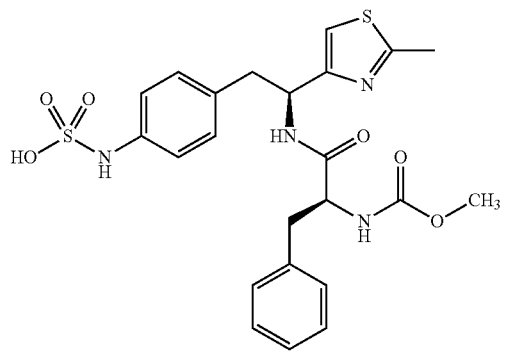 [SMILES: COC(=O)N[C@@H](Cc1ccccc1)C(=O)N[C@@H](Cc1ccc(NS(=O)(=O)O)cc1)c1csc(C)n1] 4-{(S)-2-[(S)-2-(Methoxycarbonylamino)-3-phenylpropanamido]-2-(2-methylthiazol-4-yl)ethyl}phenylsulfamic acid | 0.001 |

TABLE 2-continued

| No. | Compound | HPTP-β IC$_{50}$ μM |
|---|---|---|
| AA30 | 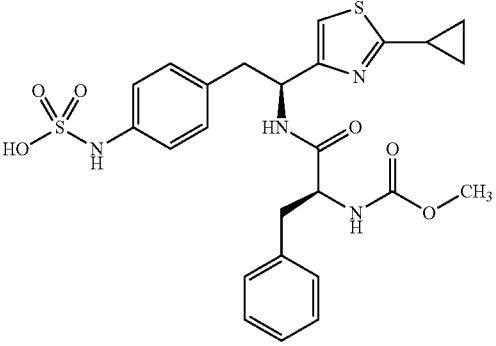 [SMILES: COC(=O)N[C@@H](Cc1ccccc1)C(=O)N[C@@H](Cc1ccc(NS(=O)(=O)O)cc1)c1csc(C2CC2)n1] 4-{(S)-2-(2-Cyclopropylthiazol-4-yl)-2-[(S)-2-(methoxy-carbonylamino)-3-phenylpropanamido]ethyl}phenylsulfamic acid | 0.0002 |
| AA31 | 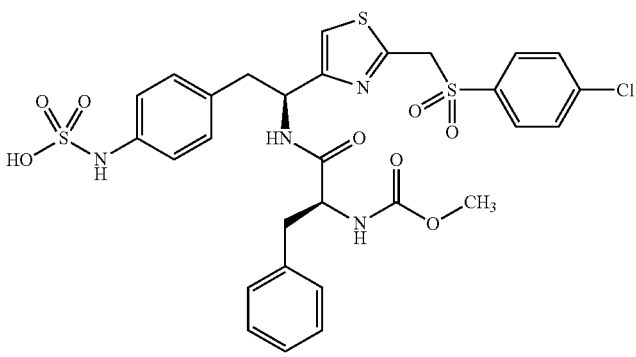 [SMILES: COC(=O)N[C@@H](Cc1ccccc1)C(=O)N[C@@H](Cc1ccc(NS(=O)(=O)O)cc1)c1csc(CS(=O)(=O)c2ccc(Cl)cc2)n1] 4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid | 0.00008 |
| AA32 | 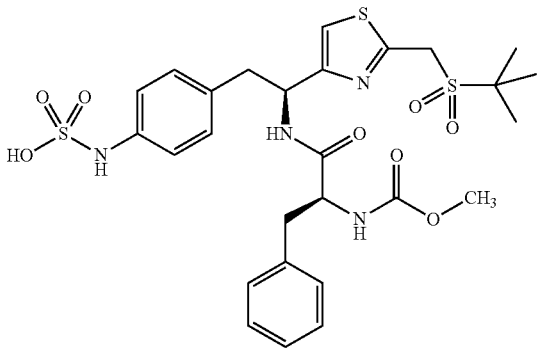 [SMILES: COC(=O)N[C@@H](Cc1ccccc1)C(=O)N[C@@H](Cc1ccc(NS(=O)(=O)O)cc1)c1csc(CS(=O)(=O)C(C)(C)C)n1] 4-{(S)-2-[2-(tert-Butylsulfonylmethyl)thiazol-4-yl]-2-[(S)-2-(methoxycarbonylamino)-3-phenylpropanamido]ethyl}phenylsulfamic acid | 0.002 |

TABLE 2-continued

| No. | Compound | HPTP-β IC$_{50}$ μM |
|---|---|---|
| AA33 | 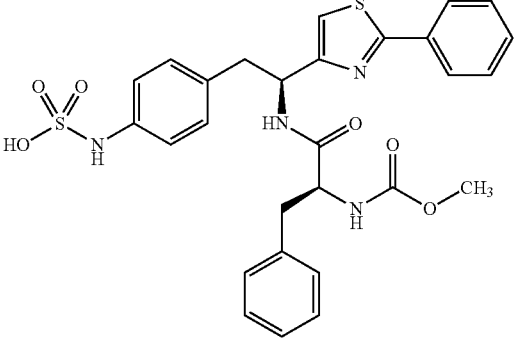 4-{(S)-2-[(S)-2-(Methoxycarbonylamino)-3-phenylpropionamido]-2-(2-phenylthiazole-4-yl)ethyl}phenylsulfamic acid | $7 \times 10^{-7}$ |
| AA34 (Compound 1) | 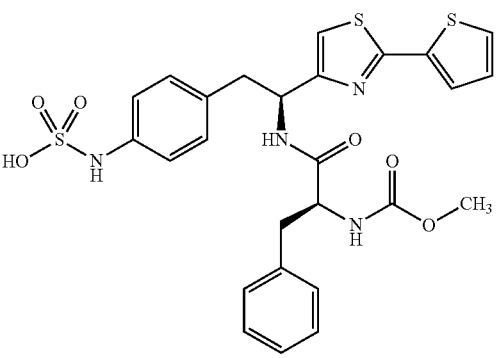 [SMILES: COC(=O)N[C@@H](Cc1ccccc1)C(=O)N[C@@H](Cc1ccc(NS(=O)(=O)O)cc1)c1csc(-c2cccs2)n1] 4-{(S)-2-[(S)-2-(Methoxycarbonylamino)-3-phenylpropanamido]-2-[2-(thiophen-2-yl)thiazol-4-yl]ethyl}phenylsulfamic acid | $5 \times 10^{-8}$ |
| AA35 | 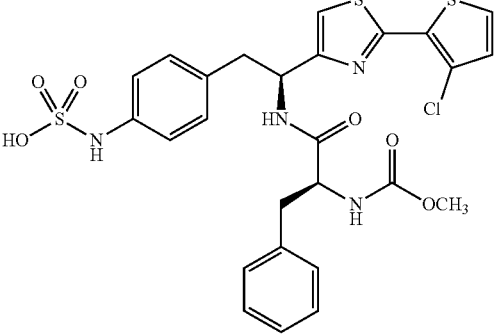 4-{(S)-2-[2-(3-Chlorothiophen-2-yl)thiazol-4-yl]-2-[(S)-2-(methoxycarbonylamino)-3-phenylpropanamido]ethyl}phenylsulfamic acid | $<5 \times 10^{-8}$ |

TABLE 2-continued

| No. | Compound | HPTP-β IC$_{50}$ μM |
|---|---|---|
| AA36 | 4-{(S)-2-[(S)-2-(Methoxycarbonylamino)-3-phenylpropanamido]-2-[2-(3-methylthiophen-2-yl)thiazol-4-yl]ethyl}phenylsulfamic acid | <5 × 10$^{-8}$ |
| AA37 | 4-{[(S)-2-(2-(Furan-2-yl)thiazol-4)yl]-2-[(S)-2-(methoxycarbonylamino)-3-phenylpropanamido]ethyl}phenylsulfamic acid | 0.0004 |
| AA38 | 4-{(S)-2-[(S)-2-(Methoxycarbonylamino)-3-phenylpropanamido]-2-[2-(pyrazin-2-yl)thiazol-4-yl]ethyl}phenylsulfamic acid | 0.003 |

TABLE 2-continued

| No. | Compound | HPTP-β IC$_{50}$ μM |
|---|---|---|
| AA39 | 4-[(S)-2-((S)-2-Acetamido-3-phenylpropanamido)-2-(4-ethylthiazol-2-yl)ethyl}phenylsulfamic acid | 0.001 |
| AA40 | 4-[(S)-2((S)-2-Acetamido-3-phenylpropanamido)-2-(4-tert-butylthiazol-2-yl)ethyl]phenylsulfamic acid | 0.0003 |
| AA41 | 4-{(S)-2-((S)-2-Acetamido-3-phenylpropanamido)-2-[4-(thiophen-3-yl)thiazol-2-yl]ethyl}phenylsulfamic acid | 0.00024 |
| AA42 | 4-{(S)-2-[(S)-2-(tert-Butoxycarbonylamino)-3-methylbutanamido]-2-(4-ethylthiazol-2-yl)ethyl}phenylsulfamic acid | 0.006 |

TABLE 2-continued

| No. | Compound | HPTP-β IC$_{50}$ μM |
|---|---|---|
| AA43 | 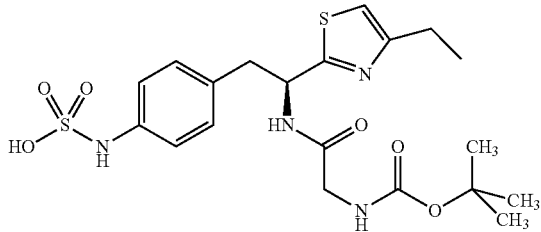 [SMILES: CCc1csc([C@H](Cc2ccc(NS(=O)(=O)O)cc2)NC(=O)CNC(=O)OC(C)(C)C)n1]<br>(S)-4-{2-[2-(tert-Butoxycarbonylamino)acetamido]-2-(4-ethylthiazol-2-yl)ethyl}phenylsulfamic acid | 0.028 |
| AA44 | 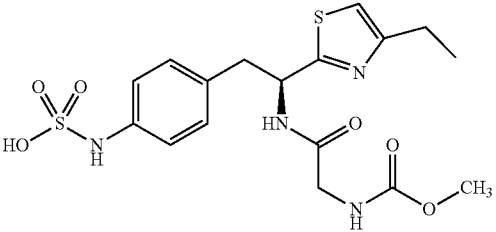 [SMILES: CCc1csc([C@H](Cc2ccc(NS(=O)(=O)O)cc2)NC(=O)CNC(=O)OC)n1]<br>(S)-4-{2-(4-Ethylthiazol-2-yl)-2-[2-(methoxycarbonylamino)acetamido]ethyl}phenylsulfamic acid | 0.020 |
| AA45 | 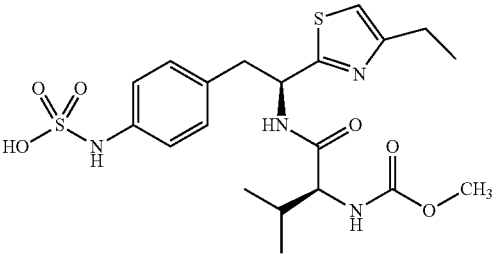 [SMILES: CCc1csc([C@H](Cc2ccc(NS(=O)(=O)O)cc2)NC(=O)[C@@H](NC(=O)OC)C(C)C)n1]<br>4-{(S)-2-(4-Ethylthiazol-2-yl)-2-[(S)-2-(methoxycarbonylamino)-3-methylbutanamido]-ethyl}phenylsulfamic acid | 0.003 |
| AA46 | 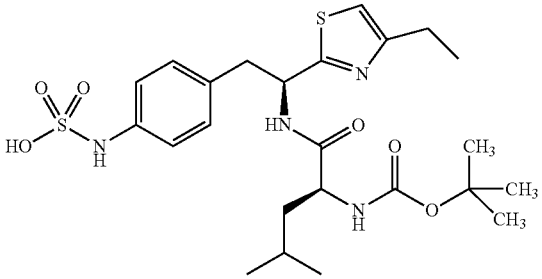 [SMILES: CCc1csc([C@H](Cc2ccc(NS(=O)(=O)O)cc2)NC(=O)[C@H](CC(C)C)NC(=O)OC(C)(C)C)n1]<br>4-{(S)-2-[(S)-2-(tert-Butoxycarbonylamino)-4-methylpentanamido]-2-(4-ethylthiazol-2-yl)ethyl}phenylsulfamic acid | 0.001 |

TABLE 2-continued

| No. | Compound | HPTP-β IC$_{50}$ μM |
|---|---|---|
| AA47 | 4-{(S)-2-(4-Ethylthiazol-2-yl)-2-[(S)-2-(methoxycarbonylamino)-4-methylpentanamido]ethyl}phenylsulfamic acid | 0.0003 |
| AA48 | 4-((S)-2-(4-Ethylthiazol-2-yl)-2-{(S)-2-[2-(methoxycarbonylamino)-acetamido]-3-phenylpropanamido}ethyl)phenylsulfamic acid | 0.0003 |
| AA49 | 4-{(S)-2-[(S)-2-(Methoxycarbonylamino)-4-methylpentanamido]-2-[2-(thiophen-2-yl)thiazol-4-yl]ethyl}phenylsulfamic acid | <5 × 10$^{-8}$ |
| AA50 | (S)-4-{2-[2-(tert-Butoxycarbonylamino)acetamido]-2-(4-ethylthiazol-2-yl)ethyl}-phenylsulfamic acid | 0.028 |

TABLE 2-continued

| No. | Compound | HPTP-β IC$_{50}$ μM |
|---|---|---|
| AA51 | [1-(S)-(Phenylthiazol-2-yl)-2-(4-sulfoaminophenyl)ethyl]-carbamic acid tert-butyl ester | 0.049 |
| AA52 | (S)-4-(2-(4-Methylthiazol-2-yl)-2-pivalamidoethyl)phenyl-sulfamic acid | 0.112 |
| AA53 | (S)-4-(2-(4-Ethylthiazol-2-yl)-2-pivalamidoethyl)phenyl-sulfamic acid | 0.085 |
| AA54 | (S)-4-{2-[4-(hydroxymethyl)thiazol-2-yl]-2-pivalamidoethyl}phenyl-sulfamic acid | 0.266 |
| AA55 | (S)-4-{[2-(4-Ethoxycarbonyl)thiazol-2-yl]-2-pivalamidoethyl}phenylsulfamic acid | 0.584 |

TABLE 2-continued

| No. | Compound | HPTP-β IC$_{50}$ μM |
|---|---|---|
| AA56 | (S)-4-(2-(4-Phenylthiazol-2-yl)-2-pivalamidoethyl)phenylsulfamic acid | 0.042 |
| AA57 | 4-((S)-2-(4-(3-Methoxyphenyl)thiazol-2-yl)-2-pivalamidoethyl)phenylsulfamic acid | 0.110 |
| AA58 | 4-((S)-2-(4-(2,4-Dimethoxyphenyl)thiazol-2-yl)-2-pivalamidoethyl)phenyl-sulfamic acid | 0.086 |
| AA59 | (S)-4-(2-(4-Benzylthiazol-2-yl)-2-pivalamidoethyl)phenylsulfamic acid | 0.113 |
| AA60 | (S)-4-(2-(4-(3-Methoxybenzyl)thiazol-2-yl)-2-pivalamidoethyl)phenylsulfamic acid | 0.132 |

TABLE 2-continued

| No. | Compound | HPTP-β IC$_{50}$ μM |
|---|---|---|
| AA61 | 4-((S)-2-(4-(2,3-Dihydrobenzo[b][1,4]dioxin-6-yl)thiazol-2-yl)-2-pivalamidoethyl)phenylsulfamic acid | 0.138 |
| AA62 | (S)-4-(2-(5-Methyl-4-phenylthiazol-2-yl)-2-pivalamidoethyl)phenylsulfamic acid | 0.098 |
| AA63 | (S)-4-(2-(4-(Biphen-4-yl)thiazol-2-yl)-2-pivalamidoethyl)phenylsulfamic acid | 0.381 |
| AA64 | (S)-4-(2-tert-Butoxycarbonylamino)-2-(2-methylthiazol-4-yl)ethyl)phenylsulfamic acid | 0.033 |

TABLE 2-continued

| No. | Compound | HPTP-β IC$_{50}$ μM |
|---|---|---|
| AA65 | (S)-4-(2-(tert-Butoxycarbonylamino)-2-(4-propylthiazol-2-yl)ethyl)phenyl sulfamic acid | 0.04 |
| AA66 | (S)-4-(2-(tert-Butoxycarbonylamino)-2-(4-tert-butylthiazol-2-yl)ethyl)phenyl sulfamic acid | 0.027 |
| AA67 | (S)-4-(2-(tert-Butoxycarbonylamino)-2-(4-(methoxymethyl)thiazol-2-yl)ethyl)-phenyl sulfamic acid | 0.18 |
| AA68 | (S)-4-(2-(tert-Butoxycarbonylamino)-2-(4-(hydroxymethyl)thiazol-2-yl)ethyl)phenylsulfamic acid | 0.644 |

TABLE 2-continued

| No. | Compound | HPTP-β IC$_{50}$ μM |
|---|---|---|
| AA69 | 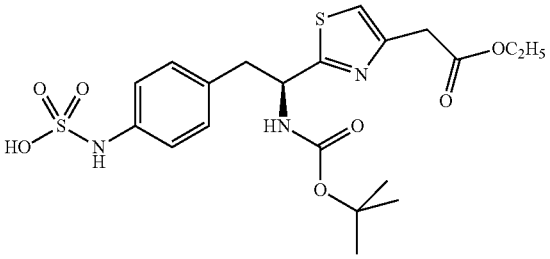 [SMILES: CCOC(=O)Cc1csc([C@H](Cc2ccc(NS(=O)(=O)O)cc2)NC(=O)OC(C)(C)C)n1]<br>(S)-4-(2-tert-Butoxycarbonylamino)-2-(4-(2-ethoxy-2-oxoethyl)thiazol-2-yl)ethyl)phenylsulfamic acid | 0.167 |
| AA70 | 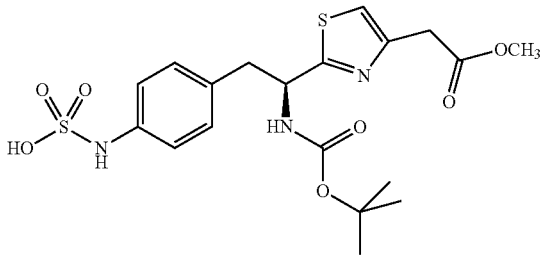 [SMILES: COC(=O)Cc1csc([C@H](Cc2ccc(NS(=O)(=O)O)cc2)NC(=O)OC(C)(C)C)n1]<br>(S)-4-(2-(tert-Butoxycarbonyl)-2-(4-(2-(2-methoxy-2-oxoyethyl amino)-2-oxoethyl)thiazole-2-yl)ethyl)phenylsulfamic acid | 0.132 |
| AA71 | 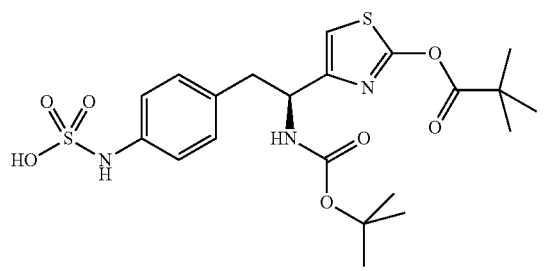 [SMILES: CC(C)(C)OC(=O)N[C@@H](Cc1ccc(NS(=O)(=O)O)cc1)c1csc(OC(=O)C(C)(C)C)n1]<br>(S)-4-(2-(tert-Butoxycarbonylamino)-2-(2-pivalamidothiazol-4-yl)ethyl)phenylsulfamic acid | 0.555 |
| AA72 | 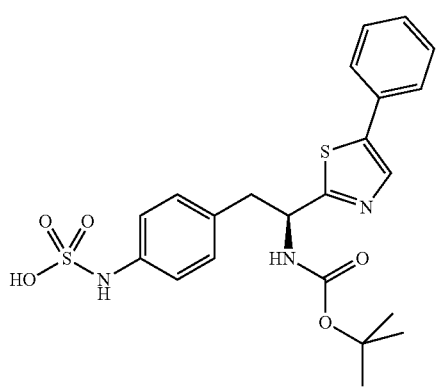 [SMILES: CC(C)(C)OC(=O)N[C@@H](Cc1ccc(NS(=O)(=O)O)cc1)c1ncc(-c2ccccc2)s1]<br>(S)-4-(2-(tert-Butoxycarbonylamino)-2-(5-phenylthiazol-2-yl)ethyl)-phenyl sulfamic acid | 0.308 |

TABLE 2-continued

| No. | Compound | HPTP-β IC$_{50}$ μM |
|---|---|---|
| AA73 | 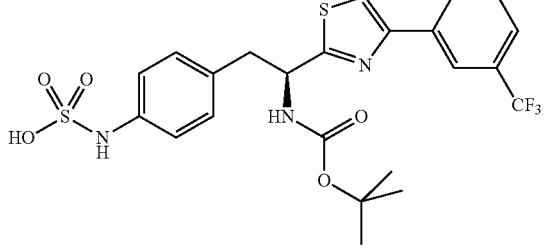<br>4-((S)-2-(tert-Butoxycarbonylamino)-2-(4-(3-(trifluoromethyl)phenyl)thiazol-2-yl)ethyl)-phenyl sulfamic acid | 0.253 |
| AA74 | 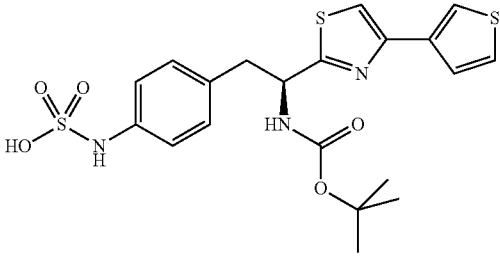 [SMILES: CC(C)(C)OC(=O)N[C@@H](Cc1ccc(NS(=O)(=O)O)cc1)c1nc(-c2ccsc2)cs1]<br>4-((S)-2-(tert-Butoxycarbonylamino)-2-(4-(thiophen-3-yl)thiazol-2-yl)ethyl)phenyl sulfamic acid | 0.045 |
| AA75 | 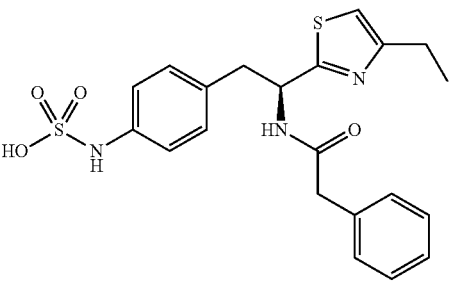 [SMILES: CCc1csc([C@H](Cc2ccc(NS(=O)(=O)O)cc2)NC(=O)Cc2ccccc2)n1]<br>(S)-{4-[2-(4-Ethylthiazol-2-yl)-2-(phenylacetylamido)ethyl]-phenyl}sulfamic acid | 0.05 |
| AA76 | 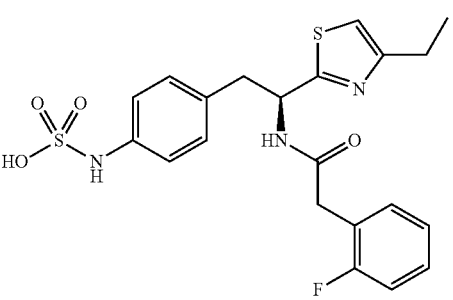 [SMILES: CCc1csc([C@H](Cc2ccc(NS(=O)(=O)O)cc2)NC(=O)Cc2ccccc2F)n1]<br>(S)-4-(2-(4-Ethylthiazol-2-yl)-2-(2-(2-fluorophenyl)acetamido)ethyl)phenyl-sulfamic acid | 0.012 |

TABLE 2-continued

| No. | Compound | HPTP-β IC$_{50}$ μM |
|---|---|---|
| AA77 | (S)-4-(2-(4-Ethylthiazol-2-yl)-2-(2-(3-fluorophenyl)acetamido)ethyl)phenyl-sulfamic acid | 0.0003 |
| AA78 | (S)-4-(2-(2-(2,3-Difluorophenyl)acetamido)-2-(4-ethylthiazol-2-yl)ethyl)phenyl-sulfamic acid | 0.028 |
| AA79 | (S)-4-(2-(2-(3,4-Difluorophenyl)acetamido)-2-(4-ethylthiazol-2-yl)ethyl)phenyl-sulfamic acid | 0.075 |
| AA80 | (S)-4-(2-(2-(2-Chlorophenyl)acetamido)-2-(4-ethylthiazol-2-yl)ethyl)phenyl-sulfamic acid | 0.056 |

TABLE 2-continued

| No. | Compound | HPTP-β IC$_{50}$ μM |
|---|---|---|
| AA81 | (S)-4-(2-(2-(3-Chlorophenyl)acetamido)-2-(4-ethylthiazol-2-yl)ethyl)phenyl-sulfamic acid | 0.033 |
| AA82 | (S)-4-(2-(4-Ethylthiazol-2-yl)-2-(2-(3-hydroxyphenyl)acetamido)ethyl)phenyl-sulfamic acid | 0.04 |
| AA83 | (S)-4-(2-(4-Ethylthiazol-2-yl)-2-(2-(2-methoxyphenyl)acetamido)ethyl)phenyl-sulfamic acid | 0.014 |
| AA84 | (S)-4-(2-(4-Ethylthiazol-2-yl)-2-(2-(3-methoxyphenyl)acetamido)ethyl)phenyl-sulfamic acid | 0.008 |

TABLE 2-continued

| No. | Compound | HPTP-β IC$_{50}$ μM |
|---|---|---|
| AA85 | (S)-4-(2-(4-Ethylthiazol-2-yl)-2-(3-phenylpropanamido)ethyl)phenylsulfamic acid | 0.002 |
| AA86 | (S)-4-(2-(2-(3,4-Dimethoxyphenyl)acetamido)-2-(4-ethylthiazol-2-yl)ethyl)-phenylsulfamic acid | 0.028 |
| AA87 | (S)-4-(2-(2-(2,3-Dimethoxyphenyl)acetamido)-2-(4-ethylthiazol-2-yl)ethyl)-phenylsulfamic acid | 0.037 |
| AA88 | (S)-4-(2-(3-(3-Chlorophenyl)propanamido)-2-(4-ethylthiazol-2-yl)ethyl)phenyl-sulfamic acid | 0.0002 |

TABLE 2-continued

| No. | Compound | HPTP-β IC$_{50}$ μM |
|---|---|---|
| AA89 | (S)-4-(2-(4-Ethylthiazol-2-yl)-2-(3-(2-methoxyphenyl)propanamido)ethyl)phenyl-sulfamic acid | 0.003 |
| AA90 | (S)-4-(2-(4-Ethylthiazol-2-yl)-2-(3-(3-methoxyphenyl)propanamido)ethyl)phenyl-sulfamic acid | 0.01 |
| AA91 | (S)-4-(2-(4-Ethylthiazol-2-yl)-2-(3-(4-methoxyphenyl)propanamido)ethyl)phenyl-sulfamic acid | 0.006 |
| AA92 | (S)-4-{2-[2-(4-Ethyl-2,3-dioxopiperazin-1-yl)acetamide]-2-(4-ethylthiazol-2-yl)ethyl}phenylsulfamic acid | 0.002 |

TABLE 2-continued

| No. | Compound | HPTP-β IC$_{50}$ μM |
|---|---|---|
| AA93 | (S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid | 0.002 |
| AA94 | (S)-4-[2-(Benzo[d][1,3]dioxole-5-carboxamido)-2-(4-ethylthiazol-2-yl)ethyl]phenylsulfamic acid | 0.042 |
| AA95 | (S)-4-(2-(5-methyl-1,3,4-thiadiazol-2-ylamino)-2-(2-phenylthiazol-4-yl)ethyl)phenylsulfamic acid | 0.003 |
| AA96 | (S)-4-(2-(5-Phenyl-1,3,4-thiadiazol-2-ylamino)-2-(2-phenylthiazol-4-yl)ethyl)-phenylsulfamic acid | 0.046 |

TABLE 2-continued

| No. | Compound | HPTP-β IC$_{50}$ μM |
|---|---|---|
| AA97 | 4-((S)-2-(5-Propyl-1,3,4-thiadiazol-2-ylamino)-2-(2-(thiophen-2-yl)thiazol-4-yl)ethyl)phenylsulfamic acid | 0.0002 |
| AA98 | 4-((S)-2-(5-Benzyl-1,3,4-thiadiazol-2-ylamino)-2-(2-(thiophen-2-yl)thiazol-4-yl)ethyl)phenylsulfamic acid | 0.0006 |
| AA99 | 4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid | 0.002 |
| AA100 | 4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid | $9 \times 10^{-6}$ |

Example 1: Subcutaneous Administration of Compound 1 Reduces IOP in Ocular Normotensive Patients with Diabetic Macular Edema A phase 2 human clinical trial in ocular normotensive human patients with diabetic eye disease was undertaken to assess the effect of subcutaneous administration of the sodium salt of Compound 1 on IOP.

Compound 1

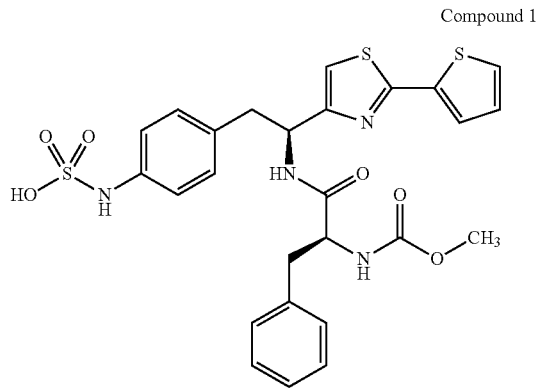 [SMILES: COC(=O)N[C@@H](Cc1ccccc1)C(=O)N[C@@H](Cc1ccc(NS(=O)(=O)O)cc1)c1csc(-c2cccs2)n1]

Methods.

IOP in patients were measured using a double-masked, parallel-group designed to assess the effects of subcutaneous (SC) Compound 1 (sodium salt) alone, or as an adjunct to intravitreal ranibizumab trial. 144 human subjects with diabetic retinopathy complicated by center-involved diabetic macular edema (DME) were randomized to 3 months of one of 3 treatments: 1) Compound 1 (15 mg) SC twice daily (BID) plus sham monthly intravitreal injection (IVT); 2) Compound 1 SC BID plus ranibizumab (0.3 mg) monthly IVT; and 3) Placebo SC BID+ranibizumab IVT. At baseline, mean age was 61.3±1.3 years; 59% of subjects were male; 82.6% had Type 2 diabetes; mean HBA1c was 7.5%±1.3%; mean best corrected visual acuity was 60.2 ETDRS letters (Snellen 20/63); and mean IOP was 15.7 mmHg±3.4. Ophthalmic safety assessments were performed at baseline and monthly during the 3-month treatment period including a single IOP measurement by applanation tonometry in both the study eye and the fellow eye at each time point. By protocol, all patients had baseline IOP<24 mmHg (ocular normotensive).

In the pre-specified safety analysis, change from baseline IOP was analyzed using a t-test (null hypothesis 0 change from baseline). The level of significance was set at 0.05. A post hoc analysis of the subject level IOP measure was the change from baseline in the average over both eyes within a subject for each timepoint. Statistical testing of each timepoint was completed using ANCOVA with baseline IOP (averaged over both eyes within a subject) as covariate. Additionally, statistical testing averaging across all timepoints was completed using a mixed-model repeated measures ANCOVA. The level of significance was set at 0.05.

Results.

The effects on mean IOP change from baseline is shown in FIG. 1A and TABLE 3. A consistent reduction from baseline (mean change from baseline±standard error) was seen in both Compound 1 groups at all time points. The observation was statistically significant in both groups and both eyes (Study Eye and Fellow Eye) at the 8- and 12-week time points. * $p \leq 0.05$;  $p \leq 0.01$; * $p \leq 0.005$.

TABLE 3

|  | Compound 1 + Sham | | Compound 1 + ranibizumab | | Placebo + ranibizumab | |
| --- | --- | --- | --- | --- | --- | --- |
|  | SE | FE | SE | FE | SE | FE |
| Baseline n | 48 | 48 | 49 | 49 | 47 | 47 |
| Baseline IOP mean (SD) | 15.8 (3.69) | 15.4 (3.37) | 15.9 (3.15) | 16.1 (3.18) | 15.2 (3.14) | 15.8 (6.12) |
| Week 4 n | 45 | 45 | 48 | 48 | 44 | 44 |
| Week 4 IOP | 14.8 (3.27) | 14.5 (2.81) | 14.7 (3.05) | 14.4 (3.58) | 15.0 (3.50) | 15.5 (4.85) |
| Change from BL | −0.8 (3.34) | −0.8 (3.36) | −1.3 (3.04) | −1.8 (2.98) | −0.1 (2.74) | −0.3 (3.49) |
| Change BL-Week 4 (p-value) | 0.125 | 0.118 | 0.004 | 0.001 | 0.870 | 0.606 |
| Week 8 n | 45 | 45 | 47 | 47 | 44 | 44 |
| Week 8 IOP | 14.4 (3.53) | 14.3 (3.22) | 14.6 (3.54) | 14.7 (3.81) | 15.0 (3.61) | 15.5 (4.52) |
| Change from BL | −1.1 (3.37) | −1.1 (3.58) | −1.5 (3.07) | −1.4 (3.66) | 0.0 (3.25) | −0.3 (3.44) |
| Change BL Week 8 (p-value) | 0.032 | 0.052 | 0.002 | 0.013 | 0.926 | 0.572 |
| Week 12 n | 45 | 45 | 48 | 48 | 47 | 47 |
| Week 12 IOP | 14.3 (3.56) | 14.0 (3.41) | 15.1 (3.51) | 14.7 (3.39) | 15.3 (4.09) | 15.7 (5.19) |
| Change from BL | −1.4 (3.16) | −1.4 (3.29) | −1.0 (3.24) | −1.5 (3.49) | 0.1 (3.83) | −0.1 (3.62) |
| Change BL-Week 12 (p-value) | 0.006 | 0.005 | 0.042 | 0.006 | 0.880 | 0.841 |

BL = baseline;
n = number of subjects;
SE = study eye;
FE = Fellow eye;
SD = standard deviation Subcutaneous administration of Compound 1 reduced mean IOP by 0.8 to 1.8 mmHg compared to baseline. The reduction in IOP was statistically significant across all time points in both eyes (Study Eye and Fellow Eye) for the Compound 1-treated groups, except for the Compound 1+Sham group at the Week 4 time point. IOP reduction with Compound 1 was similar in eyes treated with or without ranibizumab at all time points. By comparison, patients in the Placebo+ranibizumab group did not show a significant change in mean IOP from baseline in either Study or Fellow Eye (mean change from −0.3 to +0.1 mmHg).

Analysis of subject-level (average of Study Eye and Fellow Eye) changes in IOP was performed to facilitate within-group and cross-group comparisons. The results are summarized in TABLE 4 and FIG. 1B.

TABLE 4

|  | Compound 1 + Sham | Compound 1 + ranibizumab | All Compound 1 | Placebo + ranibizumab |
| --- | --- | --- | --- | --- |
| Baseline mean IOP (SD) | 15.6 (3.32) | 16.0 (2.83) | 15.8 (3.08) | 15.5 (3.82) |
| Week 4 | 14.7 (2.88) | 14.5 (2.98) | 14.5 (2.92) | 15.2 (3.50) |
| Change from BL | −0.8 (3.14) | −1.5 (3.04) | −1.2 (2.92) | −0.2 (2.61) |
| Week 8 | 14.4 (3.26) | 14.7 (3.38) | 14.5 (3.31) | 15.3 (3.31) |
| Change from BL | −1.1 (3.25) | −1.4 (3.10) | −1.3 (3.17) | 0.2 (2.86) |
| Week 12 | 14.1 (3.36) | 14.9 (3.25) | 14.5 (3.31) | 15.5 (3.85) |
| Change from BL | −1.4 (2.98) | −1.2 (2.92) | −1.3 (2.93) | 0.0 (3.32) |
| Change from BL (p-value) | 0.001 | <0.001 | <0.001 | 0.56 |
| vs. Placebo (p-value) | 0.017 | 0.013 | 0.005 |  |

BL = baseline;
SD = standard deviation

Figure 1B:
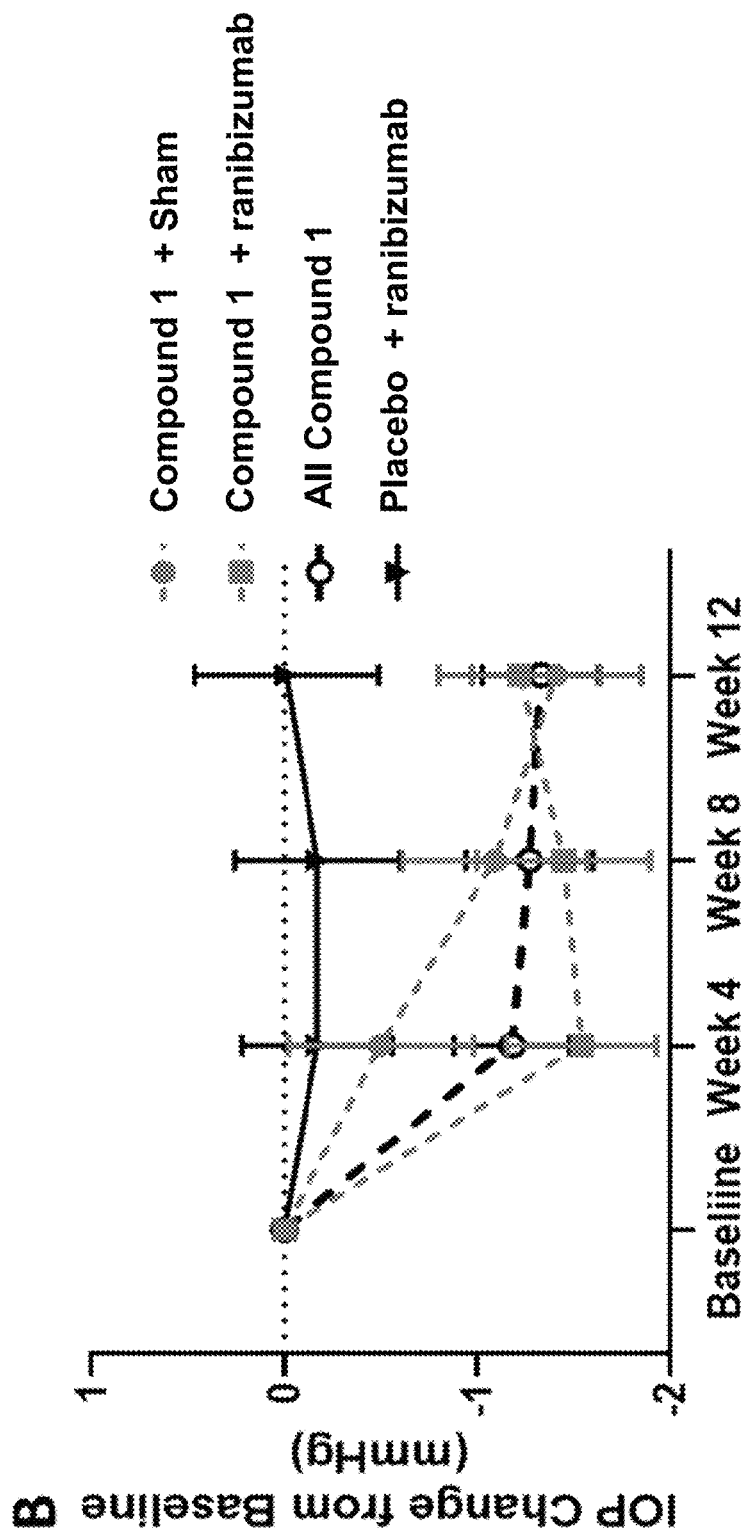
FIG. 1B illustrates patient level IOP mean change from baseline over time in all patients receiving Compound 1, patients receiving Compound 1 alone, patients receiving Compound 1+ ranibizumab, and patients receiving placebo.

FIG. 1B illustrates patient level IOP (average of both eyes, Study and Fellow eye, within each patient) mean change from baseline over time in all patients receiving Compound 1, patients receiving Compound 1 alone (Compound 1+Sham), patients receiving Compound 1+ranibizumab, and patients receiving placebo. The IOP differences from baseline (p<0.001 for all Compound 1 treated groups) and from placebo (p=0.005 for all patients receiving Compound 1; p=0.017 for Compound 1+Sham; p=0.013 for Compound 1+ranibizumab) were statistically significant (MMRM ANCOVA).

Figure 1C:
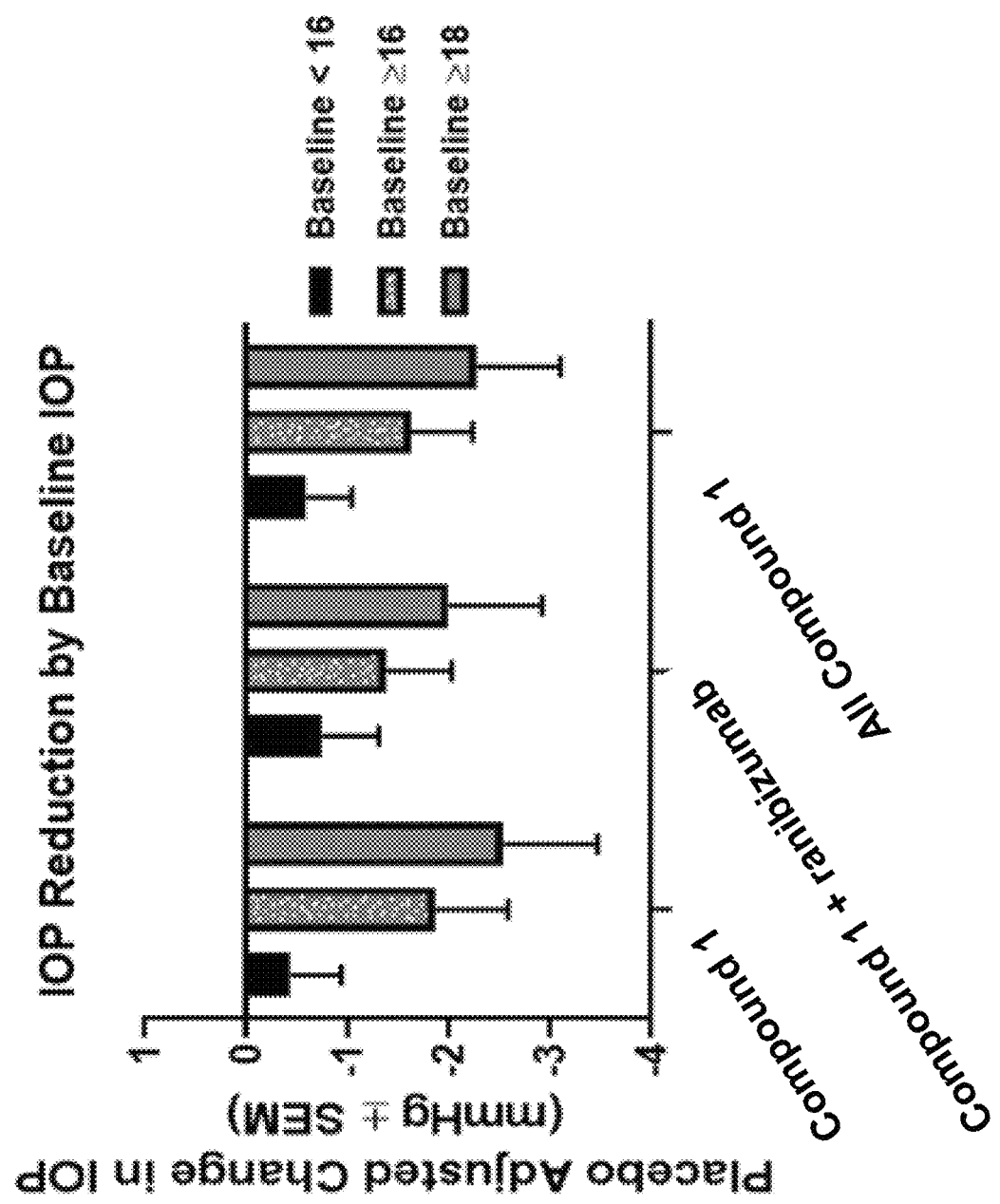
FIG. 1C illustrates patient level IOP change from baseline as a function of baseline IOP.

The subject-level IOP reduction in both Compound 1 treated groups was statistically significant (p=0.001 for Compound 1+Sham and p<0.001 for Compound 1+ranibizumab), whereas no significant change was observed in IOP for placebo-treated patients (p=0.56). Furthermore, the IOP reduction across all study visits was significantly greater than was that of placebo for both the Compound 1+Sham (p=0.017) and Compound 1+ranibizumab (p=0.013) groups. When the results were stratified by baseline IOP, higher baseline IOP was consistently associated with larger IOP reduction. This result is consistent with decreased resistance in the pressure-dependent, CO pathway (FIG. 1C). In FIG. 1C, patient level IOP change from baseline is expressed as a function of baseline IOP (<16, ≥16 or ≥18; placebo adjusted mean±standard error). Higher baseline IOP was consistently associated with larger IOP reduction consistent with decreased resistance in the pressure-dependent conventional outflow pathway.

Example 2: Subcutaneous Administration of Compound 1 Reduces IOP in Ocular Normotensive Patients with Diabetic Macular Edema A Phase 2, randomized placebo-controlled, double-masked human clinical trial was conducted to assess the safety and efficacy of subcutaneously administered Compound 1 (15 mg once daily or 15 mg twice daily for 12 months; sodium salt) in patients with moderate to severe non-proliferative diabetic retinopathy (NPDR).

Methods.

Eligible subjects were aged 18 to 80 years with moderate to severe NPDR. The major inclusion criteria for the qualified eyes included Early Treatment Diabetic Retinopathy Study (ETDRS) Severity Score≥43 and ≤53, no evidence of central involved diabetic macular edema (DME) and ETDRS≥70 letters using the ETDRS visual acuity charts. Study eye ocular exclusion criteria included uncontrolled glaucoma defined as IOP≥30 mm Hg on maximum IOP reduction therapy.

Subjects were randomized 1:1:1 to either Compound 1, 15 mg once daily (QD), Compound 1, 15 mg twice daily (BID), or placebo BID treatment groups. Subjects self-administered the masked study medication (Compound 1 or placebo) supplied as sterile pre-filled single-use syringes. Subjects visited the clinical site monthly during the 48-week treatment period. A battery of comprehensive ophthalmic evaluations including IOP assessments were conducted every 12-weeks with either applanation tonometry or Tono-Pen® and the methodology was consistent throughout the study. On Day 1 and Week 24, IOP was measured prior to dosing.

IOP data were analyzed using a mixed-model repeated measures ANCOVA, with visit as the repeated measure within subject. The model included change from baseline as the dependent variable. The p-value from the model was adjusted by baseline IOP.

Results.

Figure 1D:
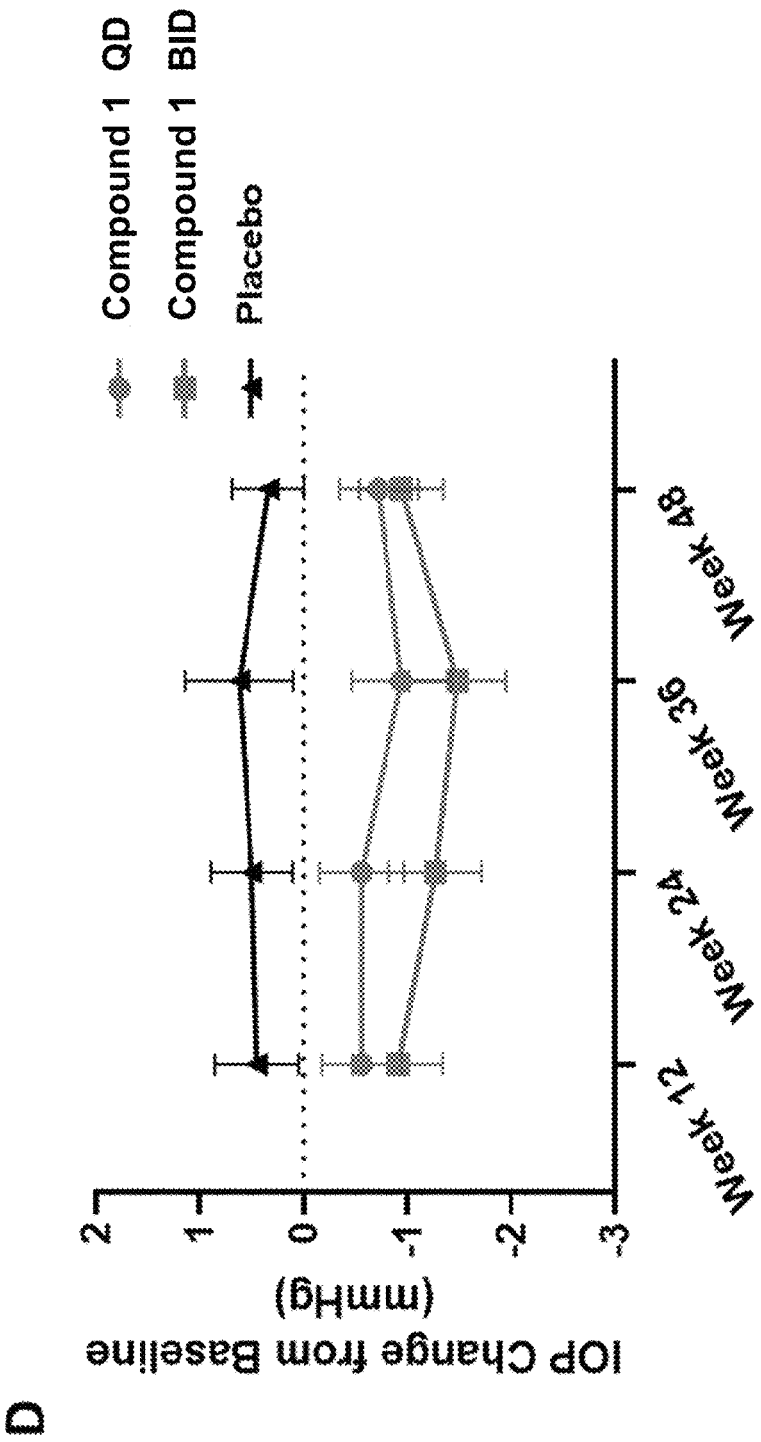
FIG. 1D illustrates patient level IOP mean change from baseline over time in all patients receiving Compound 1 15 mg QD, Compound 1 15 mg BID, and placebo.

The effect of Compound 1 on intraocular pressure (mmHg) averaged over both eyes (Study and Fellow eyes) in diabetic subjects with normal IOP is summarized in FIG. 1D and TABLE 5.

TABLE 5

|  | Compound 1 QD | Compound 1 BID | Placebo |
| --- | --- | --- | --- |
| Baseline mean IOP (SD) | 15.9 (2.85) | 15.6 (2.60) | 15.0 (3.82) |
| Week 12 | 15.3 (2.75) | 14.6 (2.93) | 15.4 (2.99) |
| Change from BL | −0.56 (2.83) | −0.91 (3.20) | 0.45 (3.00) |
| Week 24 | 15.3 (2.90) | 14.2 (2.60) | 15.4 (2.89) |
| Change from BL | −0.56 (2.99) | −1.27 (3.31) | 0.50 (2.91) |
| Week 36 | 14.9 (3.58) | 14.0 (2.74) | 15.5 (2.84) |
| Change from BL | −0.94 (3.39) | −1.48 (3.48) | 0.62 (3.85) |
| Week 48 | 15.2 (2.84) | 14.6 (2.73) | 15.2 (2.85) |
| Change from BL | −0.72 (2.80) | −0.94 (3.00) | 0.34 (2.58) |
| Change from BL (p-value) | 0.041 | <0.001 | 0.50 |
| vs. Placebo (p-value) | 0.055 | <0.001 |  |

BL = Baseline;
sd = standard deviation

FIG. 1D depicts Patient level IOP (average of both eyes, within each patient) mean change from baseline over time in all patients receiving Compound 1, 15 mg QD (circles), Compound 1, 15 mg BID (squares), and placebo (triangles). The IOP change from baseline was statistically significant for the Compound 1 QD (p=0.041) and BID (p<0.0001) treatment groups, but not for the placebo group (p=0.502). The mean reduction in IOP in the Compound 1 BID group compared to placebo was 1.15 mmHg (p=0.0002). The mean reduction in IOP in the Compound 1 QD group 0.70 mmHg compared to placebo was (p=0.0552) (MMRM ANCOVA).

Compound 1 reduced IOP at all post-baseline timepoints, whereas a slight elevation in IOP was observed in the placebo-treated group. A relationship between Compound 1 dose and IOP lowering was observed, with a larger reduction for the BID dose at all timepoints, ranging from 0.22 to 0.71 mmHg. A mixed-effect model, repeated measure analysis showed that the change from baseline was statistically significant for the Compound 1 QD (p=0.041) and BID (p<0.0001) treatment groups, but not for the placebo group (p=0.502). The 1.15 mmHg mean reduction in IOP in the Compound 1 BID group compared to placebo was statistically significant (p=0.0002). However, the 0.70 mmHg reduction in the Compound 1 QD group compared to placebo showed a trend that did not reach statistical significance (p=0.0552). At the 24-week visit, the AM dose was withheld until after the IOP measurement so that drug pharmacokinetics could be assessed. Despite a dosing interval of ~12 hours or 24 hours for the BID and QD dose groups, respectively, the IOP reduction was similar to other timepoints in which the AM dose was not withheld, suggesting a sustained IOP lowering effect of Compound 1.

Example 3: IOP Effects of Subcutaneous Compound 1 in Extended 48-Week Trial 167 patients with moderate to severe non-proliferative diabetic retinopathy (NPDR) without diabetic macular edema (DME) and a visual acuity of 20/40 or better were enrolled in a 48-week study of the effect of Compound 1 (sodium salt) in the treatment of NPDR. The IOP was measured at baseline, and at weeks 12, 24, 36, and 48. The trial consisted of three study arms: 1) patients receiving 15 mg of Compound 1 subcutaneously BID; 2) patients receiving placebo subcutaneously QD, and 15 mg of Compound 1 subcutaneously QD; and 3) patients receiving a placebo subcutaneously BID. The results are summarized in FIG. 2.

Figure 2:
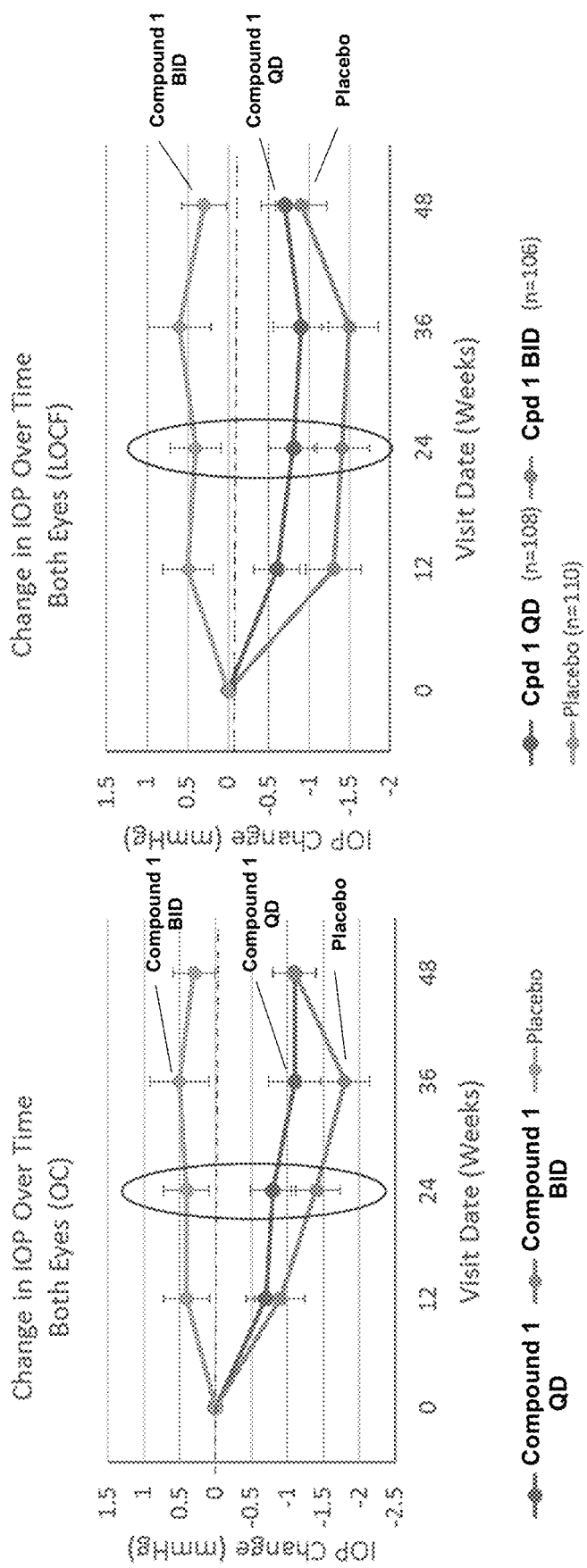
FIG. 2 illustrates the effect of Compound 1 administered once daily (QD) and twice daily (BID) over 48 weeks on IOP in patients with severe non-proliferative diabetic retinopathy (NPDR) without diabetic macular edema (DME).

Both panels of FIG. 2 demonstrate IOP reduction in both QD and BID groups with a trend favoring dose dependence. Week 24 IOP measured predose (ovals) show a persistent IOP effect that supports QD dosing (BID>12 hr since prior dose; QD>24 hr since prior dose). MMRM (Mixed-Effect Model Repeated Measures) Analysis LOCF: Within Treatment Change from Baseline—Compound 1 QD p=0.04; Compound 1 BID p<0.0001; Compound 1 Group vs Placebo—Compound 1 QD p=0.0553; Compound 1 BID p<0.0002.

Figure 3A:
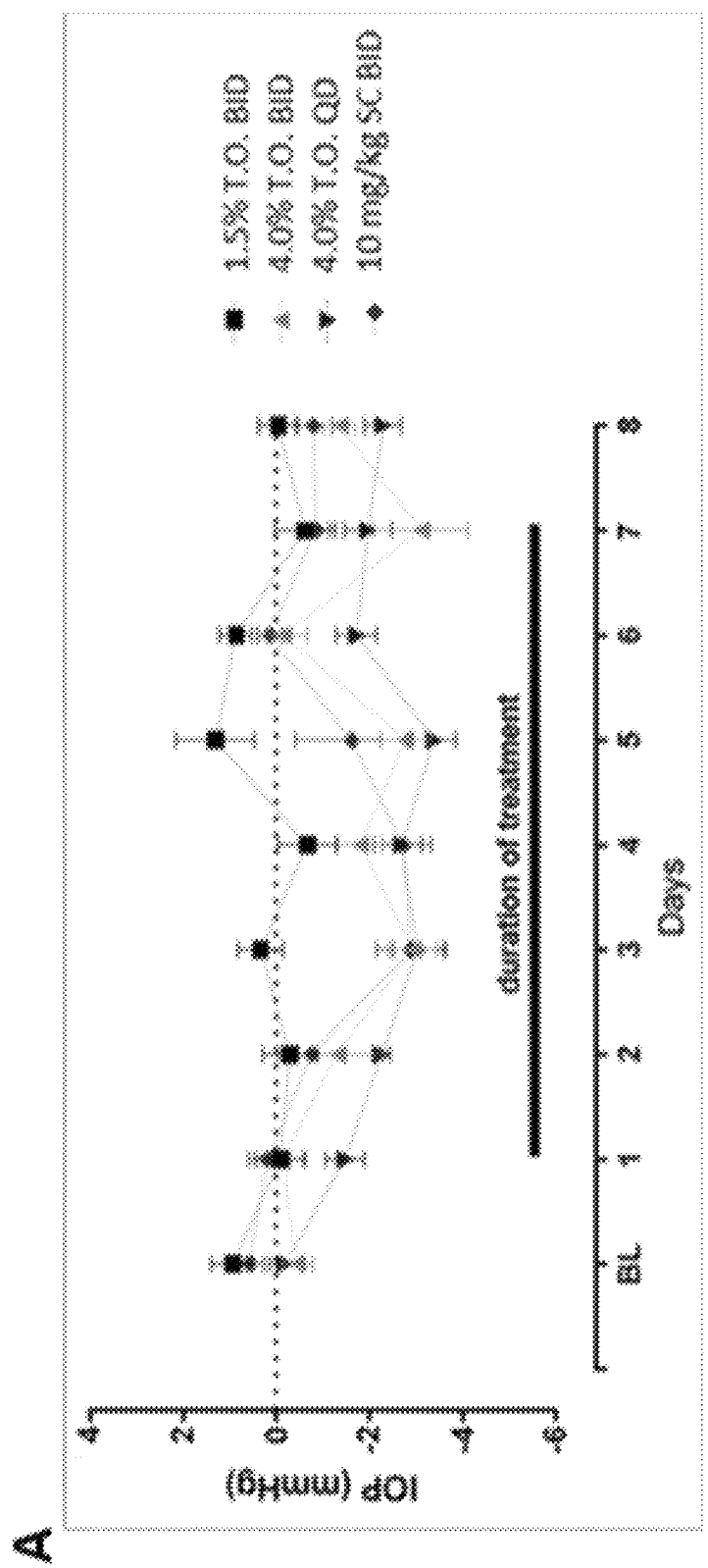
FIG. 3A illustrates daily mean changes in IOP relative to vehicle control over 8 days in ocular normotensive New Zealand White rabbits administered ocular topical or subcutaneous Compound 1.
Figure 3B:
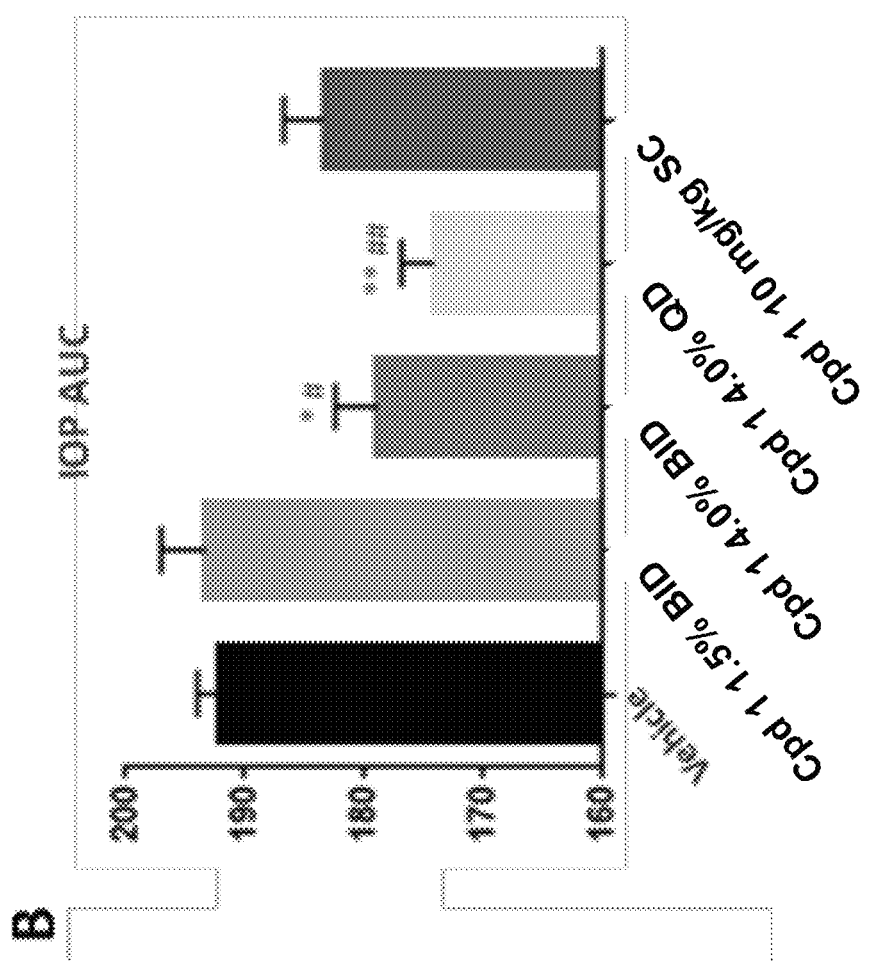
FIG. 3B illustrates the area under the curve (AOC) for IOP values over 7 days of 4% Compound 1 TO, dosed QD or BID in ocular normotensive New Zealand White rabbits.
Figure 3C:
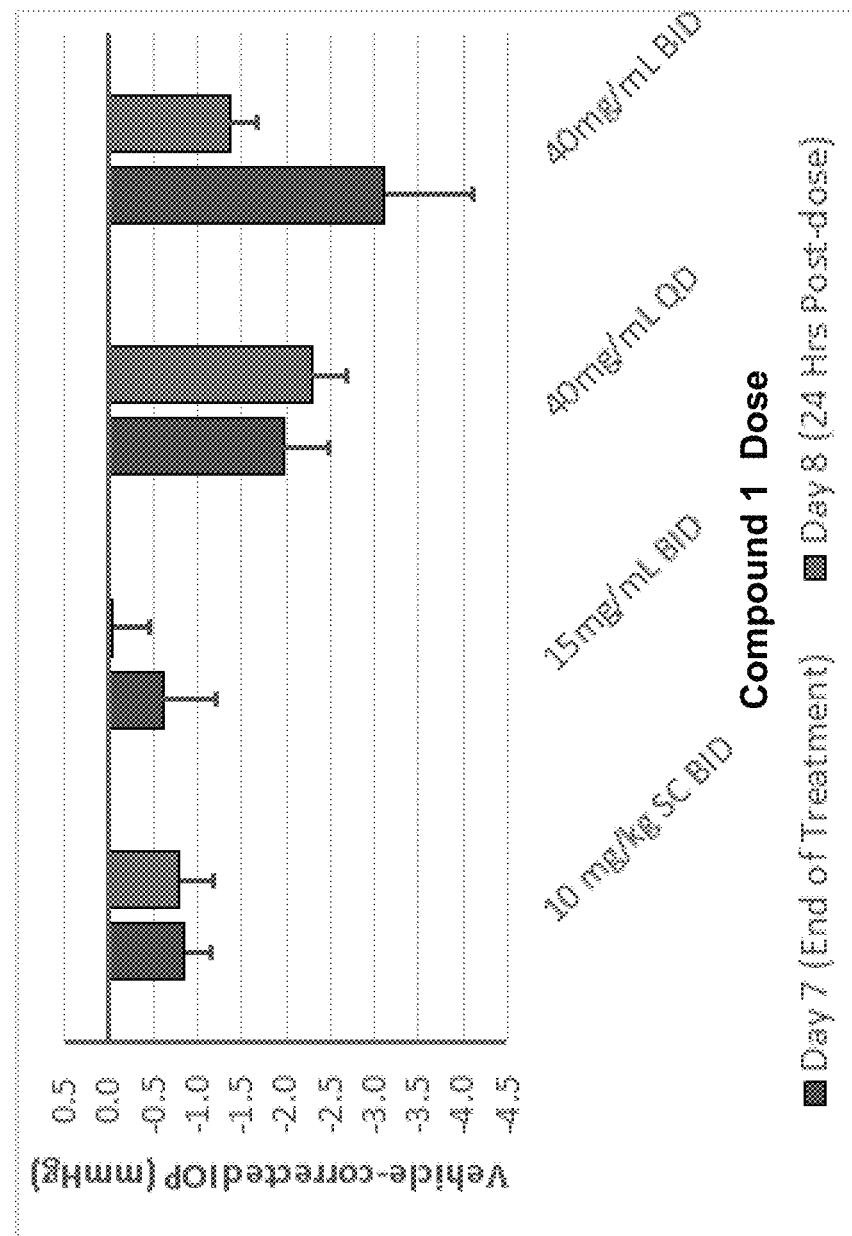
FIG. 3C illustrates the decrease in IOP at end of treatment (7 days) and 24 hours after the last dose (Day 8) relative to Day 0 baseline in New Zealand White rabbits administered ocular topical or subcutaneous Compound 1.

Example 4: Topical Ocular Administration of Compound 1 Reduces IOP in Ocular Normotensive Rabbits To examine the effect of Compound 1 on IOP, Compound 1 was delivered either by subcutaneous injection, or by topical drops to ocular normotensive New Zealand White rabbits, and IOP was followed over time (FIGS. 3A-3C). For this study, 25 female New Zealand White rabbits were administered the sodium salt of Compound 1 for seven days QD or BID topically (30 µL drop) into both eyes, or twice daily subcutaneously, or vehicle twice daily topically into both eyes. Eye drops (4% Compound 1 or vehicle) were administered, with study staff masked to treatment.

Five dose groups (5 rabbits per group) were tested: 1) vehicle control—15% HPβCD (+1% dextrose); 2) 1.5% (15 mg/mL) Compound 1 BID; 3) 4% (40 mg/mL) Compound 1 BID; 4) 4% (40 mg/mL) Compound 1 QD; and 5) 10 mg/kg (40 mg/mL) Compound 1 administered subcutaneously BID.

IOP measurements were performed at baseline (prior to the start of dosing), and once daily on days 2-8. Prior to performing IOP measurements, 1 to 2 drops of a 0.5% proparacaine solution were applied to the eye as a topical anesthetic. IOP measurements were performed with a pneumotonometer 2 hours after morning dosing. The only exceptions were Day 8 measurements, which were performed 24 hours after the final dose.

IOP data were analyzed using a mixed-design two-factor ANOVA, with time as the within-subjects factor and treatment as the between-subjects factor. IOP values for Day 7 and Day 8 were analyzed using one-way ANOVA. The change from baseline IOP on Day 7 and on Day 8 was calculated for each animal, and the resulting values were analyzed using one-way ANOVA. Area under the curve (AUC) was calculated for all morning IOP measurements throughout the study for each group; AUC values for the different groups were analyzed using one-way ANOVA. Where appropriate, post hoc testing was performed using Tukey's multiple comparisons tests. The level of significance was set at 0.05.

Topical ocular administration of 4% Compound 1 QD and BID had a significantly larger IOP-lowering effect than topical dosing of the vehicle control or of 1.5% Compound 1 BID (p<0.001; ANOVA).

A steady-state effect on IOP was observed by Day 3 following daily topical ocular dosing of 4.0% Compound 1. A significant reduction in IOP persisted on Day 8, 24 hours after the last dose for the two high-dose topical ocular Compound 1 groups. While a significant maximum IOP-lowering effect of 10 mg/kg BID subcutaneous injection was observed relative to vehicle control, on Days 3 and 4 (p<0.01), the effect did not persist in rabbits by the last day of dosing (Day 7) and did not differ from vehicle control or 1.5% Compound 1 BID.

No adverse effects of Compound 1 were observed on local tolerance using slit lamp biomicroscopy during the study. McDonald-Shadduck (modified) scoring upon ophthalmologic examination suggested mild conjunctival congestion (Score '+1') on Day 1 in some rabbits in each group, with a decreased incidence of this finding on Day 4. These findings did not persist 24 hr after dosing (Day 8).

IOP reduction in rabbits was larger with topical ocular administration than with subcutaneous administration. The result supports a local effect of Compound 1 on IOP regulation.

FIG. 3A illustrates the daily mean changes in IOP relative to vehicle control. Decreases in IOP at 4% Compound 1 topical ocular (TO) QD or BID persisted 24 hours post-dose (Day 8). As depicted in FIG. 3B, the calculated area under the curve for IOP values over 7 days of 4% Compound 1 TO, dosed QD or BID, was statistically-significantly lower than were the IOP AUC values for TO vehicle control (Vehicle) or 1.5% TO BID or 10 mg/kg subcutaneous (SC) BID.

n=5/group; * p≤0.05 vs Vehicle; **p≤0.01 vs Vehicle; #p≤0.05 vs Compound 1 1.5% BID; ##p≤0.001 vs Compound 1 1.5% BID.

As shown in FIG. 3C, Topical ocular dosing of Compound 1 yielded larger decreases in IOP than did subcutaneous dosing in New Zealand White rabbits. The observed decrease in IOP persisted for 24 hours after the last dose.

Example 5: Topical Ocular Administration of Compound 1 Reduces IOP and Increases Outflow Facility in Ocular Normotensive Mice The effect of Compound 1 on IOP in naïve eyes of $C_{57}$ mice was monitored for three days after once daily topical dosing. Additionally, due to the role of the Tie-2 pathway in SC and the role of the conventional outflow pathway in regulating IOP, IOP lowering effects of Compound 1 on outflow facility were assessed in mouse eyes.
Methods.

Mice were handled in accordance with acceptable animal care and use guidelines. C57BL/6 (C57) mice were bred/housed in clear cages and kept in housing rooms at 21° C. with a 12 h: 12 h light-dark cycle. Mice were examined at ages between 4 to 6 months old.
IOP Measurements.

Each animal was randomly assigned to receive one masked treatment (eye drops, 4% Compound 1 or vehicle) in one eye and the other masked treatment in the contralateral eye once daily for three consecutive days. IOPs of both eyes were measured prior to eye drop administration using rebound tonometry between 11 am and 1 pm daily. After collecting IOP measurements on the third day, a final drop of Compound 1 or placebo was administered and TOP was measured again 2 and 4 hours later. For TOP measurements, mice were anesthetized with ketamine (60 mg/kg) and xylazine (6 mg/kg). TOP was immediately measured as the mice stopped moving, while drifting into light sleep, but before becoming anesthetized. Each TOP measurement that was recorded was a result of an average of six independent measurements per time point, giving a total of 36 measurements from the same eye.
Outflow Facility Measurements.

An iPerfusion system was used to measure outflow facility in mice. The system is designed to measure outflow facility in paired mouse eyes having low flow rates (nL/min). Outflow facility is a measure of the ability of aqueous humor to flow from the trabecular meshwork to maintain a steady state TOP.

After three days of treatment with either Compound 1 or placebo, eyes were enucleated, and outflow facility was measured in a masked fashion. Briefly, mice were euthanized using isoflurane and freshly enucleated, paired mouse eyes were mounted on two stabilization platforms in temperature-controlled perfusion chambers by using a small amount of cyanoacrylate glue. The perfusion chambers were filled with pre-warmed D-glucose in phosphate-buffered saline (DBG, 5.5 mM) and temperature regulated at 35° C. A glass microneedle was back filled with either vehicle or 10 µM Compound 1 in a masked manner, matching topical treatments described in EXAMPLE 4. Microneedles were connected to two parallel perfusion systems and were inserted into the anterior chamber of each eye using micromanipulators visualized using a stereomicroscope.

Both eyes of the mice were perfused at 9 mmHg for 45-60 min to allow acclimatization and to deliver the drug or vehicle to the outflow pathway, followed by 9 sequential pressure steps of 4.5, 6, 7.5, 9, 10.5, 12, 15, 18, and 21 mmHg. The outflow from the eye was measured at multiple pressures to calculate the outflow facility.

A non-linear flow-pressure model was used to account for the pressure dependence of outflow facility in mice. The reference facility was analyzed at a reference pressure of 8 mmHg, which approximates the physiological pressure drop across the conventional outflow pathway in living mice. A paired two-tailed t-test was used to determine difference in facility between paired eyes was statistically significant.
Results.

Figure 4A:
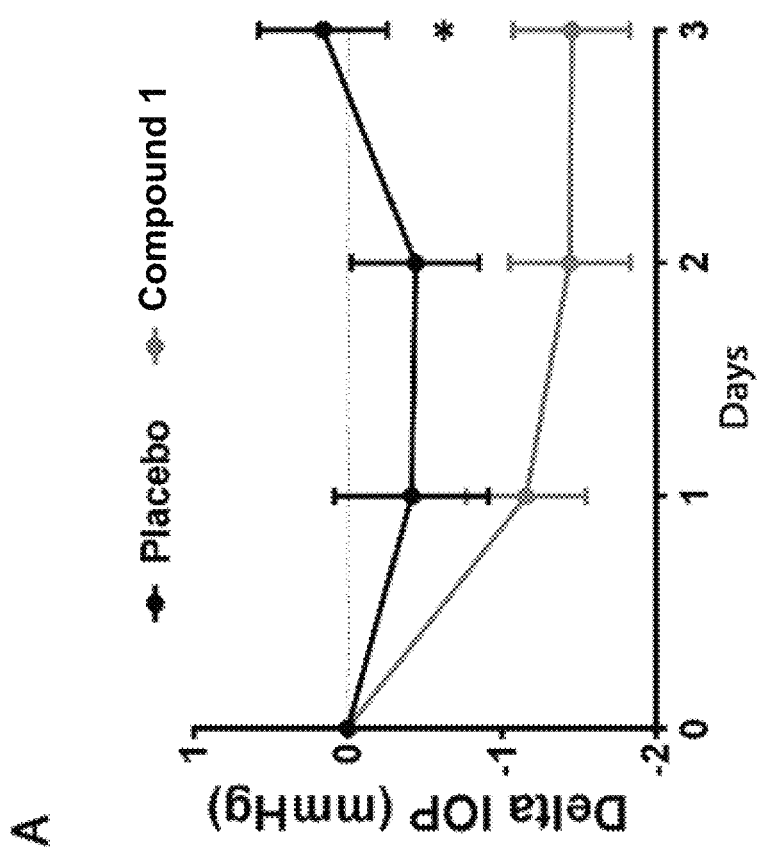
FIG. 4A illustrates the change in IOP observed in C57 mice administered QD 4% Compound 1 (w/w) over 3 days.
Figure 4B:
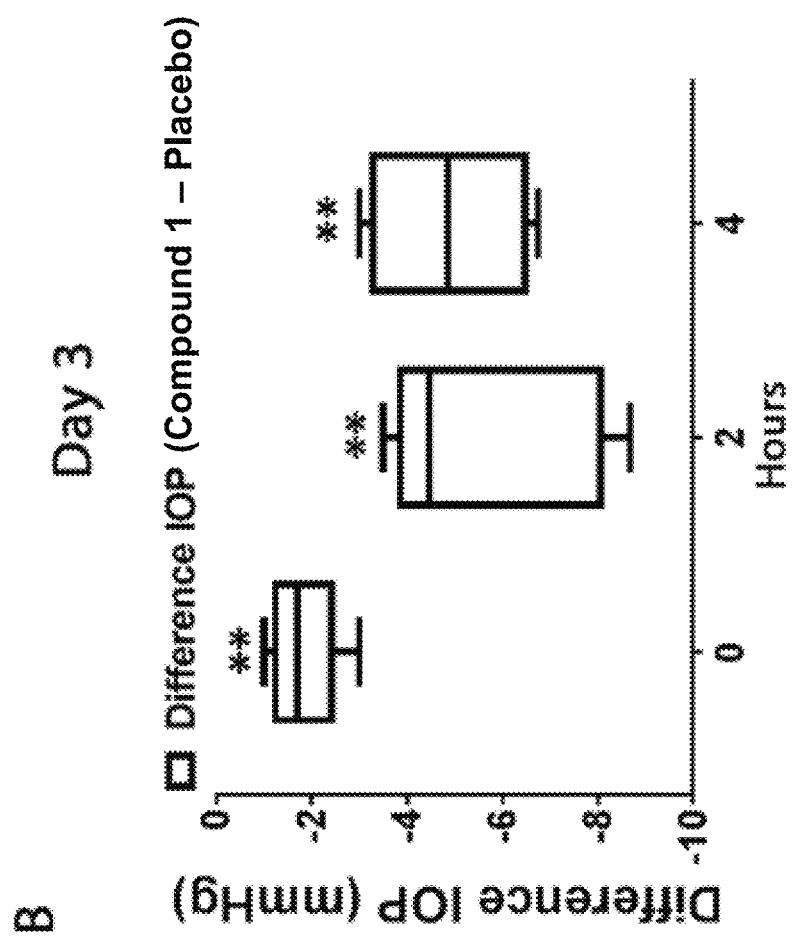
FIG. 4B illustrates the difference in IOP relative to placebo observed in C57 mice administered QD 4% Compound 1 (w/w) over 3 days.

Change in pretreatment IOP was assessed (mean±standard error, n=14) by comparing pre-treatment (Day 0) with treatment (placebo or Compound 1). IOP was measured once per day for three consecutive days prior to dosing. As shown in FIG. 4A, Compound 1 decreased IOP over time relative to Day 0 IOP, by −0.74±0.43 mmHg and −1.00±0.27 mmHg when measured just prior to dosing on Days 1 and 2, respectively, to a change in IOP of −1.6±0.3 mmHg measured prior to dosing on Day 3. Since IOP lowering was maximal and significant on Day 3 (p=0.017), IOP was assessed at two additional time points on Day 3, at 2 and 4 hours after treatment. IOP lowering was more pronounced at these additional time points, with a significant decrease of ~30% (mean±SE: −3.85±1.1 mmHg at 2 hours and −3.1±0.6 mmHg at 4 hours when compared to both Day 0 pretreatment and placebo treatment; −5.66±1.0 mmHg at 2 hours and −4.87±0.75 mmHg at 4 hours, when compared to only placebo-treated eyes; p<0.01 by paired student t test) (FIG. 4B).

Figure 4C:
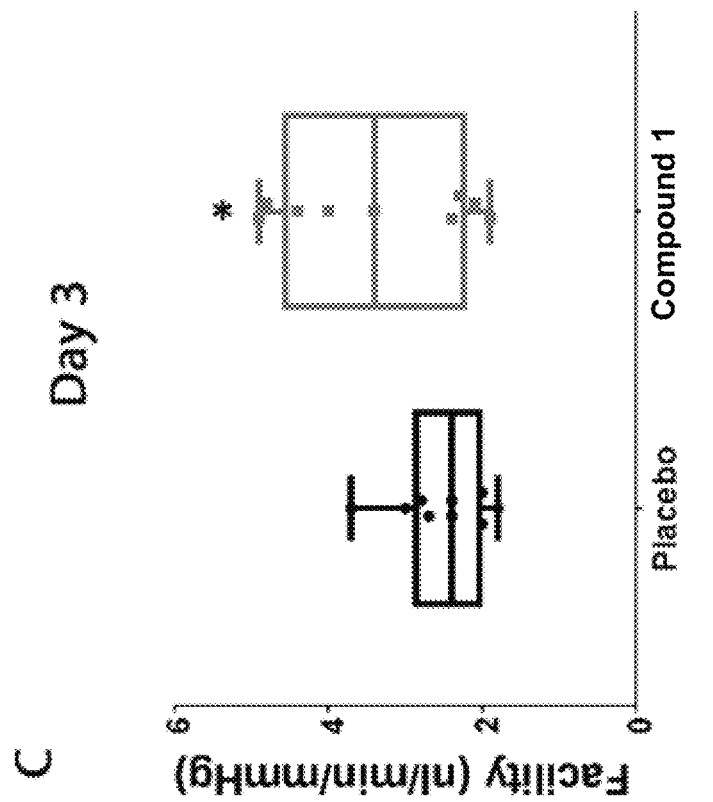
FIG. 4C illustrates outflow facility observed in mouse eyes that had been dosed for three days QD with 4% Compound 1 (w/w) and placebo.

Outflow facility (central bar is median, the range shows min to max, individual data points are indicated, n=9) of eyes treated with Compound 1 was assessed for three days (*p≤0.05, **p≤0.01), comparing drug to placebo-treated contralateral eyes. As shown in FIG. 4C, Compound 1 significantly increased outflow facility compared to control by 33% (3.4±0.4 vs. 2.5±0.2 nL/min/mmHg, p=0.047).

The increase in outflow facility was consistent with maximal IOP effects of VE-PTP inhibition in both mice and rabbits. The similarity between the mouse and human CO pathway with both having a continuous SC, suggests that the IOP lowering effect in humans can be mediated by increased outflow facility.

Example 6: VE-PTP and Tie-2 Expression Both Localize to Schlemm's Canal

To determine potential conventional outflow targets of Compound 1, VE-PTP expression was assessed in anterior eye segments of mice.
Methods.
Treatment of Mice with Compound 1.

VE-PTP expression was assessed in the endothelium of SC in VE-PTP knock-in reporter mice expressing a nuclear-localizing β-galactosidase from the endogenous VE-PTP promoter (VE-PTP+/mut). C57BL/6JRj mice were also used in the experiments as control animals. Mice were anaesthetized using ketamine (125 mg/kg) and xylazine (12.5 mg/kg). 10 µL of Compound 1 eye drop solution (4% Compound 1) or vehicle was applied to each eye. Mice were euthanized 1 hour following dosing, and the eyes were processed for immunofluorescence analysis to detect Tie-2 phosphorylation.
Antibodies.

The following primary antibodies were used for immunofluorescence staining at the indicated concentrations: VE-PTP (rat-a-mouse-VE-PTP, clone 109.1, 10 µg/mL), VE-cadherin (rabbit-a-mouse-VE-cadherin, pAB42), Prox1

(goat-anti-human-Prox1, AF-2727, 2 μg/mL); PECAM-1 (rat-anti-mouse PECAM-1, clone 1G5.1 (3 μg/mL)+clone 5D2.6 (1 μg/mL); Tie-2 (goat-anti-mouse-Tie-2, AF762, 5 μg/mL); phospho-Tie-2 (rabbit-a-pY992-Tie2, AF2720, 10 μg/mL). The following Alexa Fluor-labelled secondary antibodies were used at a concentration of 2 μg/mL: donkey-anti-rat-IgG-Alexa-488 (A-21208); donkey-anti-goat-IgG-Alexa-568 (A-11057); donkey-anti-goat-IgG-Alexa-647 (A-10042); donkey-a-rabbit-IgG-Alexa-568 (A-21447).

Detection of β-Galactosidase Activity.

For detection of β-galactosidase activity, enucleated eyes were fixed in 2% PFA for 15 min at RT, followed by incubation in X-Gal staining solution (1 mg/mL X-Gal, 5 mM $K_4Fe(CN)_6$, 5 mM $K_3Fe(CN)_6$, 2 mM $MgCl_2$ in PBS) over night at 37° C. The next day, corneas were isolated, permeabilized, and blocked in blocking buffer (5% donkey serum, 0.3% Triton-X-100 in PBS) for 1 h at RT and incubated with primary antibodies in blocking buffer overnight at 4° C. After 6 washes in washing buffer (0.3% Triton-X-100 in PBS) for 15 min at RT, corneas were incubated with secondary antibodies in blocking buffer for 4 h at RT in the dark, followed by 6 washes in washing buffer for 15 min at RT before mounting in DAKO fluorescent mounting medium. Analysis was performed using a confocal microscope.

Immunofluorescence Staining.

For immunofluorescence staining of whole-mount cornea preparations, the vasculature of mice was perfused with PBS followed by 1% PFA via the left ventricle. Eyes were enucleated, and eyeballs were fixed in 4% PFA for 30 min at RT, followed by incubation in fixative solution (1% PFA, 0.1% Triton-X-100, 0.1% NP-40 in PBS) for 30 min at RT. Corneas were isolated from the fixed eyeballs, permeabilized, and blocked in blocking buffer (5% donkey serum, 0.2% BSA, 0.2% Triton-X-100 in PBS) for 1 h or overnight at RT. Incubation with primary antibodies diluted in blocking buffer was performed overnight at RT. After 6 washes with washing buffer (0.3% Triton-X-100 in PBS) for 60 min at RT, corneas were incubated with secondary antibodies diluted in blocking buffer overnight at RT, followed by 6 washes in washing buffer for 30 min at RT before mounting in DAKO fluorescent mounting medium. Analysis was performed using a confocal microscope. For detection of phosphotyrosine, 1 mM sodium orthovanadate was added to all buffers.

For immunofluorescence staining of cryostat sections of eyeballs, the vasculature of mice was perfused with PBS followed by 1% PFA via the left ventricle. Eyes were enucleated, and eyeballs were fixed in 2% PFA for 15 min at RT, followed by washing 3×5 min with PBS, embedded in optimal cutting temperature (OCT) medium (Neg-50), and cut at −16° C. Sections were incubated with 10 μg/mL mAb 109.1 against VE-PTP or 5 μg/mL pAb42 against mouse VE-cadherin, followed by secondary antibodies.

Histological Analysis.

For histological analysis of adult murine eyes, the vasculature of mice was perfused with PBS followed by 1% PFA via the left ventricle. Eyes were enucleated, and eyeballs were fixed in 2% PFA for 15 min at RT, followed by incubation in X-Gal staining solution over night at 37° C. Eyes were post-fixed in 4% PFA for 2 h at RT, embedded in OCT (optimal cutting temperature compound), and frozen. Frozen blocks were cut into 10 μm sections. Analysis was performed using a confocal microscope.

Results.

Figure 5A:
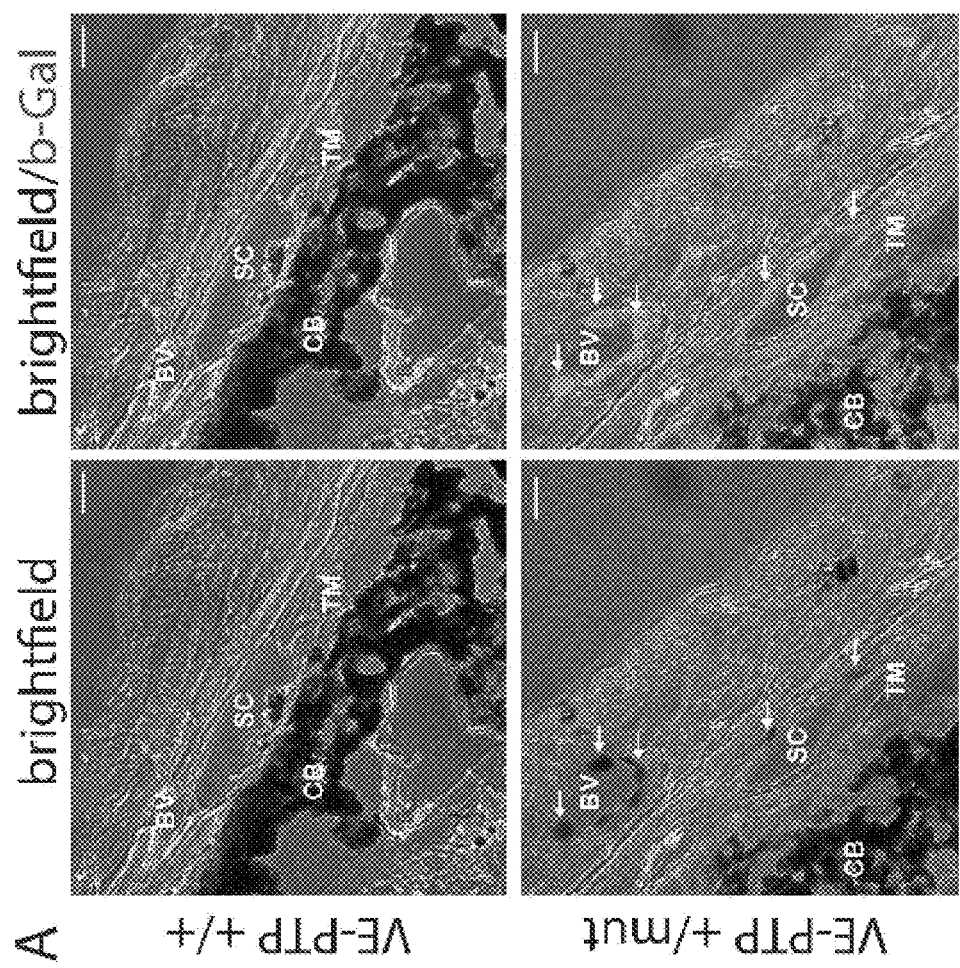
FIG. 5A illustrates VE-PTP expression in Schlemm's canal endothelial cells in adult murine eyes of either wild-type (VE-PTP+/+) or heterozygous knock-in mice (VE-PTP+/mut).
Figure 5B:
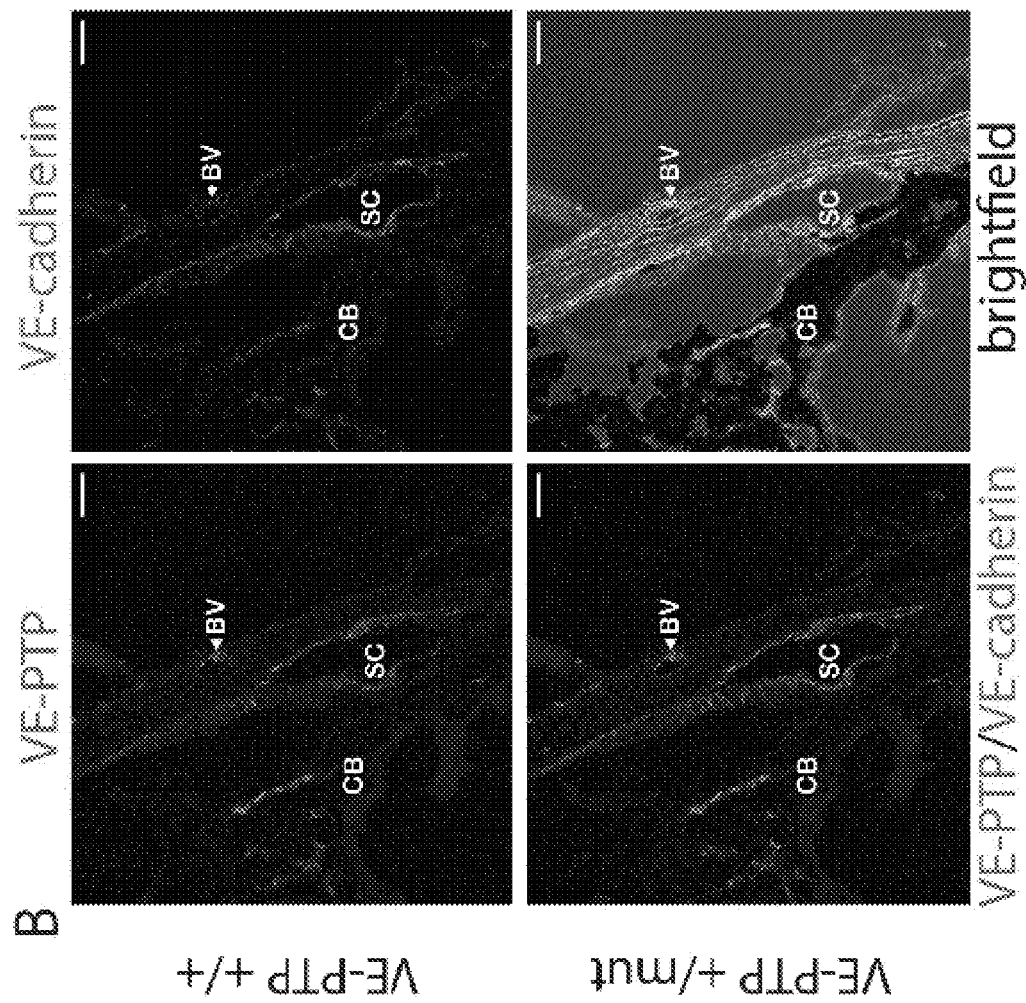
FIG. 5B illustrates VE-PTP and VE-cadherin expression in sagittal sections of adult VE-PTP$^{+/+}$ murine eyes stained with antibodies specific for VE-PTP (top left) or VE-cadherin (top right), and VE-PTP and VE-cadherin expression in heterozygous knockout mice (VE-PTP$^{+/mut}$, bottom).

Adult murine eyes of either wildtype (VE-PTP$^{+/+}$) or heterozygous knock-in mice expressing β-Galactosidase under the VE-PTP promoter (VE-PTP$^{+/mut}$) were cross-sectioned after X-Gal staining to visualize VE-PTP expression. As shown in FIG. 5A, β-galactosidase activity was detected in nuclei of SC but not the TM in the VE-PTP$^{+/mut}$ mice. In parallel, sagittal cryostat sections of adult murine eyes were stained with monoclonal antibodies specific for VE-PTP (FIG. 5B, top left) or VE-cadherin (FIG. 5B, top right).

Figure 5C:
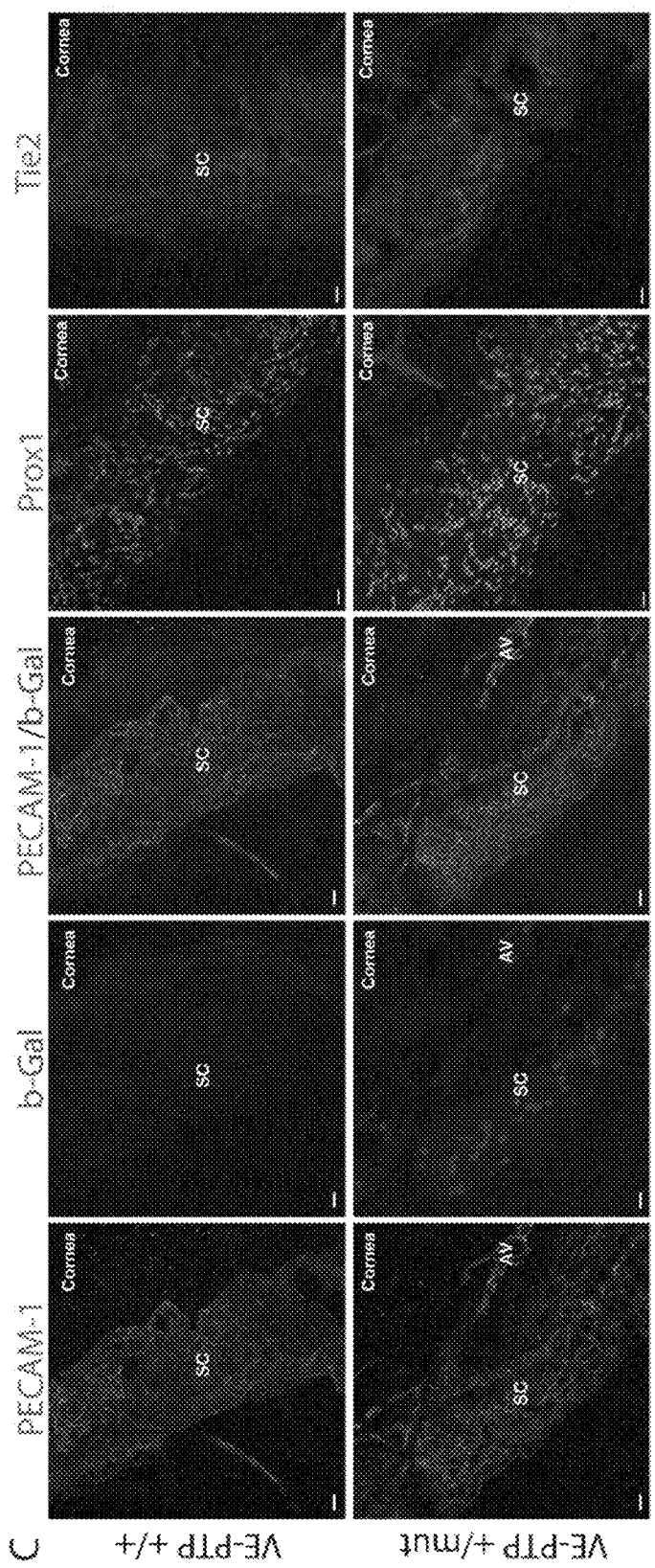
FIG. 5C illustrates an immunofluorescence analysis of adult murine eyes of VE-PTP+/+ or VE-PTP+/mut mice stained for PECAM-1, Prox-1 and Tie-2.

In a whole mount immunofluorescence analysis of adult murine eyes of VE-PTP$^{+/+}$ or VE-PTP$^{+/mut}$ mice, enucleated eyes were stained as whole mounts with X-gal or with antibodies to detect PECAM-1, Prox-1 and Tie-2. The entire thickness of the limbus was visualized by confocal imaging. Subsets of optical sections containing SC are shown. SC endothelial cells expressed PECAM-1, Prox1, and Tie-2 (FIG. 5C).

Figure 5D:
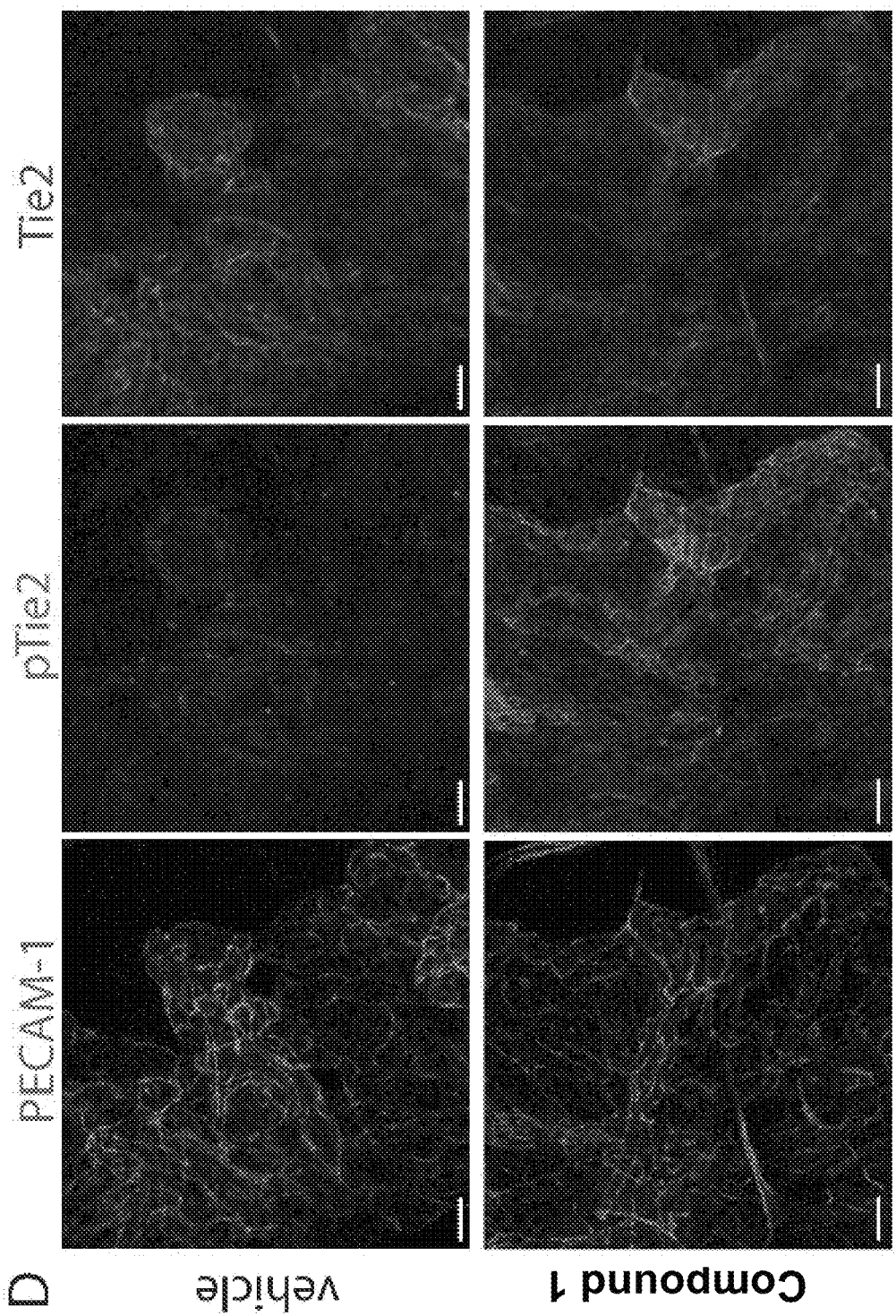
FIG. 5D illustrates whole mount immunofluorescence staining of adult murine eyes topically treated with either Compound 1 or vehicle for 1 h and stained for PECAM-1, pY992-Tie-2 and total Tie-2.

To evaluate VE-PTP mediated signaling, tyrosine phosphorylation and activation of Tie-2 in SC following VE-PTP inhibition was assessed one hour following a single topical ocular administration of Compound 1. Whole mount immunofluorescence staining of adult murine eyes topically treated with either Compound 1 or vehicle for 1 hr and stained for PECAM-1, pY992-Tie-2, and total Tie-2 was conducted. The entire thickness of the limbus was visualized by confocal imaging and subsets of optical sections depicting SC are shown in FIG. 5D (Scale bar: 20 μm; SC=Schlemm's canal; AV=aqueous vein. CB=ciliary body; BV=blood vessel; TM=trabecular meshwork).

As shown in FIG. 5D, staining of SC with an antibody specific for tyrosine phosphorylated Tie-2 was enhanced following topical ocular administration of Compound 1.

In line with the hybrid nature of the SC endothelium, VE-PTP was not homogeneously expressed when assessed by reporter gene expression, and expression levels appeared generally lower than in vascular endothelial cells. However, expression was found in all regions of SC including its inner wall.

The examples herein suggest that despite the expression of various endothelial markers on cells of the trabecular meshwork, the TM does not express Tie-2 or VE-PTP. observation suggests that the IOP lowering effect of Compound 1 can be mediated by the SC endothelia.

Figure 7:
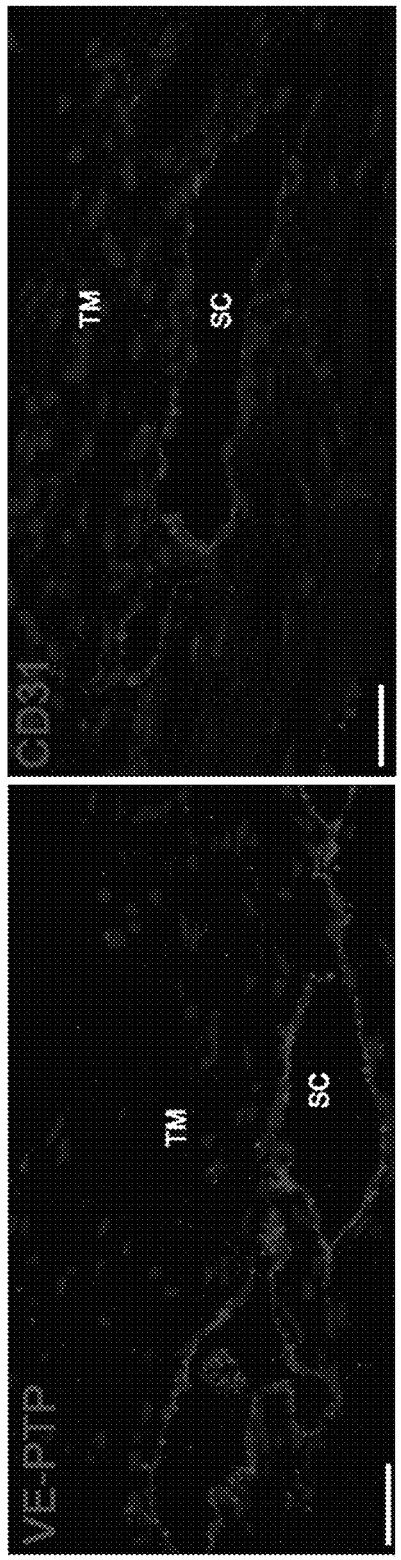
FIG. 7 shows that VE-PTP (HPTP-β) and CD31 expression was seen in human SC from human donor cells.

FIG. 7 shows VE-PTP (HPTP-β) expression in SC in human donor eyes. The left panel shows labelling of conventional outflow tissues from human donor eyes restricted to the endothelial cells of Schlemm's canal (SC) using antibodies specific for VE-PTP. The right panel shows selective staining of SC with antibodies against the vascular endothelial cell marker, CD31. The analysed sections underwent counterstaining with DAPI for cell nuclei localization. TM: trabecular meshwork, magnification bars=50 μm. A rabbit-anti-human VE-PTP antibody (hVE-PTP 1-8) was generated in rabbits against a recombinant form of the extracellular fibronectin type III-like domains 1-8 of human VE-PTP and affinity purified using the antigen.

Example 7: Topical Ocular Administration of Compound 1 Enhances Schlemm's Canal Area in Mice To determine whether inhibition of VE-PTP by ocular administration of Compound 1 has a beneficial effect on SC size in mice, 4-week old $C_{57}B16$ mice were treated twice daily for 4 weeks BID with eye drops (5 μL) containing 4% Compound 1 or vehicle. Prior to application of eye drops, mice were anaesthetized using an isoflurane evaporator. Whole mounts of corneas were stained for PECAM-1 (FIG.

Figure 6A:
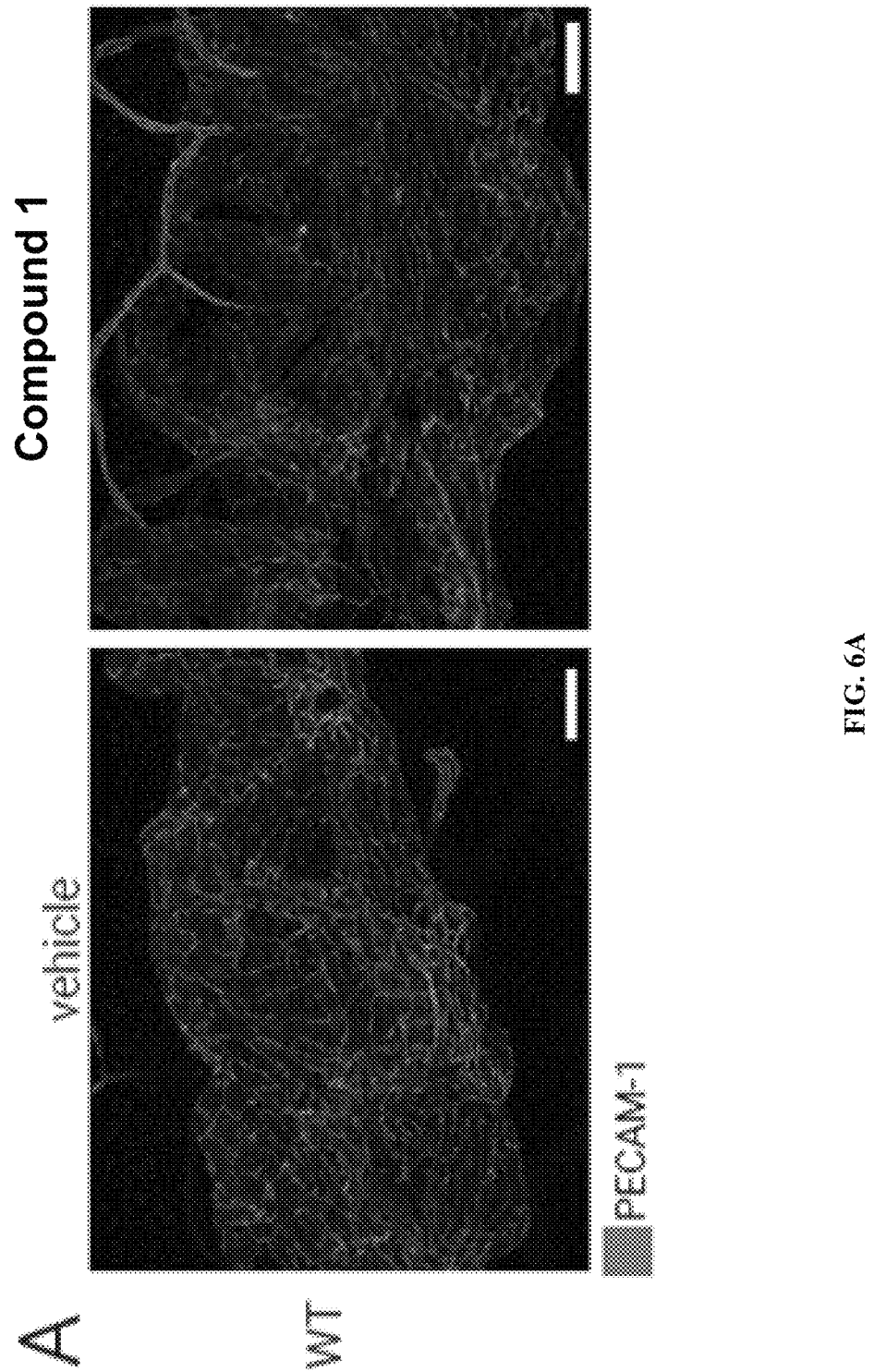
FIG. 6A illustrates relative sizes of PECAM-1 stained Schlemm's canals in 4-week old mice treated for 4 weeks BID with eye drops (5 μL) containing 4% Compound 1 or vehicle.
Figure 6B:
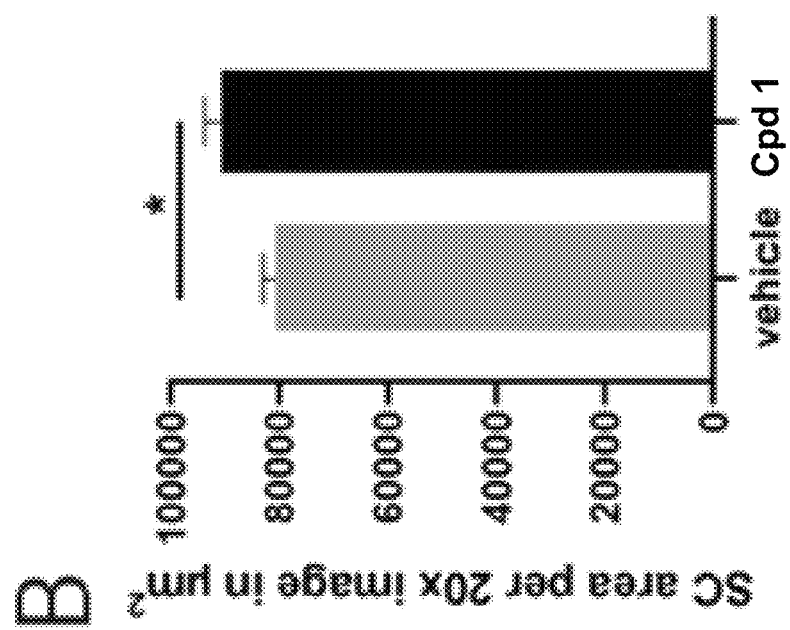
FIG. 6B summarizes the average SC area as measured in eyes of mice treated with 4% Compound 1 and vehicle.

6A) and SC areas were measured (FIG. 6B). As depicted in FIG. 6A, 20× fields shown represent an area of 146 μm². Images were captured as Z stacks with a step size of 0.89 μm and a pinhole of 1 airy unit, and are shown as maximum intensity projections. For quantification (FIG. 6B), SC area was measured in sixteen 20× images per condition for 4 eyes of 2 mice; *p≤0.05. Treatment with Compound 1 enhanced SC area by about 12.2% (±4.7%; p=0.022) with topical ocular Compound 1 treatment compared to vehicle.

Example 8: Phase IB Study to Study Effects of QD Versus BID Ocular Topical Dosing of Compound 1

A multi-center, double-masked, randomized, placebo-controlled, multiple-ascending dose (MAD) cohort study in up to 48 ocular normotensive patients was conducted. For subjects in cohort 1, IOP was between 12 mmHg and 23 mmHg (inclusive) in both eyes on Day −1. Cohorts 2-4 were limited to subjects with pre-treatment IOP≥16 mmHg and ≤23 mmHg in at least one eye and ≤23 mmHg in both eyes at all timepoints on two separate days of IOP assessment during screening. Subjects who received additional carbonic-anhydrase inhibiting drops or cholinergic agonist drops were washed-out for at least 7 days prior to Day −1.

Figure 8:
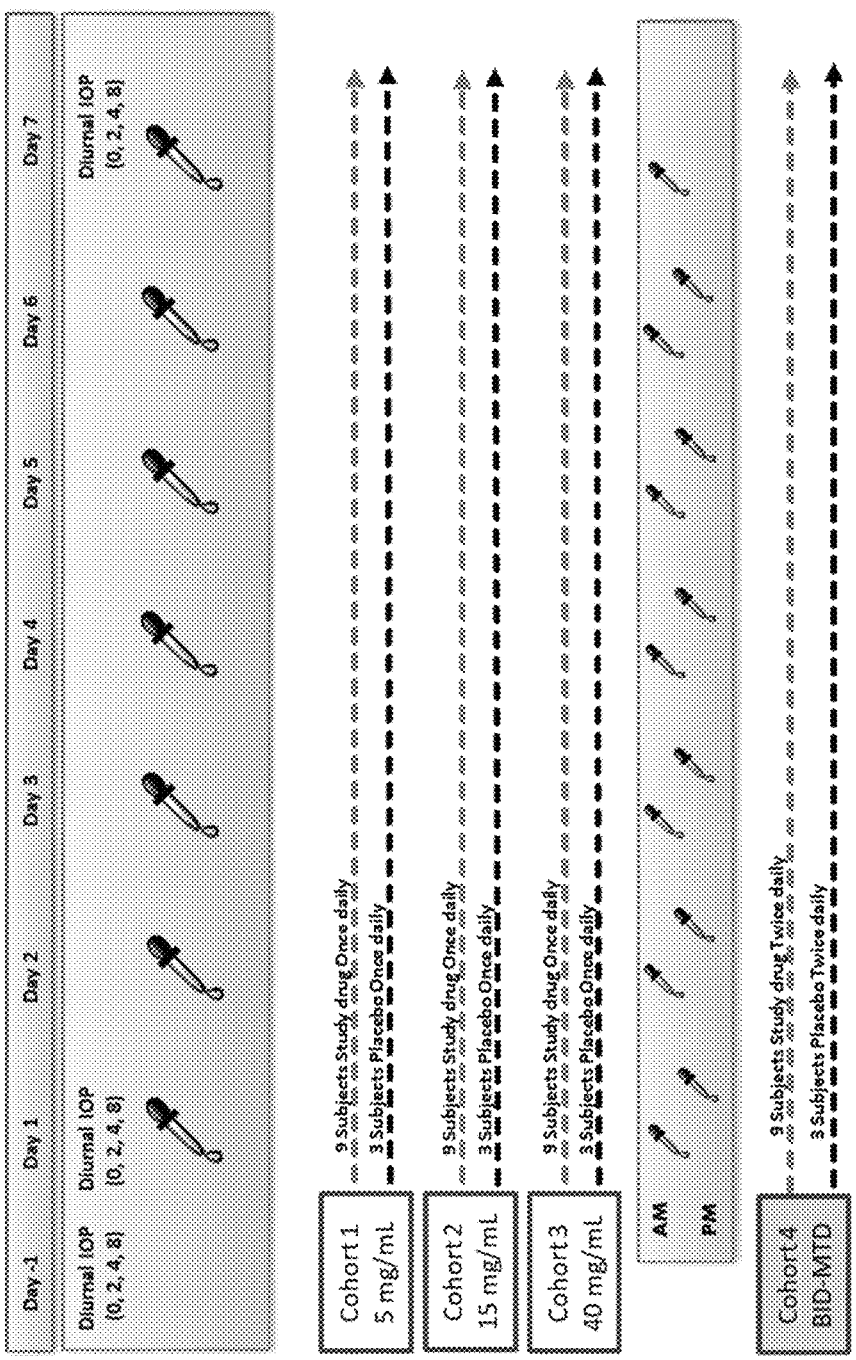
FIG. 8 provides a study design for a Phase 1B trial disclosed herein.

The study design is shown in FIG. 8. FIG. 8 shows that cohorts 1-3 received seven days of once daily dosing, while cohort 4 received 7 days of twice daily dosing. On Day −1 (day before first day of dosing), day 1, and day 7, for all cohorts, a baseline diurnal time point assessment of IOP in both eyes occurred at pre-dose, and 2, 4, and 8 hours post-dose relative to the planned dosing time the following day.

In cohorts 1-4, blood sampling for PK assessments was conducted on Day 1 and Day 6 at pre-dose, 0.25, 0.5, 1, 2, 4, 8, and 12 hours post-dose.

TABLE 6 below shows the Compound 1 ophthalmic solutions that were administered to each cohort.

TABLE 6

| Cohort | Compound 1 Regimen | Compound 1 (n) | Placebo (n) | Total (n) |
|---|---|---|---|---|
| 1 | 5 mg/mL QD | 9 | 3 | 12 |
| 2 | 15 mg/mL QD | 9 | 3 | 12 |
| 3 | 40 mg/mL QD | 9 | 3 | 12 |
| 4 | 40 mg/mL BID MTD (maximum tolerated dose) | 9 | 3 | 12 |

For cohort 1, on the morning of day 1 and day 2, all subjects were administered a single dose (one drop of approximately 30 μL of the dosing solution (Compound 1 or placebo) corresponding to the respective dose level) into the right eye only. If no AEs related to the investigational medicinal product (IMP) that represented a cause for concern were observed, then treatment was administered to both eyes once daily on the mornings of days 3 to 7. For all subsequent cohorts, dose administration was to both eyes on all 7 days (except cohort 4, in which treatment was administered in both eyes twice daily (AM and PM) on days 1-6 with a final single dose in both eyes on the morning of day 7).

Diurnal time point assessments of IOP were performed on day 1 and day 7 in both eyes at pre-dose, and 2, 4, and 8 hours post-dose in all cohorts.

The Compound 1 ophthalmic solution used for the trial was formulated as a sterile unpreserved solution of Compound 1 (0.5% w/v to 4.0% w/v, or 5 mg/mL to 40 mg/mL; as the sodium salt) in a vehicle containing 15% w/v HPβCD and 1% w/v mannitol and adjusted to a pH of 6.5-7.5 with 1N Hydrochloric Acid and/or 1N Sodium Hydroxide. The solution was filtered through sterile 0.22-μm filters, and 0.5 mL was aseptically filled into single-use sterile dose administration bottles suitable for ophthalmic delivery. Placebo was the same as the vehicle for the Compound 1 ophthalmic solution. Compound 1 was stored at United States Pharmacopeia (USP) controlled room temperature.

Figure 9:
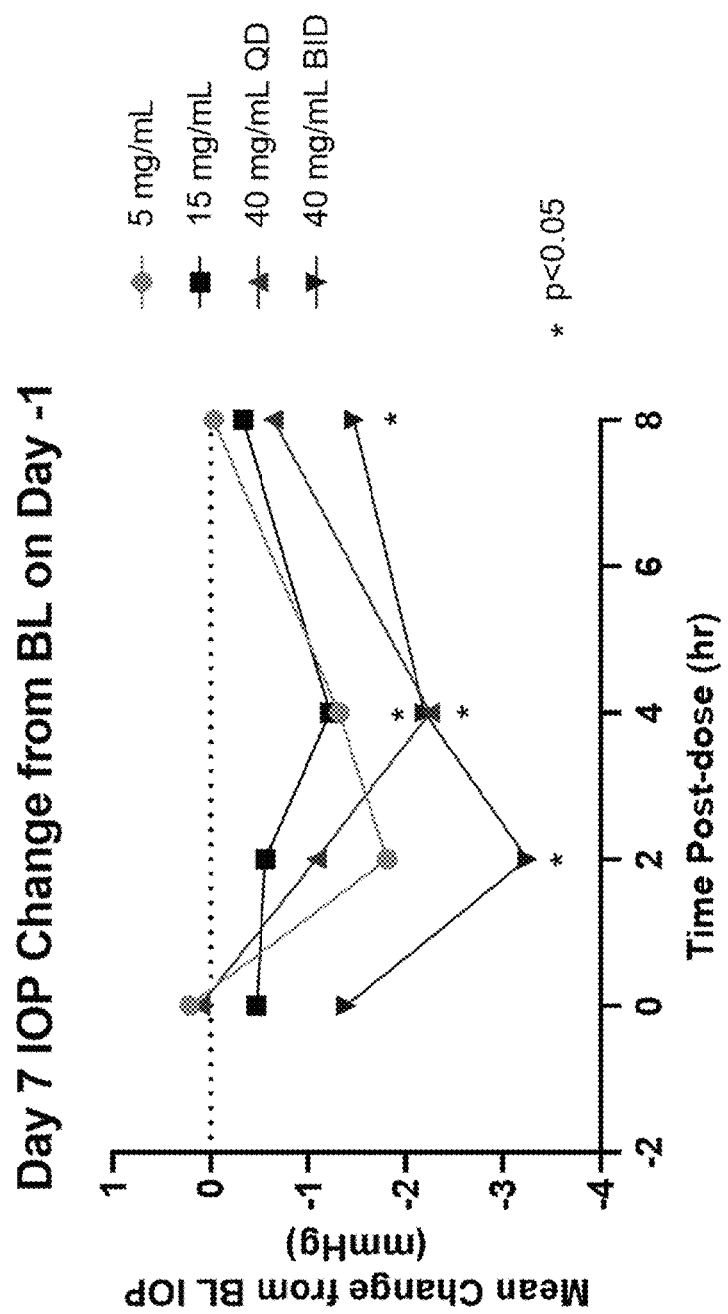
FIG. 9 shows that an ANCOVA model supported a dose response in Compound 1 IOP reduction.

FIG. 9 shows that an ANCOVA model supported a dose response in Compound 1 IOP reduction. The data in FIG. 9 show that the mean diurnal reduction in the study eye in the 40 mg/mL QD and BID doses were superior to the 15 mg/mL dose; −1.93 mmHg (p=0.003) and −2.24 mmHg (p<0.001), respectively.

Figure 10:
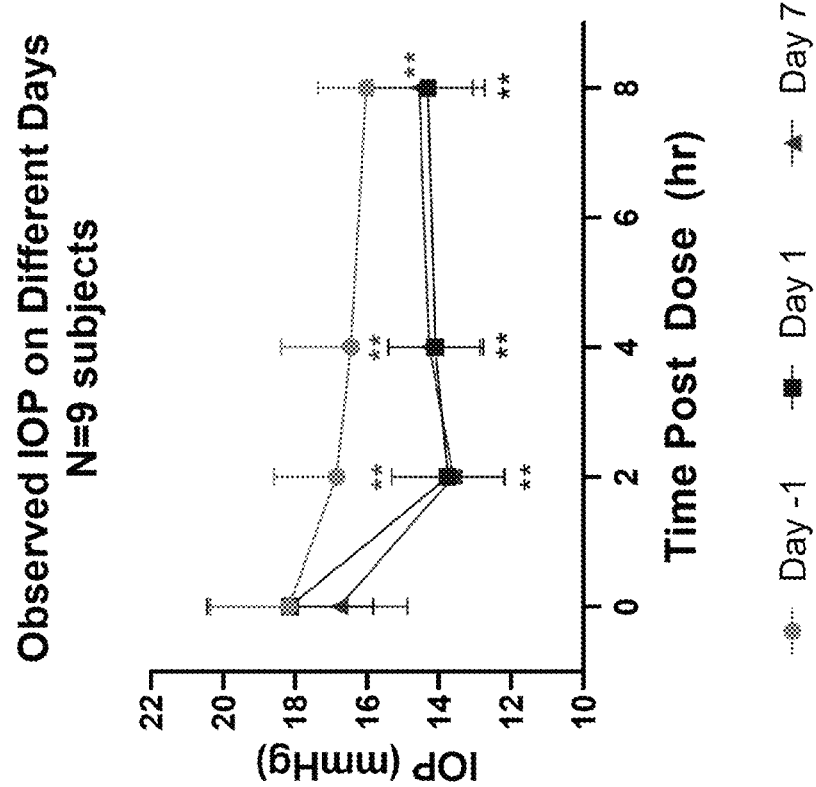
FIG. 10 shows that there were significant TOP reductions from baseline at 2, 4, and 8 hours post-dose on days 1 and 7 of the treatment regimen.

FIG. 10 shows that the 40 mg/ml dose resulted in significant TOP reductions from baseline at 2, 4, and 8 hours post-dose on days 1 and 7 of the treatment regimen.

Figure 11:
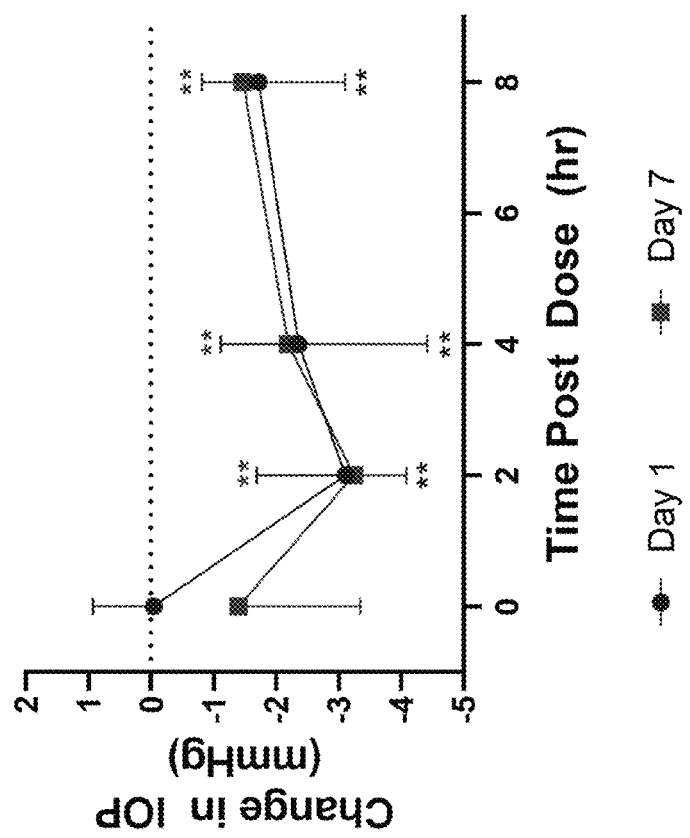
FIG. 11 shows that were a persistent TOP reduction on day 7 at the 0-hour, pre-dose time point (12 hours after the previous dose).

FIG. 11 shows that the 40 mg/ml dose resulted in a persistent TOP reduction on day 7 at the 0-hour, pre-dose time point (12 hours after the previous dose).

EMBODIMENTS

The following non-limiting embodiments provide illustrative examples of the invention, but do not limit the scope of the invention.

Embodiment 1. A method for modulating fluid outflow in an eye of a subject in need thereof, the method comprising administering to the subject a therapeutically-effective amount of a Tie-2 activator, wherein administration of the Tie-2 activator in the subject modulates the fluid outflow by at least about 20% as compared to absence of administration.

Embodiment 2. The method of embodiment 1, wherein the fluid outflow that is modulated by the administration is outflow of aqueous humor.

Embodiment 3. The method of embodiment 1 or 2, wherein the administration reduces intraocular pressure in the eye of the subject by at least about 15%.

Embodiment 4. The method of any one of embodiments 1-3, wherein Tie-2 is activated in a Schlemm's canal of the subject upon the administration of the Tie-2 activator.

Embodiment 5. The method of any one of embodiments 1-4, wherein the Tie-2 activator binds to HPTPβ in a Schlemm's canal of the subject.

Embodiment 6. The method of any one of embodiments 1-4, wherein the Tie-2 activator inhibits HPTPβ in a Schlemm's canal of the subject.

Embodiment 7. The method of any one of embodiments 1-6, wherein the modulating is an increase in the fluid outflow in the eye of the subject.

Embodiment 8. The method of any one of embodiments 1-7, wherein the fluid outflow is increased by at least about 25%.

Embodiment 9. The method of any one of embodiments 1-8, wherein the fluid outflow is increased by about 2 nL/min/mmHg to about 4 nL/min/mmHg.

Embodiment 10. The method of any one of embodiments 1-9, wherein the administration is topical.

Embodiment 11. The method of any one of embodiments 1-10, wherein the administration is topical to the eye of the subject.

Embodiment 12. The method of any one of embodiments 1-9, wherein the administration is subcutaneous.

Embodiment 13. The method of any one of embodiments 1-12, wherein the Tie-2 activator is administered to the subject as a unit dosage form.

Embodiment 14. The method of embodiment 13, wherein the unit dosage form is formulated as a drop.

Embodiment 15. The method of embodiment 14, wherein the drop contains an amount of the Tie-2 activator that is from about 1% to about 5% of the unit dosage form by mass.

Embodiment 16. The method of embodiment 14, wherein the drop further comprises a pharmaceutically-acceptable excipient.

Embodiment 17. The method of embodiment 16, wherein the pharmaceutically-acceptable excipient is a dextrose.

Embodiment 18. The method of embodiment 16, wherein the pharmaceutically-acceptable excipient is a cyclodextrin.

Embodiment 19. The method of any one of embodiments 1-18, wherein the Tie-2 activator is a compound of the formula:

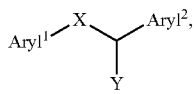

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thio-ether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

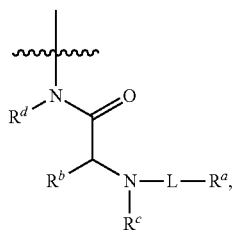

wherein:
L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond, or together with any of R$^a$, R$^b$, R$^c$, and R$^d$ forms a ring that is substituted or unsubstituted;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^a$, R$^c$, and R$^d$ forms a ring that is substituted or unsubstituted;
R$^c$ is H or alkyl which is substituted or unsubstituted, or together with any of L$^2$,
R$^a$, R$^b$, and R$^d$ forms a ring that is substituted or unsubstituted;
R$^d$ is H or alkyl which is substituted or unsubstituted, or together with any of L$^2$,
R$^a$, R$^b$, and R$^c$ forms a ring that is substituted or unsubstituted; and
R$^g$ is H, alkyl, alkenyl, alkynyl, aryl, arylalkyl, heterocyclyl, heterocyclylalkyl, heteroaryl, or heteroarylalkyl, any of which is substituted or unsubstituted,
or a pharmaceutically-acceptable salt thereof.

Embodiment 20. The method of embodiment 19, wherein:
Aryl$^1$ is substituted or unsubstituted phenyl;
Aryl$^1$ is substituted or unsubstituted heteroaryl; and
X is alkylene.

Embodiment 21. The method of embodiment 19 or 20, wherein:
Aryl$^1$ is substituted phenyl;
Aryl$^1$ is substituted heteroaryl; and
X is methylene.

Embodiment 22. The method of any one of embodiments 19-21, wherein the compound that activates Tie-2 is a compound of the formula:

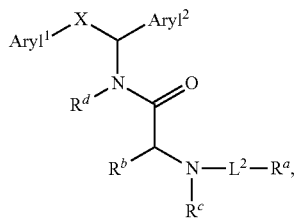

wherein
Aryl$^1$ is para-substituted phenyl;
Aryl$^1$ is substituted heteroaryl;
X is methylene;
L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted;
R$^c$ is H or alkyl which is substituted or unsubstituted; and
R$^d$ is H or alkyl which is substituted or unsubstituted.

Embodiment 23. The method of embodiment 22, wherein:
Aryl$^1$ is para-substituted phenyl;
Aryl$^1$ is a substituted thiazole moiety;
X is methylene;
L$^2$ together with the nitrogen atom to which L$^2$ is bound forms a carbamate linkage;
R$^a$ is alkyl, which is substituted or unsubstituted;
R$^b$ is arylalkyl, which is substituted or unsubstituted;
R$^c$ is H; and
R$^d$ is H.

Embodiment 24. The method of any one of embodiments 19-23, wherein Aryl$^2$ is:

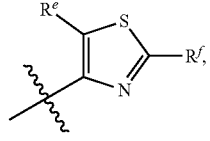

wherein:
- $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and
- $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 25. The method of embodiment 24, wherein:
- $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
- $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 26. The method of embodiment 24, wherein:
- $R^e$ is H, OH, F, Cl, Br, I, alkyl, or an alkoxy group, any of which is substituted or unsubstituted; and
- $R^f$ is alkyl, aryl, heterocyclyl, or heteroaryl, any of which is substituted or unsubstituted.

Embodiment 27. The method of any one of embodiments 19-26, wherein:
- Aryl$^1$ is 4-phenylsulfamic acid;
- $R^a$ is alkyl, which is substituted or unsubstituted;
- $R^b$ is arylalkyl, which is substituted or unsubstituted;
- $R^e$ is H; and
- $R^f$ is heteroaryl.

Embodiment 28. The method of embodiment 19, wherein the compound is:

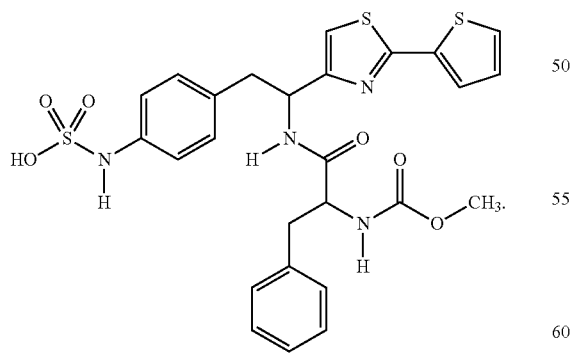

Embodiment 29. The method of embodiment 19, wherein the compound is:

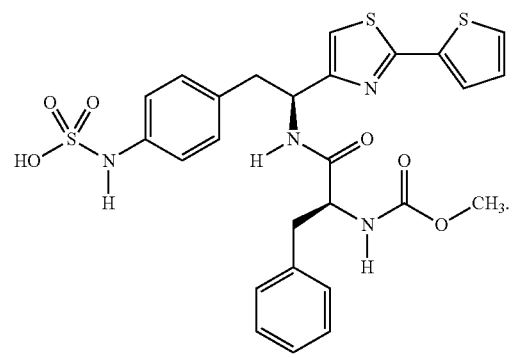 [SMILES: COC(=O)N[C@@H](Cc1ccccc1)C(=O)N[C@@H](Cc1ccc(NS(=O)(=O)O)cc1)c1csc(-c2cccs2)n1]

Embodiment 30. The method of embodiment 24, wherein:
- Aryl$^1$ is 4-phenylsulfamic acid;
- $R^a$ is alkyl, which is substituted or unsubstituted;
- $R^b$ is arylalkyl, which is substituted or unsubstituted;
- $R^e$ is H; and
- $R^f$ is alkyl.

Embodiment 31. The method of embodiment 19, wherein the compound is:

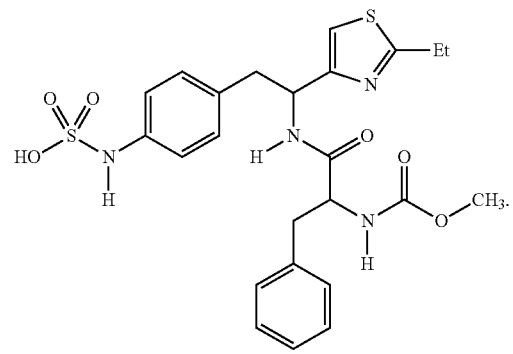 [SMILES: CCc1nc(C(Cc2ccc(NS(=O)(=O)O)cc2)NC(=O)C(Cc2ccccc2)NC(=O)OC)cs1]

Embodiment 32. The method of embodiment 19, wherein the compound is:

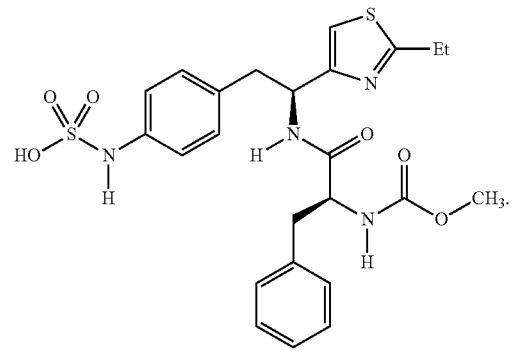 [SMILES: CCc1nc([C@H](Cc2ccc(NS(=O)(=O)O)cc2)NC(=O)[C@H](Cc2ccccc2)NC(=O)OC)cs1]

Embodiment 33. The method of any one of embodiments 19-23, wherein Aryl$^2$ is:

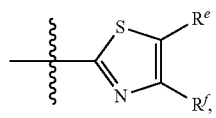

wherein:
R$^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and R$^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 34. The method of embodiment 33, wherein:
R$^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
R$^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 35. The method of embodiment 33, wherein:
R$^e$ is H, OH, F, Cl, Br, I, alkyl, or an alkoxy group, any of which is substituted or unsubstituted; and
R$^f$ is alkyl, aryl, heterocyclyl, or heteroaryl, any of which is substituted or unsubstituted.

Embodiment 36. The method of embodiment 33, wherein:
Aryl$^1$ is 4-phenylsulfamic acid;
R$^a$ is alkyl, which is substituted or unsubstituted;
R$^b$ is arylalkyl, which is substituted or unsubstituted;
R$^e$ is H; and
R$^f$ is heteroaryl.

Embodiment 37. The method of embodiment 19, wherein the compound is:

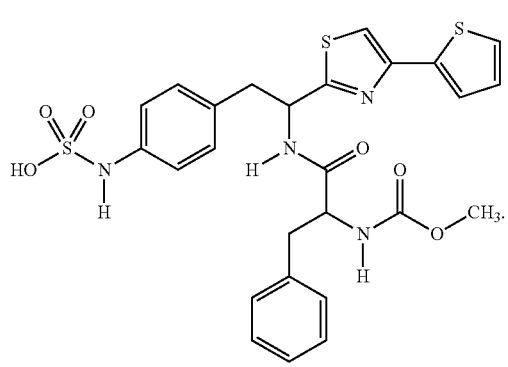 [SMILES: COC(=O)NC(Cc1ccccc1)C(=O)NC(Cc1ccc(NS(=O)(=O)O)cc1)c1nc(-c2cccs2)cs1]

Embodiment 38. The method of embodiment 19, wherein the compound is:

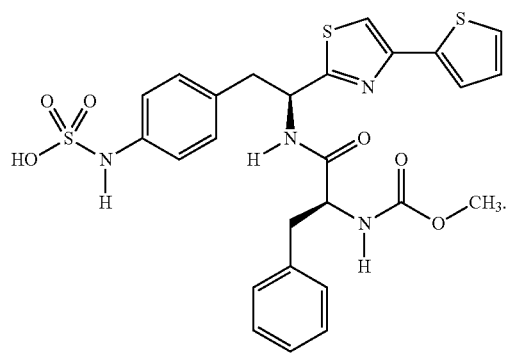 [SMILES: COC(=O)N[C@@H](Cc1ccccc1)C(=O)N[C@@H](Cc1ccc(NS(=O)(=O)O)cc1)c1nc(-c2cccs2)cs1]

Embodiment 39. The method of embodiment 19, wherein the compound is:

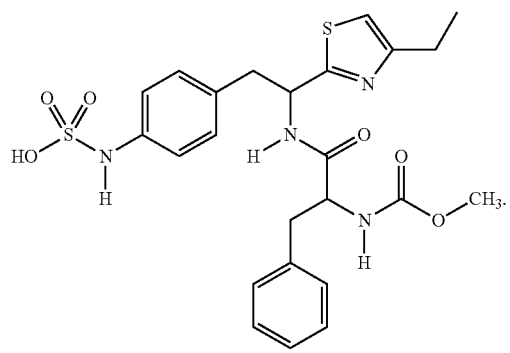 [SMILES: CCc1csc(C(Cc2ccc(NS(=O)(=O)O)cc2)NC(=O)C(Cc2ccccc2)NC(=O)OC)n1]

Embodiment 40. The method of embodiment 19, wherein the compound is:

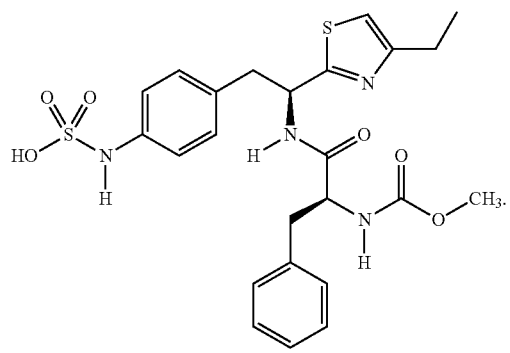 [SMILES: CCc1csc([C@H](Cc2ccc(NS(=O)(=O)O)cc2)NC(=O)[C@H](Cc2ccccc2)NC(=O)OC)n1]

Embodiment 41. A method for increasing area of a Schlemm's canal in a subject in need thereof, the method comprising administering to the subject a therapeutically-effective amount of a Tie-2 activator, wherein administration of the Tie-2 activator in the subject increases area of the Schlemm's canal by at least about 10% as compared to absence of administration.

Embodiment 42. The method of embodiment 41, wherein the administration reduces intraocular pressure in the eye of the subject by at least about 30%.

Embodiment 43. The method of embodiment 41 or 42, wherein Tie-2 is activated in the Schlemm's canal of the subject upon the administration of the Tie-2 activator.

Embodiment 44. The method of any one of embodiments 41-43, wherein the Tie-2 activator binds to HPTPβ in the Schlemm's canal of the subject.

Embodiment 45. The method of any one of embodiments 41-44, wherein the Tie-2 activator inhibits HPTPβ in the Schlemm's canal of the subject.

Embodiment 46. The method of any one of embodiments 41-45, wherein the administration is topical.

Embodiment 47. The method of any one of embodiments 41-45, wherein the administration is topical to the eye of the subject.

Embodiment 48. The method of any one of embodiments 41-45, wherein the administration is subcutaneous.

Embodiment 49. The method of any one of embodiments 41-48, wherein the Tie-2 activator is administered to the subject as a unit dosage form.

Embodiment 50. The method of embodiment 49, wherein the unit dosage form is formulated as a drop.

Embodiment 51. The method of embodiment 49, wherein the drop contains an amount of the Tie-2 activator that is from about 1% to about 5% of the unit dosage form by mass.

Embodiment 52. The method of embodiment 50 or 51, wherein the drop further comprises a pharmaceutically-acceptable excipient.

Embodiment 53. The method of embodiment 52, wherein the pharmaceutically-acceptable excipient is a dextrose.

Embodiment 54. The method of embodiment 52, wherein the pharmaceutically-acceptable excipient is a cyclodextrin.

Embodiment 55. The method of any one of embodiments 41-54, wherein the Tie-2 activator is a compound of the formula:

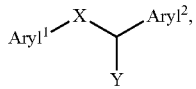

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thio-ether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

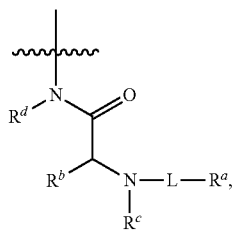

wherein:
L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond, or together with any of R$^a$, R$^b$, R$^c$, and R$^d$ forms a ring that is substituted or unsubstituted;

R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted;

R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^a$, R$^c$, and R$^d$ forms a ring that is substituted or unsubstituted;

R$^c$ is H or alkyl which is substituted or unsubstituted, or together with any of L$^2$, R$^a$, R$^b$, and R$^d$ forms a ring that is substituted or unsubstituted;

R$^d$ is H or alkyl which is substituted or unsubstituted, or together with any of L$^2$, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt thereof.

Embodiment 56. The method of embodiment 55, wherein:
Aryl$^1$ is substituted or unsubstituted phenyl;
Aryl$^2$ is substituted or unsubstituted heteroaryl; and
X is alkylene.

Embodiment 57. The method of embodiment 55 or 56, wherein:
Aryl$^1$ is substituted phenyl;
Aryl$^2$ is substituted heteroaryl; and
X is methylene.

Embodiment 58. The method of any one of embodiments 55-57, wherein the compound that activates Tie-2 is a compound of the formula:

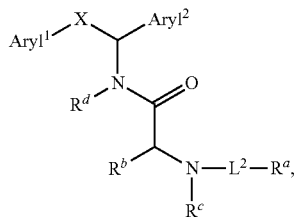

wherein
Aryl$^1$ is para-substituted phenyl;
Aryl$^2$ is substituted heteroaryl;
X is methylene;
L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted;
R$^c$ is H or alkyl which is substituted or unsubstituted; and
R$^d$ is H or alkyl which is substituted or unsubstituted.

Embodiment 59. The method of embodiment 58, wherein:
Aryl$^1$ is para-substituted phenyl;
Aryl$^2$ is a substituted thiazole moiety;
X is methylene;
L$^2$ together with the nitrogen atom to which L$^2$ is bound forms a carbamate linkage;

Rª is alkyl, which is substituted or unsubstituted;

R^b is arylalkyl, which is substituted or unsubstituted;

R^c is H; and

R^d is H.

Embodiment 60. The method of any one of embodiments 55-59, wherein Aryl² is:

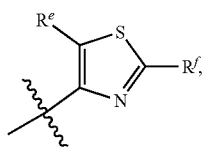

wherein:

R^e is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and R^f is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 61. The method of embodiment 60, wherein:

R^e is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and R^f is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 62. The method of embodiment 60, wherein:

R^e is H, OH, F, Cl, Br, I, alkyl, or an alkoxy group, any of which is substituted or unsubstituted; and R^f is alkyl, aryl, heterocyclyl, or heteroaryl, any of which is substituted or unsubstituted.

Embodiment 63. The method of any one of embodiments 55-62, wherein:

Aryl¹ is 4-phenylsulfamic acid;

Rª is alkyl, which is substituted or unsubstituted;

R^b is arylalkyl, which is substituted or unsubstituted;

R^e is H; and

R^f is heteroaryl.

Embodiment 64. The method of embodiment 55, wherein the compound is:

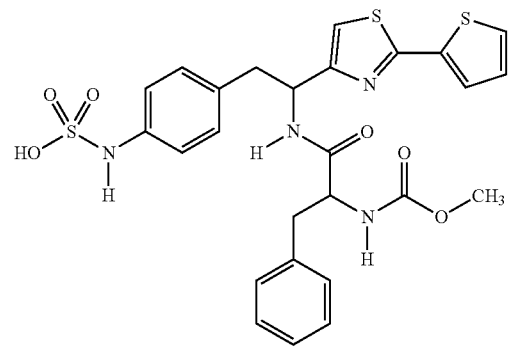

Embodiment 65. The method of embodiment 55, wherein the compound is:

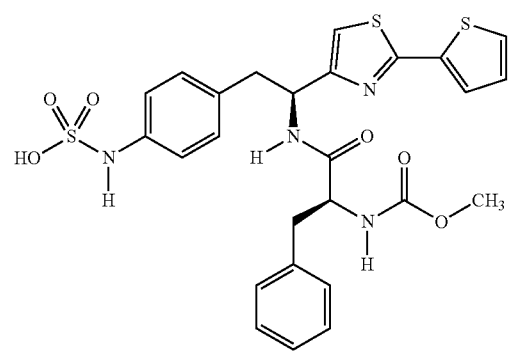

Embodiment 66. The method of embodiment 60, wherein:

Aryl¹ is 4-phenylsulfamic acid;

Rª is alkyl, which is substituted or unsubstituted;

R^b is arylalkyl, which is substituted or unsubstituted;

R^e is H; and

R^f is alkyl.

Embodiment 67. The method of embodiment 55, wherein the compound is:

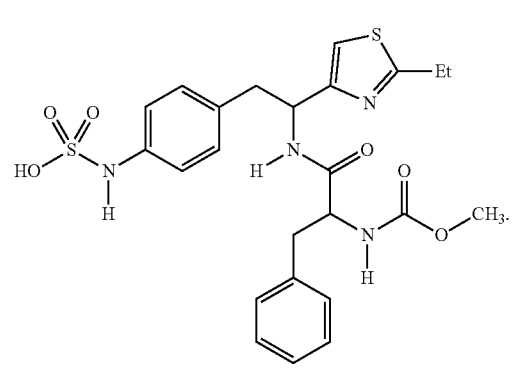 [SMILES: CCc1nc(C(Cc2ccc(NS(=O)(=O)O)cc2)NC(=O)C(Cc2ccccc2)NC(=O)OC)cs1]

Embodiment 68. The method of embodiment 55, wherein the compound is:

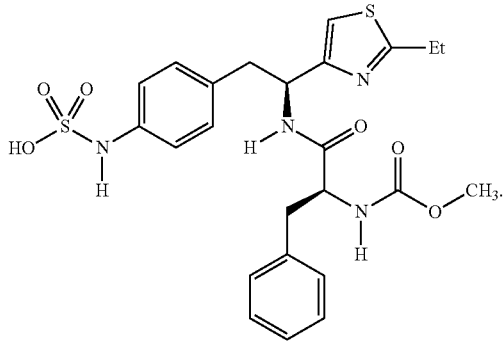 [SMILES: CCc1nc([C@H](Cc2ccc(NS(=O)(=O)O)cc2)NC(=O)[C@H](Cc2ccccc2)NC(=O)OC)cs1]

Embodiment 69. The method of any one of embodiments 55-59, wherein Aryl² is:

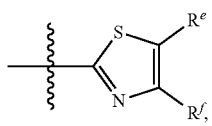

wherein:

R$^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and R$^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 70. The method of embodiment 69, wherein:

R$^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and R$^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 71. The method of embodiment 69, wherein:

R$^e$ is H, OH, F, Cl, Br, I, alkyl, or an alkoxy group, any of which is substituted or unsubstituted; and R$^f$ is alkyl, aryl, heterocyclyl, or heteroaryl, any of which is substituted or unsubstituted.

Embodiment 72. The method of embodiment 69, wherein:

Aryl¹ is 4-phenylsulfamic acid;

R$^a$ is alkyl, which is substituted or unsubstituted;

R$^b$ is arylalkyl, which is substituted or unsubstituted;

R$^e$ is H; and

R$^f$ is heteroaryl.

Embodiment 73. The method of embodiment 55, wherein the compound is:

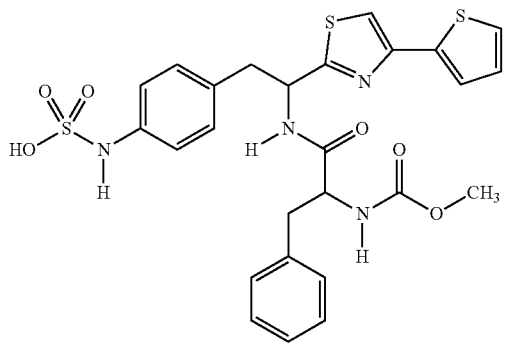

Embodiment 74. The method of embodiment 55, wherein the compound is:

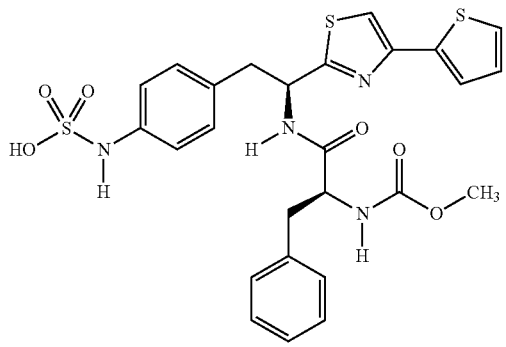

Embodiment 75. The method of embodiment 55, wherein the compound is:

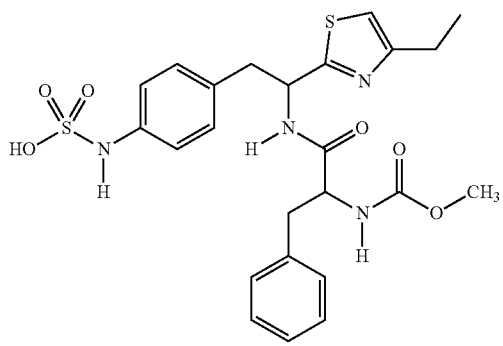

Embodiment 76. The method of embodiment 55, wherein the compound is:

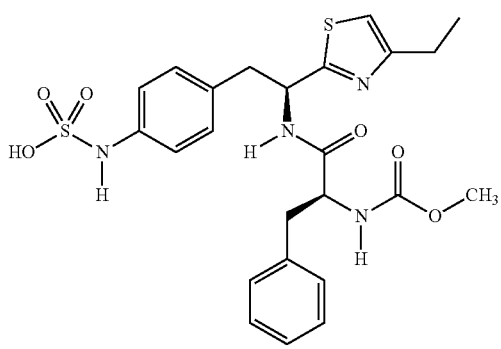

What is claimed is:

1. A method for increasing area of a Schlemm's canal in an eye of a subject in need thereof, the method comprising administering to the subject a therapeutically effective amount of a Tie-2 activator, wherein the Tie-2 activator is a compound of the formula:

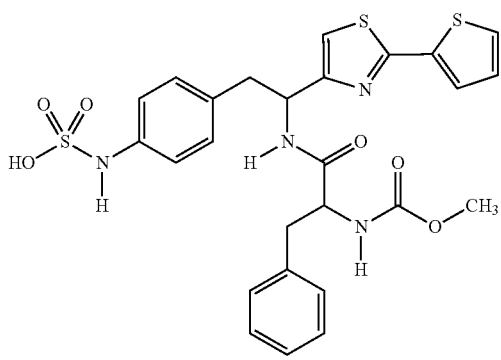 [SMILES: COC(=O)NC(Cc1ccccc1)C(=O)NC(Cc1ccc(NS(=O)(=O)O)cc1)c1csc(-c2cccs2)n1]

or a pharmaceutically-acceptable salt or zwitterion thereof, and
wherein administering the Tie-2 activator to the subject increases area of the Schlemm's canal by at least about 10% as compared to absence of administration.

2. The method of claim 1, wherein administering the Tie-2 activator in the subject increases area of the Schlemm's canal by at least about 12% as compared to absence of administration.

3. The method of claim 1, wherein the administering is by a unit dosage form, wherein the unit dosage form comprises the Tie-2 activator.

4. The method of claim 3, wherein the unit dosage form further comprises a pharmaceutically-acceptable excipient.

5. The method of claim 1, wherein the administering is by a sustained release formulation, wherein the sustained release formulation comprises the Tie-2 activator.

6. The method of claim 1, wherein the administering is by a solid hydrophobic polymer, wherein the solid hydrophobic polymer comprises the Tie-2 activator.

7. The method of claim 1, wherein the administering is by a microparticle, wherein the microparticle comprises the Tie-2 activator.

8. The method of claim 1, wherein the administering is topical.

9. The method of claim 1, wherein the administering is subcutaneous.

10. The method of claim 1, wherein the administering is intravitreal.

11. The method of claim 1, wherein Tie-2 is activated in the Schlemm's canal of the subject upon the administering of the Tie-2 activator.

12. The method of claim 1, wherein the Tie-2 activator binds to HPTPβ in a Schlemm's canal of the subject.

13. The method of claim 1, wherein the Tie-2 activator inhibits HPTPβ in a Schlemm's canal of the subject.

14. The method of claim 1, wherein the Tie-2 activator is a compound of the formula:

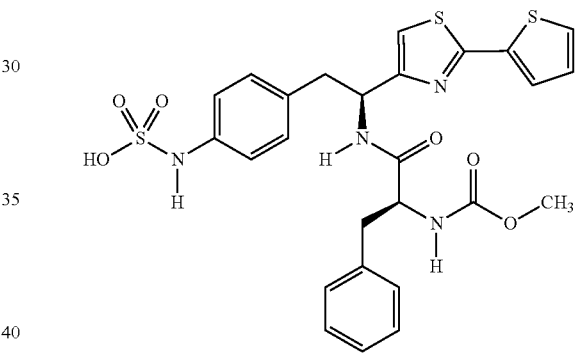

or a pharmaceutically-acceptable salt or zwitterion thereof.

15. The method of claim 1, wherein the increase in the area of the Schlemm's canal is determined by comparison to the area of the Schlemm's canal of the eye at baseline.

16. The method of claim 14, wherein the increase in the area of the Schlemm's canal is determined by comparison to the area of the Schlemm's canal of the eye at baseline.

* * * * *